United States Patent
Noble et al.

(10) Patent No.: US 10,232,039 B2
(45) Date of Patent: Mar. 19, 2019

(54) COMPOSITIONS AND METHODS FOR THE TREATMENT OF TISSUE FIBROSIS

(75) Inventors: Paul W. Noble, Chapel Hill, NC (US); Dianhua Jiang, Chapel Hill, NC (US)

(73) Assignee: Duke University, Durham, NC (US)

( * ) Notice: Subject to any disclaimer, the term of this patent is extended or adjusted under 35 U.S.C. 154(b) by 0 days.

(21) Appl. No.: 14/111,338

(22) PCT Filed: Apr. 12, 2012

(86) PCT No.: PCT/US2012/033246
§ 371 (c)(1),
(2), (4) Date: Oct. 11, 2013

(87) PCT Pub. No.: WO2012/142238
PCT Pub. Date: Oct. 18, 2012

(65) Prior Publication Data
US 2014/0050740 A1 Feb. 20, 2014

Related U.S. Application Data

(60) Provisional application No. 61/486,292, filed on May 15, 2011, provisional application No. 61/474,718, filed on Apr. 12, 2011.

(51) Int. Cl.
| | | |
|---|---|---|
| *C12N 15/11* | (2006.01) | |
| *A61K 39/395* | (2006.01) | |
| *C12Q 1/37* | (2006.01) | |
| *A61K 31/7088* | (2006.01) | |

(52) U.S. Cl.
CPC ...... *A61K 39/3955* (2013.01); *A61K 31/7088* (2013.01); *C12Q 1/37* (2013.01); *G01N 2333/8146* (2013.01)

(58) Field of Classification Search
None
See application file for complete search history.

(56) References Cited

U.S. PATENT DOCUMENTS

| | | | |
|---|---|---|---|
| 2003/0232440 A1 | 12/2003 | Karras et al. | |
| 2005/0214283 A1 | 9/2005 | Sackstein | |
| 2007/0286856 A1* | 12/2007 | Brown et al. | 424/133.1 |
| 2008/0152640 A1* | 6/2008 | Prehm | 424/130.1 |
| 2010/0008914 A1 | 1/2010 | Murray | |
| 2010/0092484 A1 | 4/2010 | Xu et al. | |
| 2011/0008366 A1 | 1/2011 | Wight et al. | |
| 2012/0244131 A1* | 9/2012 | Delacote | A61K 31/7088 424/93.21 |

FOREIGN PATENT DOCUMENTS

| | | |
|---|---|---|
| WO | WO 93/12227 | 6/1993 |
| WO | WO 2012/142238 | 12/2012 |

OTHER PUBLICATIONS

Pardo et al, Up-Regulation and Profibrotic Role of Osteopontin in Human Idiopathic Pulmonary Fibrosis, 2005, PLoS Medicine, vol. 2, issue 9, e251: 891-903.*
Zhao et al, An increase in hyaluronan by lung fibroblasts: A biomarker for intensity and activity of interstitial pulmonary fibrosis? 1999, Respirology, 4: 131-138.*
Chan et al, Deficiency of hyaluronan synthase 1 (Has1) results in chronic joint inflammation and widespread intra-articular fibrosis in a murine model of knee joint cartilage damage, 2015, Osteoarthritis and Cartilage, 23: 1879-1889.*
Acharya et al., "Fibroblast migration is mediated by CD44-dependent TGF beta activation," J Cell Sci (2008) 121:1393-1402.
Adamson et al., "The pathogenesis of bloemycin-induced pulmonary fibrosis in mice," Am J Pathol (1974) 77:185-197.
American Thoratic Society/European Respiratory Society, "Idiopathic pulmonary fibrosis: diagnosis and treatment. International consensus statement," Am J Respir Cirt Care Med (2000) 161:646-664.
Ando et al., "Cardiac microvascular endothelial cells express alpha-smooth muscle actin and show low NOS III activity," Am J Physiol (1999) 276:H1755-1768.
Ansel, Introduction to Pharmaceutical Dosage Forms, 2nd Ed., (1976).
Arch et al., "Participation in normal immune responses of a metastasis-inducing splice variant of CD44," Science (1992) 257:682-685.
Baker et al., "Divergent effects of tissue inhibitor of metalloproteinase-1, -2 or -3 overexpression on rat vascular smooth muscle cell invasion, proliferation, and death in vitro. TIMP-3 promotes apoptosis," J Clin Invest (1998) 101:1478-1487.
Banker et al., "Disperse systems: Solubilized products, Suspensions, and Emulsions", Modern Pharmaceutics (1979) p. 329-427.
Bjermer et al., "Hyaluronan and type III procollagen peptide concentration in bronchoalveolar lavage fluid in idiopathis pulmonary fibrosis," Thorax (1989) 44:126-131.
Bjoraker et al., "Prognostic significance of histopathologic subsets in idiopathic pulmonary fibrosis," Am J Resp Crit Care Med (1998) 157:199-203.

(Continued)

*Primary Examiner* — Ekaterina Poliakova-Georgantas
(74) *Attorney, Agent, or Firm* — Michael Best & Friedrich LLP

(57) ABSTRACT

Provided are methods of treating tissue fibrosis comprising administering to a subject in need of treatment an effective amount of an agent that inhibits a hyaluron synthase (HAS) or CD44. Further provided are methods of inhibiting myofibroblast invasion, or of reducing matrix deposition in the lung, the methods comprising administering to a subject in need of treatment an effective amount of an agent that inhibits a HAS or CD44. Further provided are methods of determining the progression of pulmonary fibrosis, the methods comprising determining the level of matrix metalloproteinase expression in a cell, and comparing the level of expression to that of a control cell, wherein an increased level of expression relative to the control cell indicates progression of the disease.

6 Claims, 37 Drawing Sheets

Specification includes a Sequence Listing.

(56) References Cited

OTHER PUBLICATIONS

Blankesteijn et al., "A homologue od *Drosophilia* tissue polarity gene frizzled is expressed in migrating myofibroblasts in the infarcted rat heart," Nat Med (1997) 3:541-544.
Camenisch et al., "Disruption of hyaluronan synthase-2 abrogates normal cardiac morphogenesis and hyaluronan-mediated transformation of epithelium to mesenchyme," J Clin Invest (2000) 106:349-360.
Chai et al., "Overexpression of hyaluronan in the tunica media promotes the development of atherosclerosis," Circ Res (2005) 96:583-591.
DeGrendele et al., "Requirement for CD44 in activated T cell extravasation into an inflamatory site," Science (1997) 278:672-675.
Epperly et al., "Bone marrow origin of myofibroblasts in irradiation pulmonary fibrosis," Am J Respir Cell Mol Biol (2003) 29:213-224.
Florin et al.,"Cre recombinase-mediated gene targeting of mesenchymal cells," Genesis (2004) 38:139-144.
Fukuda et al., "Patterns of pulmonary structural remodeling after experimental paraquat toxicity. The morphogenesis of intraalveolar fibrosis," Am J Pathol (1985) 118:452-475.
GenBank Accession No. AAC50692.1 (1996).
GenBank Accession No. CCDS6335.1 (2005).
GenBank Accession No. CCDS7897.1 (2005).
GenBank Accession No. NM_000610 (2014).
Gill et al., "Tissue inhibitor of metalloproteinases 3 regulates resolution of inflamation following acute lung injury," Am J Pathol (2010) 176:64-73.
Hager et al., "Genetic ablation of Bcl-x attenuates invasiveness without affecting apoptosis or tumor growth in a mouse model of pancreatic neuroendocrine cancer," PLoS ONE (2009) 4:e4455.
Hashimoto et al., "Bone marrow-derived progenitor cells in pulmonary fibrosis," J Clin Invest (2004) 113:243-252.
Hinz et al., "The myofibroblast: one function, multiple origins," Am J Pathol (2007) 170:1807-1816.
Horowitz et al., "Combinatorial activation of FAK and AKT by transforming growth factor-betal confers an anoikis-resistant phenotype to myofibroblasts," Cell Signal (2007) 19:761-771.
Internation Search Report and Written Opinion for Application No. PCT/US2012/33246 dated Oct. 1, 2012 (20 pages).
Itano et al., "Three isoforms of mammalian hyaluronan synthases have distinct enzymatic properties," J Biol Chem (1999) 274:25085-25092.
Jiang et al., "Hyaluronan as an Immune Regulator in Human Diseases," Physiol Rev (2011) 91:221-264.
Jiang et al., "Inhibition of pulmonary fibrosis in mice by CXCL10 requires glycosaminoglycan binding and syndecan-4," J. Clin Invest (2010) 120:2049-2057.
Jiang et al., "Regulation of lung injury and repair by Toll-like receptors and hyaluronan," Nat Med (2005) 11:1173-1179.
Jordana et al., "Heterogeneous proliferative characteristics of human adult lung fibroblast lines and clonally derived fibroblasts from control and fibrotic tissue," Am Rev Respir Dis (1988) 137:579-584.
Kang et al., "Transforming growth factor (TGF)-beta 1 stimulates pulmonary fibrosis and inflammation via a Bax-dependent, bid-activated pathway that involves matrix metalloproteinase-12," J Biol Chem (2007) 282:7723-7732.
Karnoub et al., "Mesenchymal stem cells within tumour stronoma promote breast cancer metastasis," Nature (2007) 449:557-563.
Kassiri et al., "Loss of TIMP3 enhances interstitial nepgritis and fibrosis," J Am Soc Nephrol (2009) 20:1223-1235.
Kessenbrock et al., "Matrix metalloproteinases: regulators of the tumor microenvironment," Cell (2010) 141:52-67.
Kim et al., "Epithelial cell alpha3beta1 integrin links beta-catenin and Smad signaling to promote myofibroblast formation and pulmonary fibrosis," J Clin Invest (2009) 119:213-224.

Kim et al., "TGF-beta1 stimulates production of gelatinase (MMP-9), collagenases (MMP-1, -13) and stromelysins (MMP-3, -10, -11) by human corneal epithelial cells," Exp Eye Res (2004) 79:263-274.
Köhler et al., "Continuous cultures of fused cells secreting antibody of predefined specificity", Nature (1975) vol. 256, p. 495-497.
Kuwano et al., "Mitochondria-mediated apoptosis of lung epithelial cells in idiopathic interstitial pneumonias," Lab Invest (2002) 82:1695-1706.
Larsson et al., "Fibrotic myofibroblasts manifest genome-wide derangements of translational control," PLoS ONE (2008) 3:a3220.
Lawson et al., "Characterization of fibroblast-specific protein 1 in pulmonary fibrosis," Am J Respir Crit Care Med (2005) 171:899-907.
Lesley et al., "CD44 and its interaction with extracellular matrix," Adv Immunol (1993) 54:271-335.
Li et al. Severe lung fibrosis requires an invasive fibroblast phenotype regulated by hyaluronan and CD44. J Exp Med. Jul. 2011, vol. 208(7), p. 1459-1471.
Li et al., "Silencing of hyaluronan synthase 2 suppresses the malignant phenotype of invasive breast cells," Int J Cancer (2007) 120:2557-2567.
Lieberman et al., Pharmaceutical Dosage Forms: Tablets (1981).
Lu et al., "Smooth muscle alpha-actin expression in endothelial cells derived from CD34+ human cord blood cells," Stem Cells (2004) 13:521-527.
Madala et al., "Matrix metalloproteinase 12-deficiency augments extracellular matrix degrading metalloproteinases and attenuates IL-13-dependent fibrosis," J Immunol (2010) 184:3955-3963.
Marrero-Diaz et al., "Polarized MT1-MMP-CD44 interaction and CD44 cleavage during cell retraction reveal an essential role for MT1-MMP in CD44-mediated invasion," Cell Motil Cytoskeleton (2009) 66:48-61.
Matsumoto et al., "Conditional inactivation of Has2 reveals a crucial role for hyaluronan in skeletal growth, patterning, chondrocyte maturation and joint formation in the developing limb," Development (2009) 136:2825-2835.
McKee et al., "Hyaluronan (HA) fragments induce chemokine gene expression in alveolar macrophages. The role of HA size and CD44," J Clin Invest (1996) 98:2403-2413.
Mikecz et al., "Anti-CD44 treatment abrogates tissue oedema and leukocyte infiltration in murine arthritis," Nature Medicine (1995) 1:558-563.
Mittaz et al., "Neonatal calyceal dilation and renal fibrosis resulting from loss od Adamts-1 in mouse kidney is due to a developmental dysgenesis," Nephrol Dial Transplant (2005) 20:419-423.
Miyake et al., "Hyaluronate can function as a cell adhesion molecule and CD44 participates in hyaluronate recognition," J Exp Med (1990) 172:69-75.
Munger et al., "The integrin alpha v beta 6 binds and activates latent TGF beta 1: a mechanism for regulating pulmonary inflammation and fibrosis," Cell (1999) 96:319-328.
Murphy, "The ADAMs: signalling scissors in the tumour microenvironment," Nat Rev Cancer (2008) 8:929-941.
Noble et al., "Hyluronate activation of CD44 induces inculin-like growth factor-1 expression by a tumor necrosis factor-alpha-dependent mechanism in murine macrophages," J Clin Invest (1993) 91:2368-2377.
Papakonstantinou et al., "Increased hyaluronic acid content in idiopathic pulmonary arterial hypertenion" Eur Respir J 2008; 32: 1504-1512.
Peled et al., "Expression of alpha-smooth muscle actin in murine bone marrow stromal cells," Blood (1991) 78:304-309.
Qian et al., "Expression of the integrin alpha 4 beta 1 on melanoma cells can inhibit the invasive stage of metastasis formation," Cell (1994) 77:335-347.
Remington, Pharmaceutical Science, 16th Ed. (1980).
Schmits et al., "CD44 regulates hematopoietic progenitor distribution, granuloma formation, and tumorigenicity," Blood (1997) 90:2217-2233.
Selman et al., "Idiopathic pulmonary fibrosis: an epithelial/fibroblastic cross-talk disorder," Respir Res (2002) 3:3.
Shindo et al., "ADAMTS-1: a metalloproteinase-disintegrin essential for normal growth, fertility, and organ morphology and function," J Clin Invest (2000) 105:1345-1352.

(56) References Cited

OTHER PUBLICATIONS

Siegelman et al., "Activation and interaction of CD44 and hyaluronan in immunological systems," J Leukoc Biol (1999) 66:315-321.
Sime et al., "Adenovector-mediated gene transfer of active transforming growth factor-beta 1 induces prolonged severe fibrosis in rat lung," J Clin Invest (1997) 100:768-776.
Spicer et al., "Molecular cloning and characterization of a putative mouse hyaluronan synthase," J Biol Chem (1996) 271:23400-23406.
Stamenkovic, "Matrix metalloproteinases in tumor invasion and metastasis," Semin Cancer Biol (2000) 10:415-433.
Tager et al., "The lysophosphatidic acid receptor LPA1 links pulmonary fibrosis to lung injury by mediating fibroblast recruitment and vascular leak," Nat Med (2008) 14:45-54.
Tanjore et al., "Contribution of epithelial-derived fibroblasts to bleomycin-induced lung fibrosis," Am J Respir Crit Care Med (2009) 180:657-665.
Teder et al., "Resolution of lung inflammation by CD44," Science (2002) 296:155-158.
Thannickal et al., "Myofibroblast differentiation by transforming growth factor-beta 1 is dependent on cell adhesion and integrin signaling via focal adhesion kinase," J Biol Chem (2003) 278:12384-12389.
Toole, "Hyaluronan: from extracellular glue to pericellular cue," Nat Rev Cancer (2004) 4:528-539.
Vaccaro et al., "Alveolar wall basement membranes in bleomycin-induced pulmonary fibrosis," Am Rev Respir Dis (1985) 132:905-912.
Webber et al., "Hyaluronan Orchestrates Transforming Growth Factor-{beta} 1-dependent Maintenance of Myofibroblast Phenotype," J Biol Chem (2009) 284:9083-9092.
White et al., "Integrin alpha4beta1 regulates migration across basement membranes by lung fibroblasts: a role for phosphatase and tensin homologue deleted on chromosome 10," Am J Respir Crit Care Med (2003) 168:436-442.
White et al., "Pathogenetic mechanismn in usual interstitial pneumonia/idiopathic pulmonary fibrosis," J Pathol (2003) 201:343-354.
Yu et al., "Cell surface-localized matrix metalloproteinase-9 proteolytically activates TGF-beta and promotes tumor invasion and angiogenesis," Gene Dev (2000) 14:163-176.
Zhang et al., "Lung fibroblast alpha-smooth muscle actin expression and contractile phenotype in bleomycin-induced pulmonary fibrosis," Am J Pathol (1996) 148:527-537.
Zhu et al., "Urolinase receptor mediates lung fibroblast attachment and migration toward provisional matrix proteins through interaction with multiple integrins," Am J Physiol Lung Cell (2009) 297:L97-108.
Hajjaji et al. The Journal of Rheumatology 2003, 30, 2444-2451.
Moreland et al. Arthritis Research & Therapy 2003, 5, 54-67.
Weigel; Hyaluronan Synthase: The Mechanism of Initiation at the Reducing End and a Pendulum Model for Polysaccharide Translocation to the Cell Exterior; International Journal of Cell Biology; vol. 2015; Article ID 367579; accepted Jan. 14, 2015; 15 pages.
Lennon, et al.; Role of Hyaluronan and Hyaluronan-Binding Proteins in Lung Pathobiology; Am J Physiol Lung Cell Mol Physiol 301; L137-L147; 2011; May 13, 2011; 11 pages.
Karbownik, et al; Hyaluronan: Towards Novel Anti-Cancer Therapeutics; Pharmacological Report; 2013; 65; 1056-1074; ISSN 1734 1140; 19 pages.
Weigel, International Journal of Cell Biology 2015, Article ID 367579, 15 pages.
Vigetti et al., Matrix Biology 2014, 35, 8-13, 6 pages.
Karbownik et al., Pharmacological Reports 2013, 65, 1056-1074, 19 pages.
Lennon et al., Am. J. Physiol. Lung Cell Mol. Physiol. 2011, 301, L137-L147, 11 pages.
Wang et al., Am. J. Pathol. 2011, 178, 956-963, 8 pages.
Li et al. Severe lung fibrosis requires an invasive fibroblast phenotype regulated by hyaluronan and CD 44; (J. Exp. Med. 2011, 208, 1459-1471).

* cited by examiner

A

B

C

D

A 1.75 U/Kg

ASMA-HAS2+
ASMA-HAS2-

2.5 U/Kg

ASMA-HAS2+
ASMA-HAS2-

E

F

G

H

SEQUENCE LISTING

```
<160> NUMBER OF SEQ ID NOS: 20

<210> SEQ ID NO 1
<211> LENGTH: 19
<212> TYPE: DNA
<213> ORGANISM: Artificial
<220> FEATURE:
<223> OTHER INFORMATION: primer

<400> SEQUENCE: 1
tcgcaacacg taacgcaat                                          19

<210> SEQ ID NO 2
<211> LENGTH: 23
<212> TYPE: DNA
<213> ORGANISM: Artificial
<220> FEATURE:
<223> OTHER INFORMATION: primer

<400> SEQUENCE: 2
acttctcttt ttccacccca ttt                                     23

<210> SEQ ID NO 3
<211> LENGTH: 19
<212> TYPE: DNA
<213> ORGANISM: Artificial
<220> FEATURE:
<223> OTHER INFORMATION: primer

<400> SEQUENCE: 3
cccactgctg gcccttcta                                          19

<210> SEQ ID NO 4
<211> LENGTH: 18
<212> TYPE: DNA
<213> ORGANISM: Artificial
<220> FEATURE:
<223> OTHER INFORMATION: primer

<400> SEQUENCE: 4
```

-continued tcacgttgca ggcatcgt           18

<210> SEQ ID NO 5
<211> LENGTH: 18
<212> TYPE: DNA
<213> ORGANISM: Artificial
<220> FEATURE:
<223> OTHER INFORMATION: primer

<400> SEQUENCE: 5
tgcacgcacc tcgatgtg           18

<210> SEQ ID NO 6
<211> LENGTH: 15
<212> TYPE: DNA
<213> ORGANISM: Artificial
<220> FEATURE:
<223> OTHER INFORMATION: primer

<400> SEQUENCE: 6
ggcccccctg gcatt              15

<210> SEQ ID NO 7
<211> LENGTH: 21
<212> TYPE: DNA
<213> ORGANISM: Artificial
<220> FEATURE:
<223> OTHER INFORMATION: primer

<400> SEQUENCE: 7
cgagaggaag gatggcaaat t       21

<210> SEQ ID NO 8
<211> LENGTH: 20
<212> TYPE: DNA
<213> ORGANISM: Artificial
<220> FEATURE:
<223> OTHER INFORMATION: primer

<400> SEQUENCE: 8
agggacgcct catcaaacac         20

<210> SEQ ID NO 9
<211> LENGTH: 20
<212> TYPE: DNA
<213> ORGANISM: Artificial
<220> FEATURE:
<223> OTHER INFORMATION: primer

<400> SEQUENCE: 9
cccatgttcg tcatgggtgt         20

<210> SEQ ID NO 10
<211> LENGTH: 23
<212> TYPE: DNA
<213> ORGANISM: Artificial
<220> FEATURE:
<223> OTHER INFORMATION: primer

<400> SEQUENCE: 10
tggtcatgag tccttccacg ata     23

<210> SEQ ID NO 11
<211> LENGTH: 22
<212> TYPE: DNA
<213> ORGANISM: Artificial

```
<220> FEATURE:
<223> OTHER INFORMATION: primer

<400> SEQUENCE: 11
acgacgacct ttacatgatg ga                                              22

<210> SEQ ID NO 12
<211> LENGTH: 21
<212> TYPE: DNA
<213> ORGANISM: Artificial
<220> FEATURE:
<223> OTHER INFORMATION: primer

<400> SEQUENCE: 12
gatgtacatg gccgatttgc t                                               21

<210> SEQ ID NO 13
<211> LENGTH: 19
<212> TYPE: DNA
<213> ORGANISM: Artificial
<220> FEATURE:
<223> OTHER INFORMATION: primer

<400> SEQUENCE: 13
atcatctccg ccccttctg                                                  19

<210> SEQ ID NO 14
<211> LENGTH: 21
<212> TYPE: DNA
<213> ORGANISM: Artificial
<220> FEATURE:
<223> OTHER INFORMATION: primer

<400> SEQUENCE: 14
ggtcatgagc ccttccacaa c                                               21

<210> SEQ ID NO 15
<211> LENGTH: 21
<212> TYPE: DNA
<213> ORGANISM: Artificial
<220> FEATURE:
<223> OTHER INFORMATION: Synthetic

<400> SEQUENCE: 15
cagctcgatc taagtgcctt a                                               21

<210> SEQ ID NO 16
<211> LENGTH: 552
<212> TYPE: PRT
<213> ORGANISM: Homo sapiens

<400> SEQUENCE: 16
```

Met His Cys Glu Arg Phe Leu Cys Ile Leu Arg Ile Ile Gly Thr Thr
1               5                   10                  15

Leu Phe Gly Val Ser Leu Leu Leu Gly Ile Thr Ala Ala Tyr Ile Val
            20                  25                  30

Gly Tyr Gln Phe Ile Gln Thr Asp Asn Tyr Tyr Phe Ser Phe Gly Leu
        35                  40                  45

Tyr Gly Ala Phe Leu Ala Ser His Leu Ile Ile Gln Ser Leu Phe Ala
    50                  55                  60

Phe Leu Glu His Arg Lys Met Lys Lys Ser Leu Glu Thr Pro Ile Lys
65                  70                  75                  80

Leu Asn Lys Thr Val Ala Leu Cys Ile Ala Ala Tyr Gln Glu Asp Pro

```
                    85                  90                  95
Asp Tyr Leu Arg Lys Cys Leu Gln Ser Val Lys Arg Leu Thr Tyr Pro
                100                 105                 110

Gly Ile Lys Val Val Met Val Ile Asp Gly Asn Ser Glu Asp Asp Leu
                115                 120                 125

Tyr Met Met Asp Ile Phe Ser Glu Val Met Gly Arg Asp Lys Ser Ala
                130                 135                 140

Thr Tyr Ile Trp Lys Asn Asn Phe His Glu Lys Gly Pro Gly Glu Thr
145                 150                 155                 160

Asp Glu Ser His Lys Glu Ser Ser Gln His Val Thr Gln Leu Val Leu
                165                 170                 175

Ser Asn Lys Ser Ile Cys Ile Met Gln Lys Trp Gly Lys Arg Glu
                180                 185                 190

Val Met Tyr Thr Ala Phe Arg Ala Leu Gly Arg Ser Val Asp Tyr Val
                195                 200                 205

Gln Val Cys Asp Ser Asp Thr Met Leu Asp Pro Ala Ser Ser Val Glu
                210                 215                 220

Met Val Lys Val Leu Glu Glu Asp Pro Met Val Gly Val Gly Gly
225                 230                 235                 240

Asp Val Gln Ile Leu Asn Lys Tyr Asp Ser Trp Ile Ser Phe Leu Ser
                245                 250                 255

Ser Val Arg Tyr Trp Met Ala Phe Asn Ile Glu Arg Ala Cys Gln Ser
                260                 265                 270

Tyr Phe Gly Cys Val Gln Cys Ile Ser Gly Pro Leu Gly Met Tyr Arg
                275                 280                 285

Asn Ser Leu Leu His Glu Phe Val Glu Asp Trp Tyr Asn Gln Glu Phe
                290                 295                 300

Met Gly Asn Gln Cys Ser Phe Gly Asp Asp Arg His Leu Thr Asn Arg
305                 310                 315                 320

Val Leu Ser Leu Gly Tyr Ala Thr Lys Tyr Thr Ala Arg Ser Lys Cys
                325                 330                 335

Leu Thr Glu Thr Pro Ile Glu Tyr Leu Arg Trp Leu Asn Gln Gln Thr
                340                 345                 350

Arg Trp Ser Lys Ser Tyr Phe Arg Glu Trp Leu Tyr Asn Ala Met Trp
                355                 360                 365

Phe His Lys His His Leu Trp Met Thr Tyr Glu Ala Ile Ile Thr Gly
                370                 375                 380

Phe Phe Pro Phe Phe Leu Ile Ala Thr Val Ile Gln Leu Phe Tyr Arg
385                 390                 395                 400

Gly Lys Ile Trp Asn Ile Leu Leu Phe Leu Leu Thr Val Gln Leu Val
                405                 410                 415

Gly Leu Ile Lys Ser Ser Phe Ala Ser Cys Leu Arg Gly Asn Ile Val
                420                 425                 430

Met Val Phe Met Ser Leu Tyr Ser Val Leu Tyr Met Ser Ser Leu Leu
                435                 440                 445

Pro Ala Lys Met Phe Ala Ile Ala Thr Ile Asn Lys Ala Gly Trp Gly
                450                 455                 460

Thr Ser Gly Arg Lys Thr Ile Val Val Asn Phe Ile Gly Leu Ile Pro
465                 470                 475                 480

Val Ser Val Trp Phe Thr Ile Leu Leu Gly Gly Val Ile Phe Thr Ile
                485                 490                 495

Tyr Lys Glu Ser Lys Arg Pro Phe Ser Glu Ser Lys Gln Thr Val Leu
                500                 505                 510
```

Ile Gly Thr Leu Leu Tyr Ala Cys Tyr Trp Val Met Leu Leu Thr
       515                 520                 525

Leu Tyr Val Val Leu Ile Asn Lys Cys Gly Arg Arg Lys Lys Gly Gln
   530                 535                 540

Gln Tyr Asp Met Val Leu Asp Val
545                 550

<210> SEQ ID NO 17
<211> LENGTH: 1659
<212> TYPE: DNA
<213> ORGANISM: Homo sapiens

<400> SEQUENCE: 17

| | | | | | | |
|---|---|---|---|---|---|---|
| atgcattgtg | agaggtttct | atgtatcctg | agaataattg | gaaccacact | ctttggagtc | 60 |
| tctctcctcc | ttggaatcac | agctgcttat | attgttggct | accagtttat | ccaaacggat | 120 |
| aattactatt | tctcttttgg | actgtatggt | gccttttggg | catcacacct | catcatccaa | 180 |
| agcctgtttg | ccttttggga | gcaccgaaaa | atgaaaaaat | ccctagaaac | ccccataaag | 240 |
| ttgaacaaaa | cagttgccct | ttgcatcgct | gcctatcaag | aagatccaga | ctacttaagg | 300 |
| aaatgtttgc | aatctgtgaa | aaggctaacc | taccctggga | ttaaagttgt | catggtcata | 360 |
| gatgggaact | cagaagatga | cctttacatg | atggacatct | tcagtgaagt | catgggcaga | 420 |
| gacaaatcag | ccacttatat | ctggaagaac | aacttccacg | aaaagggtcc | cggtgagaca | 480 |
| gatgagtcac | ataagaaag | ctcgcaacac | gtaacgcaat | tggtcttgtc | caacaaaagt | 540 |
| atctgcatca | tgcaaaaatg | gggtggaaaa | agagaagtca | tgtacacagc | cttcagagca | 600 |
| ctgggacgaa | gtgtggatta | tgtacaggtt | tgtgattcag | acactatgct | tgacccagcc | 660 |
| tcatctgtgg | agatggtaaa | agttttagaa | gaagatccca | tggttggagg | tgttggggga | 720 |
| gatgtccaga | ttttaaacaa | gtacgattcc | tggatctcat | tcctcagcag | tgtaagatat | 780 |
| tggatggctt | ttaatataga | aagggcctgt | cagtcttatt | ttgggtgtgt | tcagtgcatt | 840 |
| agtggaccctc | tgggaatgta | cagaaactcc | ttgttgcatg | agtttgtgga | agattggtac | 900 |
| aatcaagaat | ttatgggcaa | ccaatgtagc | tttggtgatg | acaggcatct | cacgaaccgg | 960 |
| gtgctgagcc | tgggctatgc | aacaaaatac | acagctcgat | ctaagtgcct | tactgaaaca | 1020 |
| cctatagaat | atctcagatg | gctaaaccag | cagacccgtt | ggagcaagtc | ctacttccga | 1080 |
| gaatggctgt | acaatgcaat | gtggttccac | aaacatcact | tgtggatgac | ctacgaagcg | 1140 |
| attatcactg | gattctttcc | tttctttctc | attgccacag | taatccagct | cttctaccgg | 1200 |
| ggtaaaattt | ggaacattct | cctcttcttg | ttaactgtcc | agctagtagg | tctcataaaa | 1260 |
| tcatcttttg | ccagctgcct | tagaggaaat | atcgtcatgg | tcttcatgtc | tctctactca | 1320 |
| gtgttataca | tgtcgagttt | acttcccgcc | aagatgtttg | caattgcaac | aataaacaaa | 1380 |
| gctgggtggg | gcacatcagg | aaggaaaacc | attgttgtta | atttcatagg | actcattcca | 1440 |
| gtatcagttt | ggtttacaat | cctcctgggt | ggtgtgattt | tcaccattta | taggagtct | 1500 |
| aaaaggccat | tttcagaatc | caaacagaca | gttctaattg | ttggaacgtt | gctctatgca | 1560 |
| tgctattggg | tcatgctttt | gacgctgtat | gtagttctca | tcaataagtg | tggcaggcgg | 1620 |
| aagaagggac | aacaatatga | catggtgctt | gatgtatga | | | 1659 |

<210> SEQ ID NO 18
<211> LENGTH: 742
<212> TYPE: PRT
<213> ORGANISM: Homo sapiens

<400> SEQUENCE: 18

Met Asp Lys Phe Trp Trp His Ala Ala Trp Gly Leu Cys Leu Val Pro
1               5                   10                  15

Leu Ser Leu Ala Gln Ile Asp Leu Asn Ile Thr Cys Arg Phe Ala Gly
            20                  25                  30

Val Phe His Val Glu Lys Asn Gly Arg Tyr Ser Ile Ser Arg Thr Glu
        35                  40                  45

Ala Ala Asp Leu Cys Lys Ala Phe Asn Ser Thr Leu Pro Thr Met Ala
    50                  55                  60

Gln Met Glu Lys Ala Leu Ser Ile Gly Phe Glu Thr Cys Arg Tyr Gly
65                  70                  75                  80

Phe Ile Glu Gly His Val Val Ile Pro Arg Ile His Pro Asn Ser Ile
                85                  90                  95

Cys Ala Ala Asn Asn Thr Gly Val Tyr Ile Leu Thr Ser Asn Thr Ser
            100                 105                 110

Gln Tyr Asp Thr Tyr Cys Phe Asn Ala Ser Ala Pro Pro Glu Glu Asp
        115                 120                 125

Cys Thr Ser Val Thr Asp Leu Pro Asn Ala Phe Asp Gly Pro Ile Thr
130                 135                 140

Ile Thr Ile Val Asn Arg Asp Gly Thr Arg Tyr Val Gln Lys Gly Glu
145                 150                 155                 160

Tyr Arg Thr Asn Pro Glu Asp Ile Tyr Pro Ser Asn Pro Thr Asp Asp
                165                 170                 175

Asp Val Ser Ser Gly Ser Ser Ser Glu Arg Ser Ser Thr Ser Gly Gly
            180                 185                 190

Tyr Ile Phe Tyr Thr Phe Ser Thr Val His Pro Ile Pro Asp Glu Asp
        195                 200                 205

Ser Pro Trp Ile Thr Asp Ser Thr Asp Arg Ile Pro Ala Thr Thr Leu
    210                 215                 220

Met Ser Thr Ser Ala Thr Ala Thr Glu Thr Ala Thr Lys Arg Gln Glu
225                 230                 235                 240

Thr Trp Asp Trp Phe Ser Trp Leu Phe Leu Pro Ser Glu Ser Lys Asn
                245                 250                 255

His Leu His Thr Thr Thr Gln Met Ala Gly Thr Ser Ser Asn Thr Ile
            260                 265                 270

Ser Ala Gly Trp Glu Pro Asn Glu Glu Asn Glu Asp Glu Arg Asp Arg
        275                 280                 285

His Leu Ser Phe Ser Gly Ser Gly Ile Asp Asp Asp Glu Asp Phe Ile
    290                 295                 300

Ser Ser Thr Ile Ser Thr Thr Pro Arg Ala Phe Asp His Thr Lys Gln
305                 310                 315                 320

Asn Gln Asp Trp Thr Gln Trp Asn Pro Ser His Ser Asn Pro Glu Val
                325                 330                 335

Leu Leu Gln Thr Thr Thr Arg Met Thr Asp Val Asp Arg Asn Gly Thr
            340                 345                 350

Thr Ala Tyr Glu Gly Asn Trp Asn Pro Glu Ala His Pro Pro Leu Ile
        355                 360                 365

His His Glu His His Glu Glu Glu Thr Pro His Ser Thr Ser Thr
    370                 375                 380

Ile Gln Ala Thr Pro Ser Ser Thr Thr Glu Glu Thr Ala Thr Gln Lys
385                 390                 395                 400

Glu Gln Trp Phe Gly Asn Arg Trp His Glu Gly Tyr Arg Gln Thr Pro

```
            405                 410                 415
Lys Glu Asp Ser His Ser Thr Thr Gly Thr Ala Ala Ser Ala His
            420                 425             430

Thr Ser His Pro Met Gln Gly Arg Thr Thr Pro Ser Pro Glu Asp Ser
        435                 440                 445

Ser Trp Thr Asp Phe Phe Asn Pro Ile Ser His Pro Met Gly Arg Gly
    450                 455                 460

His Gln Ala Gly Arg Arg Met Asp Met Asp Ser Ser His Ser Ile Thr
465                 470                 475                 480

Leu Gln Pro Thr Ala Asn Pro Asn Thr Gly Leu Val Glu Asp Leu Asp
                485                 490                 495

Arg Thr Gly Pro Leu Ser Met Thr Thr Gln Gln Ser Asn Ser Gln Ser
            500                 505                 510

Phe Ser Thr Ser His Glu Gly Leu Glu Glu Asp Lys Asp His Pro Thr
        515                 520                 525

Thr Ser Thr Leu Thr Ser Ser Asn Arg Asn Asp Val Thr Gly Gly Arg
    530                 535                 540

Arg Asp Pro Asn His Ser Glu Gly Ser Thr Thr Leu Leu Glu Gly Tyr
545                 550                 555                 560

Thr Ser His Tyr Pro His Thr Lys Glu Ser Arg Thr Phe Ile Pro Val
                565                 570                 575

Thr Ser Ala Lys Thr Gly Ser Phe Gly Val Thr Ala Val Thr Val Gly
            580                 585                 590

Asp Ser Asn Ser Asn Val Asn Arg Ser Leu Ser Gly Asp Gln Asp Thr
        595                 600                 605

Phe His Pro Ser Gly Gly Ser His Thr Thr His Gly Ser Glu Ser Asp
    610                 615                 620

Gly His Ser His Gly Ser Gln Glu Gly Gly Ala Asn Thr Thr Ser Gly
625                 630                 635                 640

Pro Ile Arg Thr Pro Gln Ile Pro Glu Trp Leu Ile Ile Leu Ala Ser
                645                 650                 655

Leu Leu Ala Leu Ala Leu Ile Leu Ala Val Cys Ile Ala Val Asn Ser
            660                 665                 670

Arg Arg Arg Cys Gly Gln Lys Lys Lys Leu Val Ile Asn Ser Gly Asn
        675                 680                 685

Gly Ala Val Glu Asp Arg Lys Pro Ser Gly Leu Asn Gly Glu Ala Ser
    690                 695                 700

Lys Ser Gln Glu Met Val His Leu Val Asn Lys Glu Ser Ser Glu Thr
705                 710                 715                 720

Pro Asp Gln Phe Met Thr Ala Asp Glu Thr Arg Asn Leu Gln Asn Val
                725                 730                 735

Asp Met Lys Ile Gly Val
                740

<210> SEQ ID NO 19
<211> LENGTH: 2229
<212> TYPE: DNA
<213> ORGANISM: Homo sapiens

<400> SEQUENCE: 19
atggacaagt tttggtggca cgcagcctgg ggactctgcc tcgtgccgct gagcctggcg      60
cagatcgatt tgaatataac ctgccgcttt gcaggtgtat tccacgtgga gaaaaatggt     120
cgctacagca tctctcggac ggaggccgct gacctctgca aggctttcaa tagcaccttg     180
```

| | |
|---|---|
| cccacaatgg cccagatgga gaaagctctg agcatcggat ttgagacctg caggtatggg | 240 |
| ttcatagaag ggcacgtggt gattccccgg atccacccca actccatctg tgcagcaaac | 300 |
| aacacagggg tgtacatcct cacatccaac acctcccagt atgacacata ttgcttcaat | 360 |
| gcttcagctc cacctgaaga agattgtaca tcagtcacag acctgcccaa tgcctttgat | 420 |
| ggaccaatta ccataactat tgttaaccgt gatggcaccc gctatgtcca gaaaggagaa | 480 |
| tacagaacga atcctgaaga catctacccc agcaacccta ctgatgatga cgtgagcagc | 540 |
| ggctcctcca gtgaaaggag cagcacttca ggaggttaca tcttttacac cttttctact | 600 |
| gtacacccca tcccagacga agacagtccc tggatcaccg acagcacaga cagaatccct | 660 |
| gctaccactt tgatgagcac tagtgctaca gcaactgaga cagcaaccaa gaggcaagaa | 720 |
| acctgggatt ggttttcatg gttgtttcta ccatcagagt caagaatca tcttcacaca | 780 |
| acaacacaaa tggctggtac gtcttcaaat accatctcag caggctggga gccaaatgaa | 840 |
| gaaaatgaag atgaaagaga cagacacctc agtttttctg atcaggcat tgatgatgat | 900 |
| gaagatttta tctccagcac catttcaacc accacgggg cttttgacca cacaaaacag | 960 |
| aaccaggact ggacccagtg gaacccaagc cattcaaatc cggaagtgct acttcagaca | 1020 |
| accacaagga tgactgatgt agacagaaat ggcaccactg cttatgaagg aaactggaac | 1080 |
| ccagaagcac accctcccct cattcaccat gagcatcatg aggaagaaga gaccccacat | 1140 |
| tctacaagca caatccaggc aactcctagt agtacaacgg aagaaacagc tacccagaag | 1200 |
| gaacagtggt ttggcaacag atggcatgag ggatatcgcc aaacacccaa agaagactcc | 1260 |
| cattcgacaa cagggacagc tgcagcctca gctcatacca gcatccaat gcaaggaagg | 1320 |
| acaacaccaa gcccagagga cagttcctgg actgatttct tcaacccaat ctcacacccc | 1380 |
| atgggacgag tcatcaagc aggaagaagg atggatatgg actccagtca tagtataacg | 1440 |
| cttcagccta ctgcaaatcc aaacacaggt ttggtggaag atttggacag gacaggacct | 1500 |
| cttttcaatga caacgcagca gagtaattct cagagcttct ctacatcaca tgaaggcttg | 1560 |
| gaagaagata agaccatcc aacaacttct actctgacat caagcaatag gaatgatgtc | 1620 |
| acaggtggaa gaagaccc aaatcattct gaaggctcaa ctactttact ggaaggttat | 1680 |
| acctctcatt acccacacac gaaggaaagc aggaccttca tcccagtgac ctcagctaag | 1740 |
| actgggtcct ttgagttac tgcagttact gttggagatt ccaactctaa tgtcaatcgt | 1800 |
| tccttatcag gagaccaaga cacattccac cccagtgggg ggtcccatac cactcatgga | 1860 |
| tctgaatcag atggacactc acatgggagt caagaaggtg gagcaaacac aacctctggt | 1920 |
| cctataagga caccccaaat tccagaatgg ctgatcatct tggcatccct cttggccttg | 1980 |
| gctttgattc ttgcagtttg cattgcagtc aacagtcgaa gaaggtgtgg gcagaagaaa | 2040 |
| aagctagtga tcaacagtgg caatggagct gtggaggaca gaaagccaag tggactcaac | 2100 |
| ggagaggcca gcaagtctca ggaaatggtg catttggtga acaaggagtc gtcagaaact | 2160 |
| ccagaccagt ttatgacagc tgatgagaca aggaacctgc agaatgtgga catgaagatt | 2220 |
| ggggtgtaa | 2229 |

<210> SEQ ID NO 20
<211> LENGTH: 3275
<212> TYPE: DNA
<213> ORGANISM: Homo sapiens

<400> SEQUENCE: 20

| | |
|---|---|
| gaagtcaaga cgtctggaaa gaattaccca gtcctggctt cgagcagccc attgaaccag | 60 |

```
agacttgaaa cagccccagc caaagacttt tctcccaatt ctgcgcttcc tgggttctgc    120
tgagtcttcc acaggctttt ttttttttt ttttttttt taagacgaaa aagagatttt      180
ctgttatcgg gggcagaaag actgaagccc aaaaaaaaaa aaaaaaaaaa aagaaaagaa    240
aagaaaaaag aaaagttaat ttatttttaa agcataattt ttttaagaat tagactgaag    300
tgcaacggaa acataaagag aatattagtg aaattatttt ttaaagtggg gaagaatcaa    360
acatttaaga ctcccctatc cttttttaaat gttgttttta aatttcttat tttttttggc   420
cggtcgtctc aaattcatct gatctcttat tacctcaatt ttggaaactg cccgccaccg    480
accctccggg accacacaga caggctgagg acgactttat gaccaagagc tgaacaagat    540
gcattgtgag aggtttctat gtatcctgag aataattgga accacactct ttggagtctc    600
tctcctcctt ggaatcacag ctgcttatat tgttggctac cagtttatcc aaacggataa    660
ttactatttc tcttttggac tgtatggtgc cttttttggca tcacacctca tcatccaaag   720 cctgttttgcc ttttttggagc accgaaaaat gaaaaaatcc ctagaaaccc ccataaagtt  780
gaacaaaaca gttgcccttt gcatcgctgc ctatcaagaa gatccagact acttaaggaa    840
atgtttgcaa tctgtgaaaa ggctaaccta ccctgggatt aaagttgtca tggtcatga    900 tgggaactca gaagatgacc tttacatgat ggacatcttc agtgaagtca tgggcagaga    960
caaatcagcc acttatatct ggaagaacaa cttccacgaa aagggtcccg gtgagacaga    1020
tgagtcacat aaagaaagct cgcaacacgt aacgcaattg gtcttgtcca caaaagtat    1080 ctgcatcatg caaaatgggg gtggaaaaag agaagtcatg tacacagcct tcagagcact    1140
gggacgaagt gtggattatg tacaggtttg tgattcagac actatgcttg acccagcctc    1200
atctgtggag atggtaaaag ttttagaaga agatcccatg gttggaggtg ttgggggaga    1260
tgtccagatt ttaaacaagt acgattcctg gatctcattc ctcagcagtg taagatattg    1320
gatggctttt aatatagaaa gggcctgtca gtcttatttt gggtgtgttc agtgcattag    1380
tggacctctg ggaatgtaca gaaactcctt gttgcatgag tttgtggaag attggtacaa    1440
tcaagaattt atgggcaacc aatgtagctt tggtgatgac aggcatctca cgaaccgggt    1500
gctgagcctg ggctatgcaa caaaatacac agctcgatct aagtgcctta ctgaaacacc    1560
tatagaatat ctcagatggc taaaccagca gacccgttgg agcaagtcct acttccgaga    1620
atggctgtac aatgcaatgt ggtttcacaa acatcacttg tggatgacct acgaagcgat    1680
tatcactgga ttcttttcctt tcttttctcat tgccacagta atccagctct ctaccggggg   1740
taaaatttgg aacattctcc tcttcttgtt aactgtccag ctagtaggtc tcataaaatc     1800
atcttttgcc agctgcctta gaggaaatat cgtcatggtc ttcatgtctc tctactcagt     1860
gttatacatg tcgagtttac ttcccgccaa gatgtttgca attgcaacaa taaacaaagc     1920
tgggtggggc acatcaggaa ggaaaaccat tgttgttaat ttcataggac tcattccagt     1980
atcagtttgg tttacaatcc tcctgggtgg tgtgattttc accatttata aggagtctaa     2040
aaggccattt tcagaatcca aacagacagt tctaattgtt ggaacgttgc tctatgcatg     2100
ctattgggtc atgcttttga cgctgtatgt agttctcatc aataagtgtg caggcggaa     2160 gaagggacaa caatatgaca tggtgcttga tgtatgatct tccatgtttt gacgtttgca     2220
gtcacacaca acaccttagt tcctctaggg gctgtacagt attgtggcat cagataatgc    2280
caccaaagga gacatatcac tgctgctggg acttgaacaa agacatttat atgggtttat    2340
tttcattctg ccaaagtaaa acaatacatc aacaagaaga aactcagatt taacctgtta   2400
```

```
tttctatgaa aatgggatga attctttgtt tatgcacttt ttccttactg tgcatccgcc    2460
tgaaagtgtt ttgccctata tacctcacta gccatgcttt atgtgggtta tcatggaaga    2520
aaaggatttt ggaaactcaa ggaaaagttc tttcaaccta tacaacctaa cttatggact    2580
gttttgatag atgataattt ttttttttta ggaaggattt tcttttaac tttaccaaat     2640 gaaatgccaa aggaagtttt aaaggccgtt ggctgtgctg tattttgata taattgtact    2700 gtgttttaa attttgtatg ccaatcttaa agacaaattt tgcatattct ctattttact    2760
tttctgccaa aataaacctg ttcttccttt tttaaaataa aataagttct taaaaaattt    2820
atacttaaaa aatcctgccc aaaatgtgaa gcttggttga ctgatgttca tgatagaaag    2880
aataaaatgt ttctctctct ctaccttta aaattgaata gtttatttct gtgaaagaag    2940
tatttaaact ttcaatattt taactttttg tttttatttc ttttagaaaa ggccaatata    3000
cctatcacac tttggaagta aaaatacaca ctttcgtgtg tacctaaaaa aaaaatcgtt   3060
gaaaatcaag gccaaggta gtgcaattt ttcattaaga tttaaaaaaa agggaatgat     3120
agtctttgaa agaaaacagt aggcatccag cactggacaa aacatgggta tcaaagatga    3180
ataatctttg gagattctgg cagtgttttc ccagaacaag tcaagtggaa agtggagaaa    3240
ttatctgtat aattttggac acatacaatg cagtt                              3275
```

COMPOSITIONS AND METHODS FOR THE TREATMENT OF TISSUE FIBROSIS

CROSS-REFERENCE TO RELATED APPLICATIONS

This patent application is a national stage filing under 35 U.S.C. 371 of International Patent Application No. PCT/US2012/033246, filed on Apr. 12, 2012, which claims the benefit of priority to U.S. Provisional Patent Application No. 61/474,718, filed on Apr. 12, 2011, and U.S. Provisional Patent Application No. 61/486,292, filed on May 15, 2011, the disclosures of each of which are incorporated by reference herein in their entireties.

STATEMENT REGARDING FEDERALLY SPONSORED RESEARCH

The research detailed in this disclosure was supported by government funding under federal grant number R01HL060539 from the NIH, and federal grant number R01A1052201 from the NIH. The U.S. government may have certain rights to this invention.

A sequence listing is filed with the application in electronic format and is incorporated by reference herein. The sequence listing text file "028193.9120.WO00_SeqList" was created on Apr. 12, 2012, and is 19,239 bytes in size.

BACKGROUND

Progressive tissue fibrosis is a major cause of morbidity and mortality. Tissue fibrosis is the formation of excess fibrous connective tissue in an organ or tissue in a reparative or reactive process, which is different from the formation of fibrous tissue as a normal constituent of an organ or tissue. Scarring is confluent fibrosis that obliterates the architecture of the underlying organ or tissue. Pulmonary fibrosis is the formation or development of excess fibrous connective tissue in the lungs. Idiopathic pulmonary fibrosis (IPF) is a terminal illness characterized by progressive and unremitting matrix deposition in the interstitium of the lung. The clinical course of IPF is unrelenting and has characteristics reminiscent of cancer. IPF patients suffer from the inexorable accumulation of extracellular matrix in the gas-exchanging regions of the lung. One feature of IPF is the formation of fibroblastic foci, which are structures of accumulated myofibroblasts in the interstitium of the lung juxtaposed to the alveolar epithelium and are associated with destruction of the adjoining alveolar basement membrane.

Hyaluronan (HA) is a non-sulfated glycosaminoglycan produced by mesenchymal cells as well as a variety of tumor cells. CD44 is a cell surface receptor for HA and plays a role in inflammatory cell recruitment and activation, as well as tumor growth and metastasis.

While numerous mediators have been identified as initiating tissue fibrosis, the mechanisms that contribute to persistent fibrodestructive disease remain incompletely understood.

SUMMARY

In an aspect the disclosure relates to methods of treating pulmonary fibrosis comprising administering to a subject in need of treatment an effective amount of an agent that inhibits a hyaluron synthase (HAS) or CD44.

In another aspect, the disclosure relates to methods of inhibiting myofibroblast invasion comprising administering to a subject in need of treatment an effective amount of an agent that inhibits a hyaluron synthase (HAS) or CD44.

In another aspect, the disclosure relates to methods of reducing matrix deposition in the lung comprising administering to a subject in need of treatment an effective amount of an agent that inhibits a hyaluron synthase (HAS) or CD44.

In another aspect, the disclosure relates to methods of determining the progression of pulmonary fibrosis comprising determining the level of matrix metalloproteinase expression in a cell, and comparing the level of expression to that of a control cell, wherein an increased level of expression relative to the control cell indicates progression of the disease.

In another aspect, the disclosure relates to methods of determining the progression of pulmonary fibrosis comprising determining the level of metalloproteinase tissue inhibitor expression in a cell, and comparing the level of expression to that of a control cell, wherein a decreased level of expression relative to the control cell indicates progression of the disease.

The disclosure relates to other aspects and embodiments which will become apparent in view of the description and accompanying drawings.

DETAILED DESCRIPTION

Figure 1:
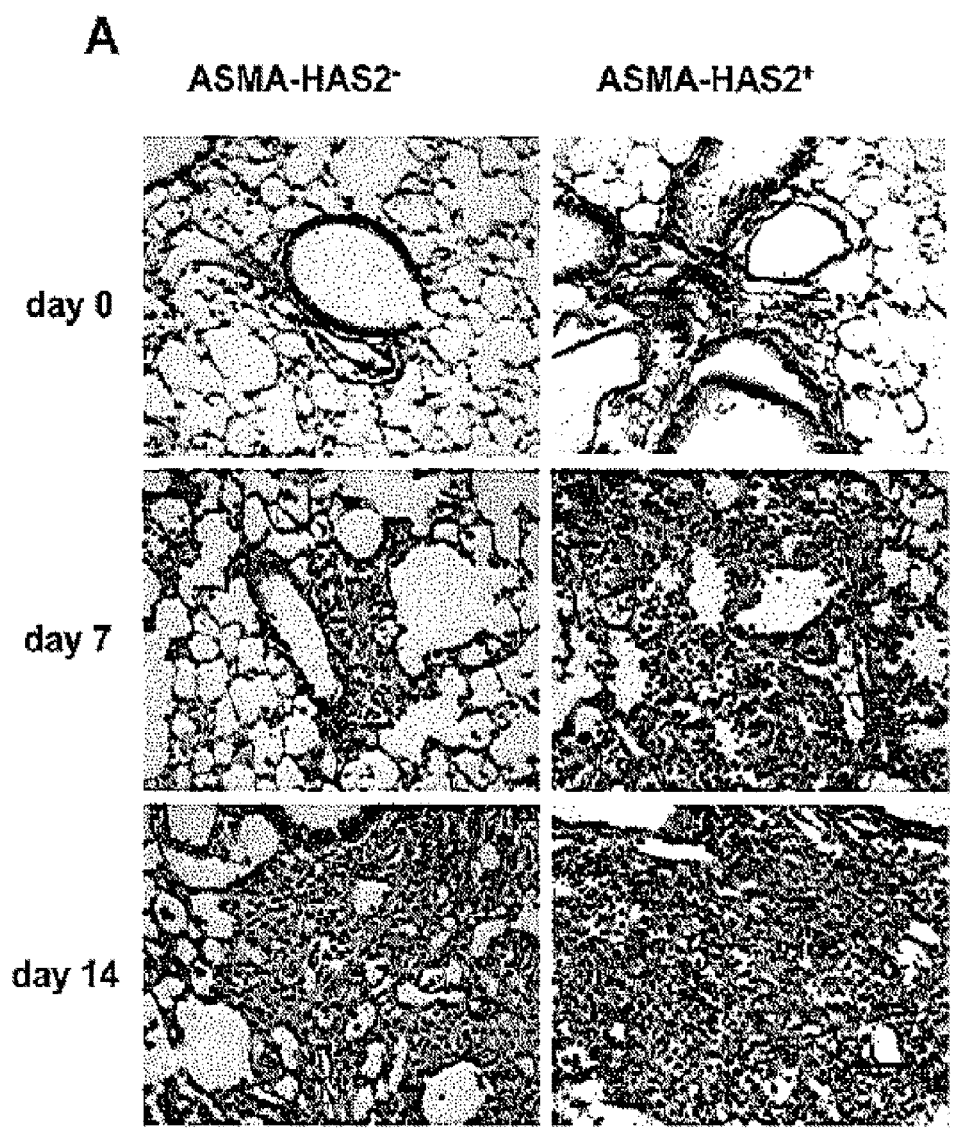
FIG. 1 shows ASMA-HAS2 transgenic mice accumulate HA and show increased mortality following bleomycin challenging. (A) Distribution of HA in lungs of ASMA-HAS2$^+$ and littermate control mice (ASMA-HAS2$^-$) as determined by immunohistochemical staining HA with biotin-HABP. Representative sections from 5 bleomycin-treated samples and 3 controls are shown. Scale bars, 50 µm. (B, C) HA concentration in lung tissue (B) and bronchoalveolar lavage fluid (BALF) (C) from ASMA-HAS2$^+$ mice and control mice (ASMA-HAS2$^-$) at different times after bleomycin treatment (n=5-7, *$p<0.05$, $p<0.01$ by 2-way ANOVA with Bonferroni post test). The experiments were performed three times, (D, E) Murine HAS2 (mHAS2) (D, E) and human HAS2 (hHAS2) (E) mRNA expression levels in ASMA-HAS2$^+$ mice and controls (ASMA-HAS2$^-$) at various time points after bleomycin treatment were measured using real-time peR (n=3-5, $p<0.01$, ***$p<0.001$). The experiments were performed three times. (F) Increased mortality was observed in ASMA-HAS2$^+$ mice compared with their littermate controls (ASMA-HAS2$^-$) following bleomycin-induced lung injury.
Figure 1:
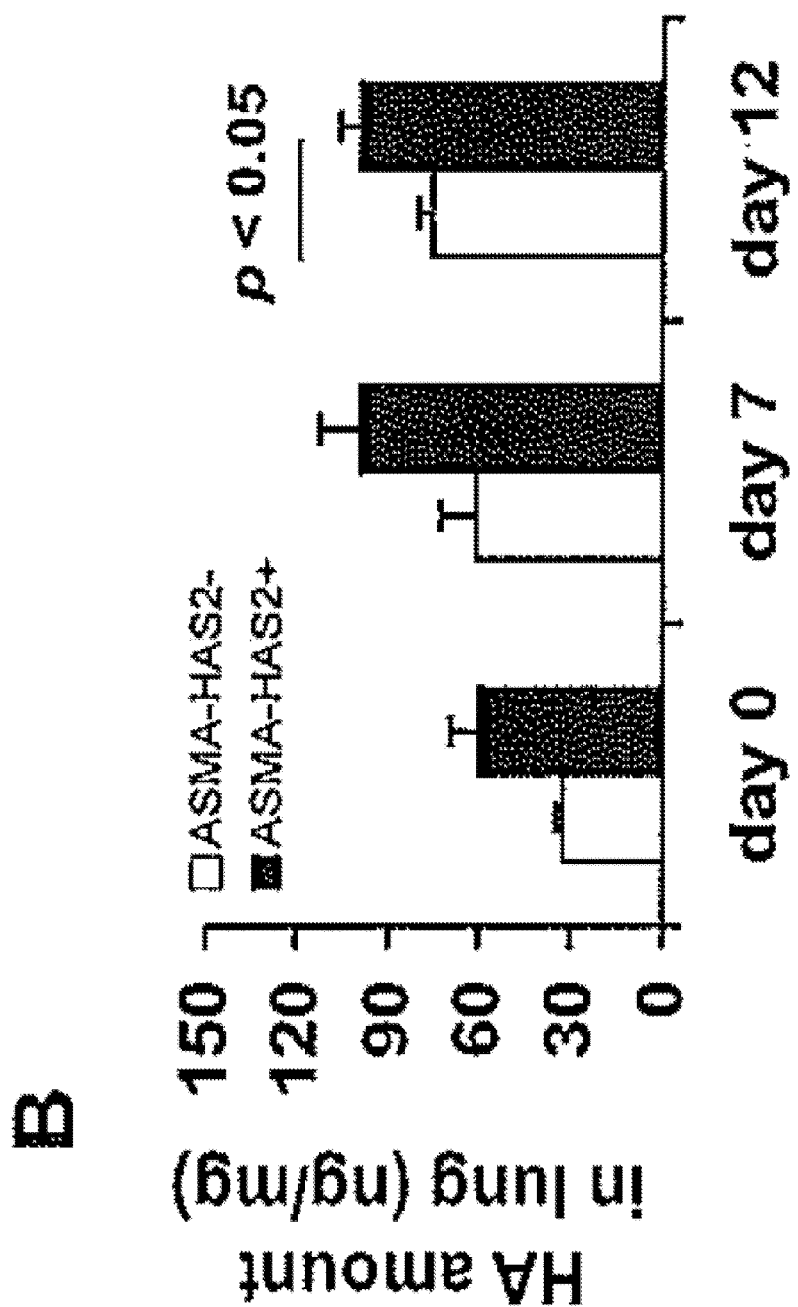
Figure 1:
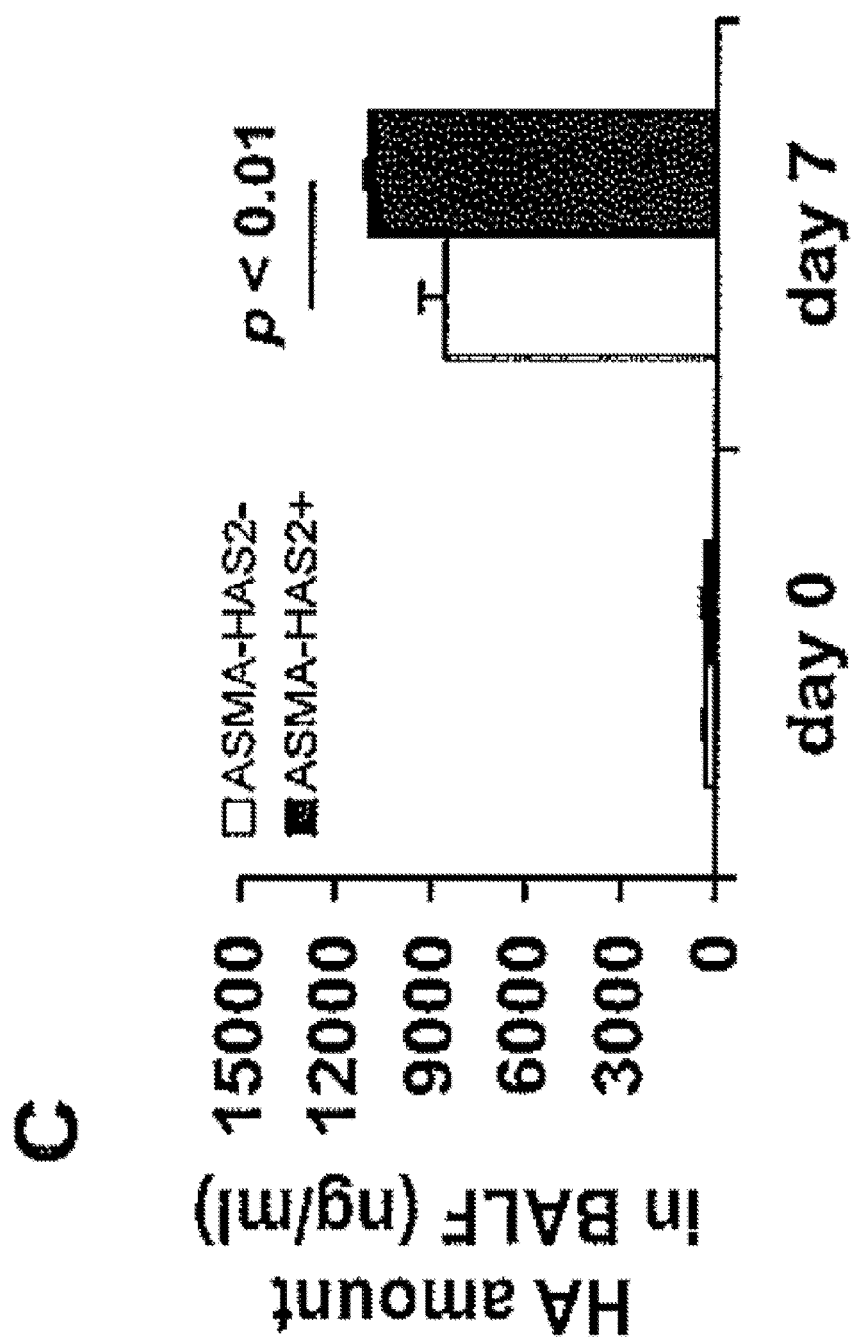
Figure 1:
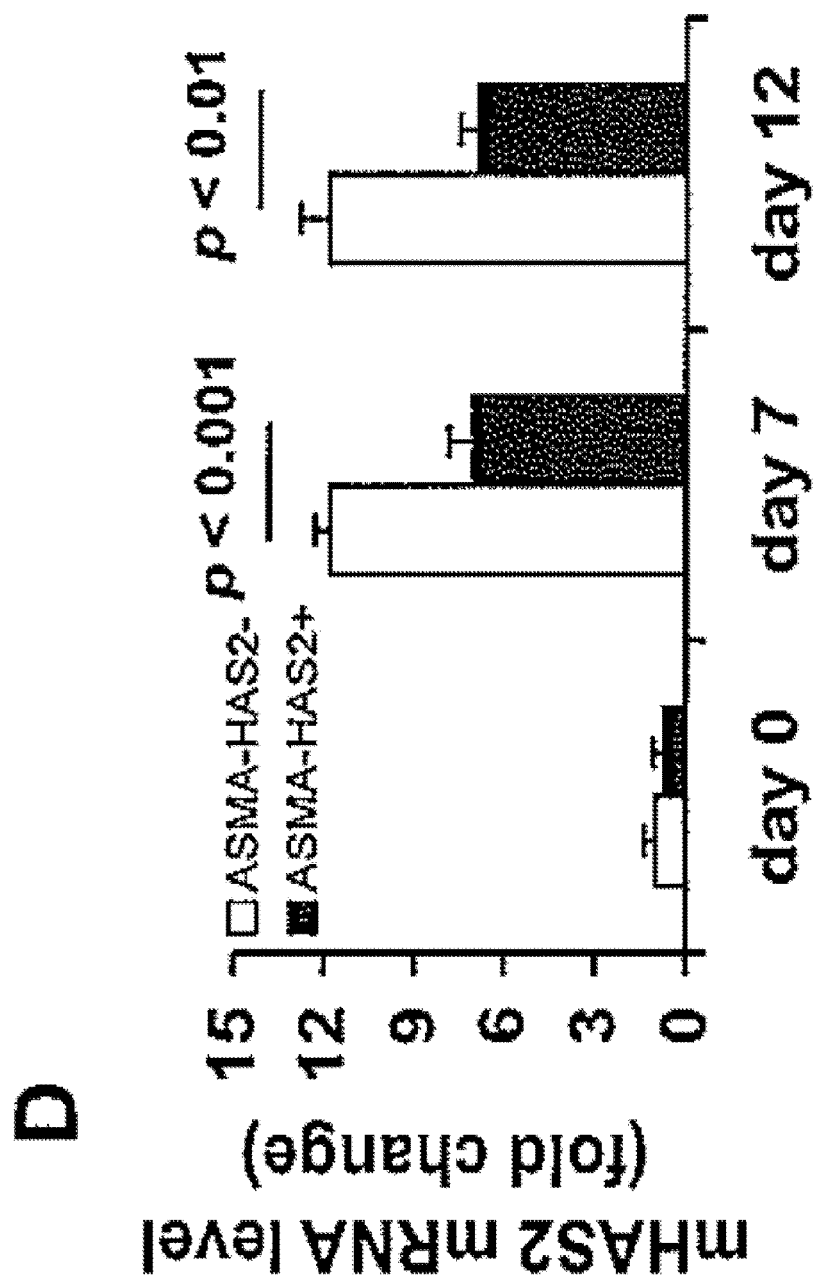
Figure 1:
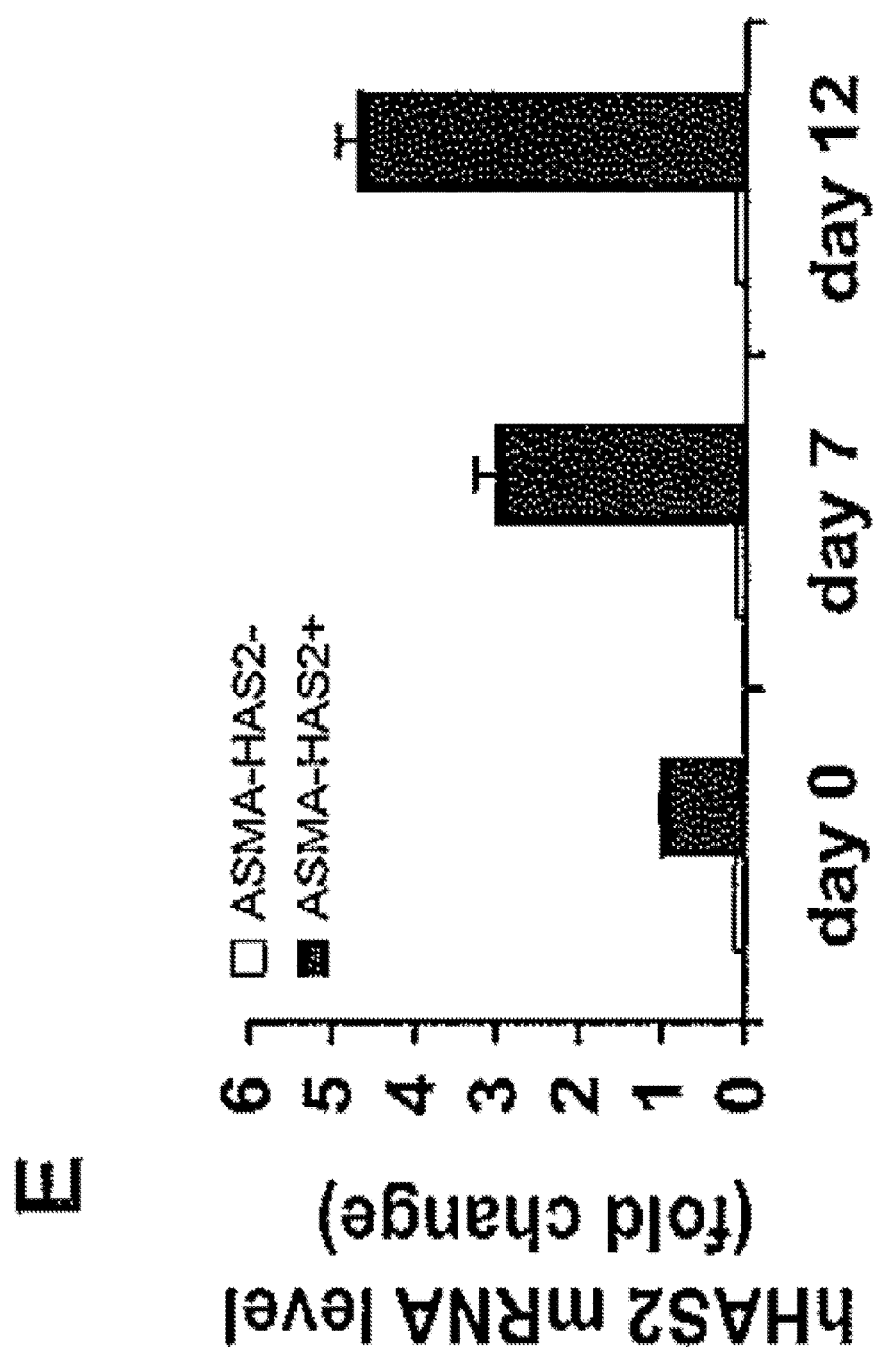
Figure 1:
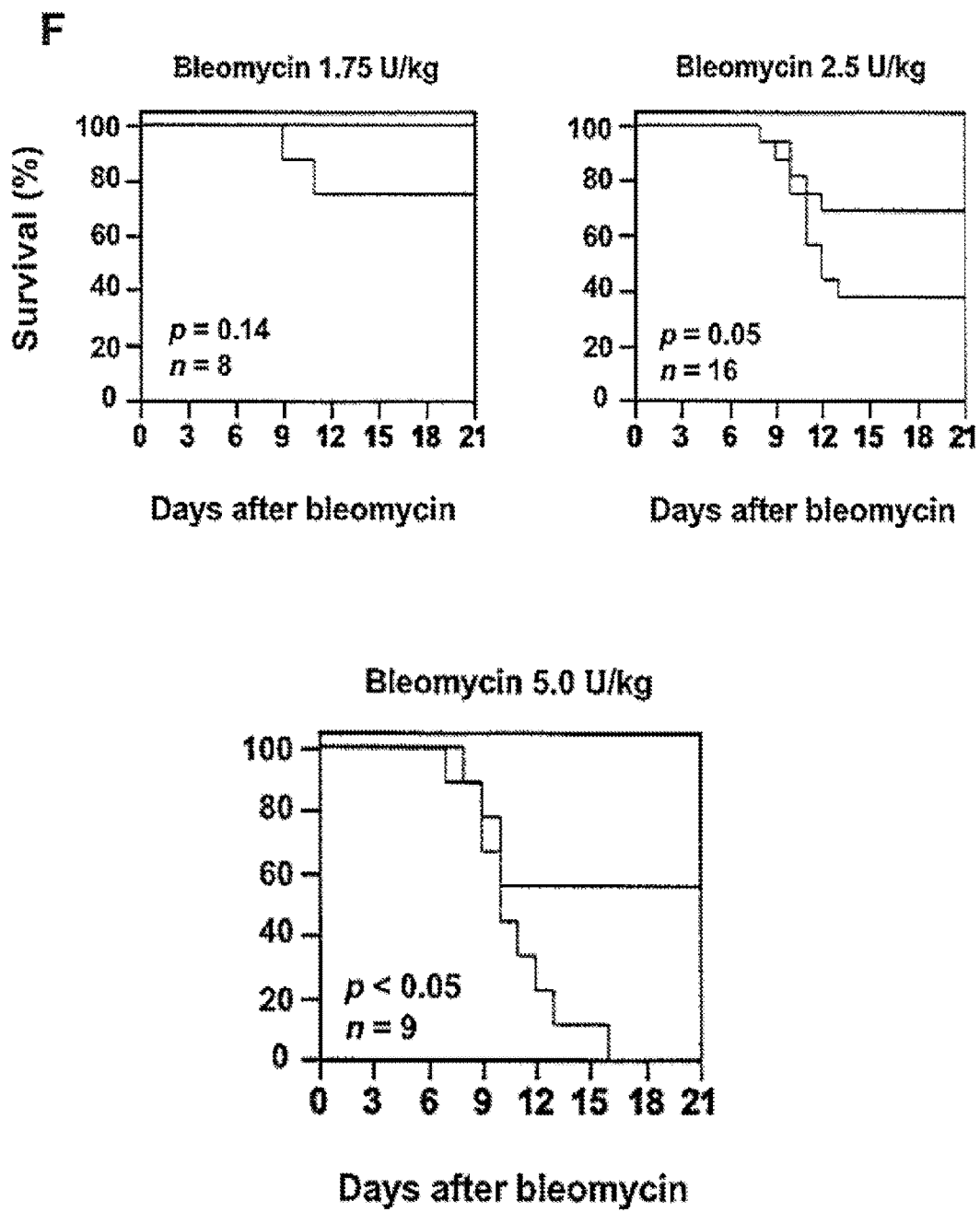

Before any aspects and embodiments are described in detail, it is to be understood that the claims are not limited to the details of construction and the arrangement of components set forth in the following description or illustrated in the drawings.

Myofibroblasts accumulate at sites of tissue remodeling and produce extracellular matrix components such as collagen and hyaluronan that can compromise organ function. The inventors have identified several targets for the therapeutic intervention of disorders and diseases that are associated with tissue fibrosis, invasive fibroblast phenotypes, and other similar disorders. As disclosed in further detail herein, targeted overexpression of a hyaluronan synthase (HAS) in myofibroblasts produced an aggressive phenotype leading to severe lung fibrosis and death following injury. By way of illustration the Examples disclose that fibroblasts isolated from transgenic mice overexpressing a HAS showed capacity to invade matrix. The disclosure also describes that conditional deletion of a HAS in mesenchymal cells abrogates an invasive fibroblast phenotype, impeded myofibroblast accumulation, and inhibited the development of lung fibrosis. Further, the disclosure describes that both the invasive phenotype and the progressive fibrosis are inhibited in the absence of CD44. As illustrated in the Examples, treatment with a blocking antibody to CD44 reduced lung fibrosis in mice in vivo, and fibroblasts isolated from patients with idiopathic pulmonary fibrosis (IDF) exhibited an invasive phenotype that was also dependent on activity of HAS2 and CD44.

In an aspect, the disclosure provides a method of treating tissue fibrosis comprising administering to a subject in need of treatment an effective amount of an agent that inhibits a hyaluron synthase (HAS) or CD44, or both a HAS and CD44. Embodiments of the method provide for the inhibition of HAS, wherein HAS may include at least one of HAS1, HAS2, and HAS3, or a combination thereof. In embodiments the HAS and/or CD44 may be mammalian such as, for example, a rodent (e.g. a guinea pig, a hamster, a rat, a mouse), canine (e.g. a dog), feline (e.g. a cat), equine (e.g. a horse), a primate (e.g. a monkey, ape, marmoset, baboon, gorilla, chimpanzee, orangutan, gibbon), or a human. In some embodiments HAS is human and can comprise, for example, a HAS2 polypeptide of SEQ ID NO: 16, or a polynucleotide encoding the polypeptide such as, for example, a HAS2 polynucleotide of SEQ ID NO: 17, described by GenBank Accession Nos: AAC50692 and CCDS6335.1. Suitably, the agent may inhibit HAS2. Embodiments of the method also provide for the inhibition of CD44, wherein the CD44 is a mammalian CD44. In some embodiments, CD44 is human and may comprise, for example, a CD44 polypeptide of SEQ ID NO: 18, or a polynucleotide encoding the polypeptide such as, for example, a CD44 polynucleotide of SEQ ID NO: 19 described by GenBank Accession Nos: NM_000610 and CCDS7897.1.

"Tissue fibrosis" relates to the formation of excess fibrous connective tissue in an organ or tissue in a reparative or reactive process. Thus, tissue fibrosis can be associated disorders and diseases of organs and tissues such as, for example, pulmonary fibrosis, (e.g., idiopathic pulmonary fibrosis); cirrhosis (liver); endomyocardial fibrosis (heart); mediastinal fibrosis (soft tissue of the mediastinum); myelofibrosis (bone marrow); retroperitoneal fibrosis (soft tissue of the retroperitoneum); progressive massive fibrosis (lungs); nephrogenic systemic fibrosis (skin); Crohn's Disease (intestine); keloid (skin); myocardial infarction (heart); scleroderma/systemic sclerosis (skin, lungs); arthrofibrosis (knee, shoulder, other joints); some forms of adhesive capsulitis (shoulder); and the like. In some embodiments the treatment of tissue fibrosis can comprise the treatment of fibrosis associated with pulmonary (lung) tissue such as idiopathic pulmonary fibrosis (IPF).

In certain aspects, the disclosure provides methods of inhibiting myofibroblast invasion. The methods may comprise administering to a subject in need of treatment an effective amount of an agent that inhibits a HAS or CD44, or combination thereof. In some embodiments myofibroblast invasion includes involvement, association, or promotion of neoplastic growth such as, for example, various tumors and/or cancers.

In certain aspects, the disclosure provides methods of reducing matrix deposition in tissue. The methods may comprise administering to a subject in need of treatment an effective amount of an agent that inhibits a HAS or CD44, or a combination thereof. In embodiments, tissue may include lung, heart, liver, skin, bone marrow, intestine, or other tissue in the body.

In aspects disclosed herein that relate to methods and assays an active agent suitably inhibits as least one of HAS or CD44, or both HAS and CD44. Embodiments provide for an active agent that can inhibit biological function of a HAS enzyme or a CD44 receptor protein. Other embodiments provide for an active agent that may inhibit the expression of mRNA encoding HAS and/or CD44. Some embodiments provide an active agent that may inhibit the translation of mRNA encoding HAS and/or CD44 to protein. Thus, an active agent may indirectly or directly bind and inhibit the activity of HAS or CD44 (e.g., binding activity or enzymatic activity), reduce the expression of HAS or CD44, prevent expression of HAS or CD44, or inhibit the production of HAS or CD44 in a cell.

In some embodiments, an active agent can increase the amount of, or the biological activity of a protein that can reduce the activity of HAS or CD44. Agents capable of increasing the level of a protein may include any agent capable of increasing protein or mRNA levels or increasing the expression of the protein. In one embodiment, the agent may comprise the protein itself. For example, the agent may include exogenously expressed and isolated protein capable of being delivered to the cells. The protein may be delivered to cells by a variety of methods, including fusion to Tat or VP16 or via a delivery vehicle, such as a liposome, all of which allow delivery of protein based agents across the cellular membrane. Those of skill in the art will appreciate that other delivery mechanisms for proteins may be used. Alternatively, mRNA expression may be enhanced relative to control cells by contact with the agent. For example, the agent capable of increasing the level of natively expressed protein may include a gene expression activator or de-repressor. The agent capable of increasing the level of protein may also include agents that bind to directly or indirectly and increase the effective level of protein, for example, by enhancing the binding or other activity of the protein.

The amount or level of expression of a biomolecule (e.g., mRNA or protein) in a cell may be evaluated by any variety of techniques that are known in the art. Thus, inhibit or inhibiting, such as, for example, the level of protein expression (e.g., HAS or CD44), may be evaluated at either the protein or mRNA level using techniques including, but not limited to, Western blot, ELISA, Northern blot, real time PCR, immunofluorescence, or FACS analysis. For example, the expression level of a protein may be evaluated by immunofluorescence by visualizing cells stained with a fluorescently-labeled protein-specific antibody, Western blot analysis of protein expression, and RT-PCR of protein transcripts. Inhibit or inhibiting relates to any measurable reduction or attenuation of amounts or activity, e.g., amounts or activity of HAS or CD44 or myofibroblast invasion. The expression level of HAS or CD44 may be compared to a control. A control may include comparison to the level of expression in a control cell, such as a non-cancerous cell, a non-fibrotic cell, or other normal cell. Alternatively a control may include an average range of the level of expression from a population of normal cells. Alternatively, a standard value developed by analyzing the results of a population of cells with known responses to therapies or agents may be used. Those skilled in the art will appreciate that a variety of controls may be used.

An agent may comprise a variety of compounds and compositions and agents. For example, the agent may comprise a biological molecule, including nucleic acid molecules, such as a polynucleotide having RNAi activity against HASs or a substrate thereof. In embodiments, the nucleic acid molecules can include decoy RNAs, dsRNAs, miRNAs, siRNAs, nucleic acid aptamers, antisense nucleic acid molecules, and enzymatic nucleic acid molecules that comprise a sequence that is sufficient allow for binding to an encoding nucleic acid sequence and inhibit activity thereof (i.e., are complementary to such encoding nucleic acid sequences). Suitably, an RNAi molecule comprises sequence that is complementary to at least a portion of a target sequence such that the RNAi can hybridize to the target sequence under physiological or artificially defined (e.g., reaction) conditions. In some embodiments an RNAi molecule comprises sequence that is complementary such that the molecule can hybridize to a target sequence under moderate or high stringency conditions, which are well known and can be determined by one of skill in the art. In some embodiments an RNAi molecule has complete (100%) complementarity over its entire length to a target sequence. A variety of RNAi molecules are known in the art, and can include chemical modifications, such as modifications to the sugar-phosphate backbone or nucleobase that are known in the art. The modifications may be selected by one of skill in the art to alter activity, binding, immune response, or other properties. In some embodiments, the RNAi can comprise an siRNA having a length from about 18 to about 24 nucleotides.

In some embodiments, the inhibitory nucleic acid molecule can bind to a target nucleic acid sequence under stringent binding conditions. The terms "stringent conditions" or "stringent hybridization conditions" includes reference to conditions under which a polynucleotide will hybridize to its target sequence, to a detectably greater degree than other sequences (e.g., at least 2-fold over background). An example of stringent conditions include those in which hybridization in 50% formamide, 1 M NaCl, 1% SDS at 37° C., and a wash in 0.1×SSC at 60 to 65° C. is performed. Amino acid and polynucleotide identity, homology and/or similarity can be determined using the ClustalW algorithm, MEGALIGN™, Lasergene, Wis.) Given a target polynucleotide sequence, for example of HAS or CD44 or biological substrate thereof, an inhibitory nucleic acid molecule can be designed using motifs and targeted to a region that is anticipated to be effective for inhibitory activity, such as is known in the art.

In certain non-limiting embodiments, the agent may comprise siRNA targeted to a particular region of SEQ ID NO: 17, such as, for example, a siRNA targeting SEQ ID NO:15 (CAGCTCGATCTAAGTGCCTTA), which corresponds to nucleotides 1530-1550 of the HAS2 cDNA. Any variety of siRNA or inhibitory RNA molecules (e.g., RNA, mixed DNA/RNA, DNA, chemically modified DNA and/or RNA, etc.) can be designed using strategies known in the art or otherwise herein described.

In other embodiments, the inhibitor comprises an antibody that can specifically bind to a protein such as HAS or CD44 or a fragment thereof. Embodiments also provide for an antibody that inhibits HAS or CD44 through specific binding to a HAS and/or CD44 substrate molecule. The antibodies can be produced by any method known in the art, such as by immunization with a full-length protein such as HAS or CD44, or fragments thereof. The antibodies can be polyclonal or monoclonal, and/or may be recombinant antibodies. In embodiments, antibodies that are human antibodies can be prepared, for example, by immunization of transgenic animals capable of producing a human antibody (see, for example, International Patent Application, Publication WO 93/12227). Monoclonal antibodies (mAbs) can be produced by a variety of techniques, including conventional monoclonal antibody methodology, e.g., the standard somatic cell hybridization technique of Kohler and Milstein (see, for example, *Nature* 1975, 256, 495), and other techniques, e.g., viral or oncogenic transformation of B-lymphocytes. Animal systems for preparing hybridomas include mouse. Hybridoma production in the mouse is very well established, and immunization protocols and techniques for isolation of immunized splenocytes for fusion are well known in the art. Fusion partners (e.g., murine myeloma cells) and fusion procedures are also known.

In some embodiments, an antibody can be a commercially available or otherwise publicly accessible antibody to either HAS or CD44 such as, for example, an antibody comprising anti-mouse CD44 blocking antibody (KM201, available from ATCC, Manassa, Va.).

Any suitable methods can be used to evaluate a candidate active agent for inhibitory activity toward HAS or CD44. Such methods can include, for example, in vitro assays, in vitro cell-based assays, ex vivo assays, and in vivo methods. The methods can evaluate binding activity, or an activity downstream of the enzyme of interest. Ex vivo assays may involve treatment of cells with an agent of the invention, followed by detection of changes in transcription levels of certain genes, such as HAS or CD44 through collection of cellular RNA, conversion to cDNA, and quantification by quantitative real time polymerase chain reaction (RT-QPCR). Additionally, the cell viability, proliferation, and migration of cells may be determined after treatment with an agent. Suitable methods may further include matrigel invasion assays, HA pericellular coat determination, and microarray analysis.

"Administering" refers to administration of agents as needed to achieve a desired effect. Exemplary routes of administration include, but are not limited to, oral, rectal, nasal, sublingual, buccal, intramuscular, subcutaneous, intravenous, intracisternal, transdermal, intrameningeal, and parenteral administration. Such administration can be, in certain embodiments, by injection, inhalation, or implant.

Suitably the route of administration and dosage form of the preparation are selected to maximize the effect of the treatment. Typical examples of the administration route include oral routes as well as parenteral routes, including intracerebral, intracisternal, intraperitoneal, intraoral, intrathecal, intrabronchial, intrarectal, subcutaneous, intramuscular and intravenous routes. In some embodiments the therapeutic agent administered directly to a target site that is need of the treatment (e.g., at the site fibrosis or to the fibrotic tissue) such as, for example, administered to the target site by injection, catheter, incision or other suitable means. Typical examples of the dosage form include sprays, capsules, liposomes, tablets, granules, syrups, emulsions, suppositories, injections, ointments and tapes.

One skilled in the art can select an appropriate dosage and route of administration depending on the patient, the particular disease, disorder, or condition being treated, the duration of the treatment, concurrent therapies, etc. In certain embodiments, a dosage is selected that balances the effectiveness with the potential side effects, considering the severity of the disease, disorder, or condition (e.g., tissue fibrosis and/or associated clinical conditions).

For oral therapeutic administration, the composition may be combined with one or more carriers and used in the form of ingestible tablets, buccal tablets, troches, capsules, elixirs, suspensions, syrups, wafers, chewing gums, foods and the like. Such compositions and preparations should contain at least 0.1% of active compound. The percentage of the compositions and preparations may, of course, be varied and may conveniently be between about 0.1 to about 100% of the weight of a given unit dosage form. The amount of active compound in such therapeutically useful compositions is such that an effective dosage level will be obtained.

The tablets, troches, pills, capsules, and the like may also contain the following: binders such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen, or cherry flavoring. The above listing is merely representative and one skilled in the art could envision other binders, excipients, sweetening agents and the like. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac or sugar and the like.

The selected dosage level will depend upon a variety of factors including the activity of the particular compound employed, the route of administration, the time of administration, the rate of excretion or metabolism of the particular compound being employed, the duration of the treatment, other drugs, compounds and/or materials used in combination with the particular compound employed, the age, sex, weight, condition, general health and prior medical history of the patient being treated, and like factors well known in the medical arts.

In general, the daily dose contains from about 0.1 mg to about 2000 mg of the active ingredient, or about 0.5 to about 60 mg of the active ingredient. This dosage form permits the full daily dosage to be administered in one or two oral doses. More than once daily or twice daily administrations, e.g., 3, 4, 5 or 6 administrations per day, are also contemplated herein.

In some embodiments, as noted above, administering relates to providing an amount effective at bringing about a desired in vivo effect such as inhibition of HAS or CD44 in an animal, such as a human. As used herein, a "subject in need of treatment" refers to a subject having been diagnosed with tissue fibrosis and/or a disorder or a disease associated with tissue fibrosis, e.g., pulmonary fibrosis. A subject can also be one who has been determined as likely to develop tissue fibrosis such as, for example, a subject having a genetic disposition that is indicative of susceptibility of developing tissue fibrosis, or a subject in whose family the tissue fibrosis is more frequent than normal. A subject may be a mammalian subject. In embodiments a subject can include human and non-human animals. Exemplary human subjects include a human patient having tissue fibrosis or a disease or disorder associated with tissue fibrosis as described herein, or a normal subject. The term "non-human animals" includes all vertebrates, e.g., non-mammals (such as chickens, amphibians, reptiles) and mammals, such as non-human primates, domesticated and/or agriculturally useful animals (such as sheep, dogs, cats, cows, pigs, etc.), and rodents (such as mice, rats, hamsters, guinea pigs, etc.). Accordingly, embodiments of the methods described herein relate to treatment of a cell or tissue, a cell or tissue from a subject, or a subject that may be a eukaryote, an animal, a vertebrate animal, a mammal, a rodent (e.g. a guinea pig, a hamster, a rat, a mouse), murine (e.g. a mouse), canine (e.g. a dog), feline (e.g. a cat), equine (e.g. a horse), a primate, simian (e.g. a monkey or ape), a monkey (e.g. marmoset, baboon), an ape (e.g. gorilla, chimpanzee, orangutan, gibbon), or a human.

In some embodiments, provided are methods of treating a subject comprising administering an inhibitor of HAS or CD44 in a pharmaceutically acceptable composition.

"Pharmaceutically acceptable" means suitable for use in a human or other mammal. The terms "pharmaceutically acceptable carriers" and "pharmaceutically acceptable excipients" are used interchangeably and refer to substances that are useful for the preparation of a pharmaceutically acceptable composition. In certain embodiments, pharmaceutically acceptable carriers are generally compatible with the other ingredients of the composition, not deleterious to the recipient, and/or neither biologically nor otherwise undesirable.

Embodiments provide for pharmaceutically acceptable carriers including, but not limited to, substances useful for topical, intrathecal, ocular, parenteral, intravenous, intraperitoneal intramuscular, sublingual, nasal and oral administration. "Pharmaceutically acceptable carrier" also includes agents for preparation of aqueous dispersions and sterile powders for injection or dispersions. Examples of pharmaceutically acceptable carriers and excipients are discussed, e.g., in *Remington Pharmaceutical Science*, 16th Ed. Certain exemplary techniques and compositions for making dosage forms are described in the following references: *Modern Pharmaceutics*, Chapters 9 and 10, Banker & Rhodes, eds. (1979); Lieberman et al., *Pharmaceutical Dosage Forms: Tablets* (1981); and Ansel, *Introduction to Pharmaceutical Dosage Forms*, 2nd Ed., (1976).

In another aspect, the disclosure provides a method of determining the progression of tissue fibrosis in a biological sample. As used herein, the term "sample" or "biological sample" relates to any material that is taken from its native or natural state, so as to facilitate any desirable manipulation or further processing and/or modification. A sample or a biological sample can comprise a cell, a tissue, a fluid (e.g., a biological fluid), a protein (e.g., antibody, enzyme, soluble protein, insoluble protein), a polynucleotide (e.g., RNA, DNA), a membrane preparation, and the like, that can optionally be further isolated and/or purified from its native or natural state. A "biological fluid" refers to any a fluid originating from a biological organism. Exemplary biological fluids include, but are not limited to, blood, serum, plasma, lymph fluid, bile fluid, urine, saliva, mucus, sputum, tears, cerebrospinal fluid (CSF), bronchioalveolar lavage, nasopharyngeal lavage, rectal lavage, vaginal lavage, colonic lavage, nasal lavage, throat lavage, synovial fluid, semen, ascites fluid, pus, maternal milk, ear fluid, sweat, and amniotic fluid. A biological fluid may be in its natural state or in a modified state by the addition of components such as reagents, or removal of one or more natural constituents (e.g., blood plasma). In embodiments the method comprises determining the level of matrix metalloproteinase expression in a cell, and comparing the level of expression to that of a control cell, wherein an increased level of expression relative to the control cell indicates progression of the disease. In embodiments the method comprises determining the level of a metalloproteinase tissue inhibitor expression in a cell, and comparing the level of expression to that of a control cell, wherein a decreased level of expression relative to the control cell indicates progression of the disease. In some embodiments, the matrix metalloproteinase comprises MMP-12 or MMP1a, or a combination thereof. In some embodiments, the metalloproteinase tissue inhibitor may comprise Timp-3 or ADAMTS1, or a combination thereof.

In other embodiments, provided are methods of determining the progression of tissue fibrosis. The methods may comprise comprising determining the level of matrix metalloproteinase expression in a cell, and comparing the level of expression to that of a control cell, wherein an increased level of expression relative to the control cell indicates progression of the disease.

The use of the terms "a" and "an" and "the" and similar referents in the context of the disclosure are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. All methods described herein can be performed in any suitable order unless otherwise indicated herein or otherwise clearly contradicted by context. The use of any and all examples, or exemplary language (e.g., "such as") provided herein, is intended merely to illustrate aspects and embodiments of the disclosure and does not limit the scope of the claims. The use of the term "and/or" and similar referents in the context of the disclosure is to be construed to cover the terms surrounding the "and/or" in combination and in the alternative. For example, "HAS and/or CD44" is to be construed to cover "HAS" or "CD44" or the combination "HAS and CD44," unless otherwise indicated herein or clearly contradicted by the context.

The examples that follow provide further detailed description of some aspects and embodiments of the disclosure and are to be considered merely illustrative of optional ways in which these aspects and embodiments can be performed. Thus, these illustrative examples do not serve to limit to the claims.

EXAMPLES

Example 1. Materials and Methods

Mice

ASMA-human HAS2 transgenic mice (ASMA-HAS2$^+$) were used (Chai et al., 2005). The conditional Has2 null allele was generated using the Cre/loxP system. HAS2 protein is a multipass transmembrane protein. This conditional allele was designed in such a way that exon 2, which contains the start codon as well as two N-terminal transmembrane domains crucial for the insertion of HAS2 protein into the plasma membrane, was deleted upon Cre-mediated recombination, and thereby no HAS2 protein was produced. Has2$^{flox/+}$ designates the intact conditional allele prior to recombination. The Cre recombinase-expressing mice under the control of the collagen1α2 promoter and enhance (Colα2-iCre$^1$) were used (Florin et al., 2004). For the conditional deletion of HAS2, two chimeras of Has2$^{flox/+}$ mice were crossbred to obtain Has2$^{flox/flox}$ homozygous mice. Has2$^{flox/flox}$ homozygous mice were then crossed with Colα2-iCre$^+$ mice to generate Colα2-iCre$^+$/Has2$^{flox/+}$. Further breeding with Has2$^{flox/flox}$ homozygous mice resulted in four genotypes in the offspring, including the conditional knock out mutant for Has2 (Colα2-iCre⁺/Has2⁻/⁻, termed Has2^(CKO/CKO)). Mice expressing Cre under the control of the FSP-1 (also called S100A4) promoter (FSP-1-Cre) were used (Lawson et al., 2005; Tanjore et al., 2009). CD44$^{-/-}$ mice were also used (Schmits et al., 1997). ASMA-HAS2⁺ were crossed with CD44-$^{-/-}$ to generate chimeras of ASMA-HAS2⁺/CD44$^{+/-}$, and the two chimeras were then back-crossed to get ASMA-HAS2⁺/CD44$^{-/-}$mice. C57B1/6J mice were from Jackson Laboratories. All mice were housed in a pathogen-free facility at Duke University, and all animal experiments were approved by the Institutional Animal Care and Use Committee at Duke University.

Fibroblast Isolation and Culture

Primary fibroblasts were derived from mouse lungs as described (Jiang et al., 2010; Tager et al., 2008). The cells were used from 3 to 6 generations. Human lung fibroblasts were isolated from surgical lung biopsies or lung transplant explants obtained from patients with idiopathic pulmonary fibrosis. Normal lung fibroblasts were obtained from discarded portions of normal transplant donor lung tissue. The specimens were obtained under the auspices of IRB-approved protocols. The tissues were minced, and cultured in DMEM medium supplemented with 15% FBS, 100 U/mL penicillin, 100 µg/mL streptomycin, 5 µg/mL gentamicin, and 0.25 µg/mL amphotericin B. The cells of passage 5-7 were used for invasion assays, siRNA interference assays, HA coat, and HA amount measurements. The diagnosis of IPF was arrived at by standard accepted American Thoracic Society recommendations (A TSIERS, 2000). All experiments were approved by the Duke University Institutional Review Board and in accordance with the guidelines outlined by the board.

Bleomycin Administration and Bronchoalveolar Lavage

Bleomycin was injected intratracheally at either a dose of 2.5 U/kg body weight for analysis of the early inflammatory response or 1.75 U/kg body weight for analysis of the late fibrotic response. Anesthesia was provided with a mixture of Ketamine of 100 mg/Kg (Fort Dodge, Overland Park, Kans.) and Xylazine of 10 mg/Kg (Lloyd Laboratories, Shenandoah, Iowa). At designated time points after bleomycin injection, mice were euthanized by Ketamine mixture injection and lungs were harvested for RNA preparation, protein isolation, or for fibroblast isolation. For bronchoalveolar lavage, the trachea was lavaged 3 times with 0.8 mL sterile saline at room temperature. Samples were centrifuged at 1500 rpm for 5 min and the supernatant was collected and stored at −80° C. until used. The cell-free supernatants were then analyzed for HA and chemokine KC concentrations by specific enzyme-linked immunosorbent assay (ELISA). The cell pellets were resolved in 1 mL sterile saline and the cells were counted with a hemocytometer. Approximately 40,000 cells from each specimen were loaded onto slides. These slides were stained using a Protocol HEMA 3 stain set (Fisher Diagnostics, Waltham, Mass.) and reviewed under light microscopy for white blood cell differential.

Hyaluronan Quantification

BAL fluid (BALF) and lung tissues were collected at different times after bleomycin treatment. Lung tissues were excised, weighed, and homogenized as described previously (Teder et al., 2002). After centrifugation, the HA content in the tissue supernatants and in BALF were measured using the HA-ELISA (Teder et al., 2002). The HA content in cultured media of human lung fibroblasts was quantified using the same ELISA method.

Histology, α-Smooth Muscle Actin (ASMA), and HA Immunohistochemistry

Three to eight mice in each group were sacrificed at various times after bleomycin treatment under anesthesia. The trachea was cannulated, and the lungs inflated with 1 mL of 10% formalin. The tissues were then fixed overnight, embedded in paraffin, and sectioned for staining with Hematoxylin and Eosin or Masson's Trichrome. Paraffin-embedded lung samples were also analyzed for HA localization. After being de-waxed and rehydrated, tissues were incubated with biotin-labeled HA binding protein (HABP) (4 µg/mL) (Associates of CAPE COD incorporated) for 1 h, then incubated and developed using a Vectastain-Elite-ABC kit (Vector Laboratories, Burlingame, Calif.), The specificity of the staining was determined by preincubating tissue samples with 10 U/mL *streptomyces* hyaluronidase for 2 h at room temperature. For ASMA staining, tissue sections were incubated with HRP-conjugated anti-ASMA monoclonal antibody (Dako, Denmark), and then incubated with the Vectastain-Elite-ABC kit as described above. For HA and ASMA double staining, tissue sections were incubated with biotin-HABP overnight at 4 GC, followed by incubation with Cy:3 labeled anti-ASMA antibody (Sigma, St. Louis, Mo.) to detect ASMA and streptavidin, Alexa Fluor® 488 conjugate (Invitrogen, Carlsband, Calif.) to detect HA. The processed sections were mounted in Fluoromount G (Immunokemi) containing DAPI and photographed with a Zeiss Microsystems microscope.

Hydroxyproline Assay

Collagen content in lung tissue from six to eight mice per group was measured with the conventional hydroxyproline method (Adamson and Bowden, 1974). The ability of the assay to completely hydrolyze and recover hydroxyproline from collagen was confirmed using samples containing known amounts of purified collagen.

Quantification of mRNA Expression

Real time RT-PCR was used to quantify the relative mRNA levels of HAS2 in C57B1/6J mice with or without bleomycin instillation using gene specific primers. In brief, total RNA was purified using RNAqueous™-4PCR kit (Ambion, Carlsbad, Calif.) and was reversed to cDNA using Superscript™ II RNase H Reverse Transcriptase Kit (Invitrogen, Carlsbad, Calif.) according to the manufacturer's instructions. HAS2 gene levels in the resultant cDNAs were examined using ABI Prism 7500 Detection system (Applied Biosystems, Carlsbad, Calif.) with SYBR-green as fluorescent dye enabling real time detection of PCR products according to the manufacturer's protocol (power SYBR Green PCR Master Mix, Applied Biosystems, Carlsbad, Calif.). The relative expression levels of the gene were determined against GAPDH levels in the samples. The same method was used to measure the relative mRNA levels of mouse HAS2 and human HAS2 genes in ASMA-HAS2⁺ mice and transgene negative littermate controls with or without bleomycin treatment, and was used to measure HAS2, MMP9, MP129 and MMP14 mRNA levels in mouse and human lung fibroblasts. The primers used were: human HAS2 (NM_005328) forward, 5'-TCG CAA CAC GT A ACG CAA T (SEQ ID NO:1); human HAS2 reverse, 5'-ACT TCT CTT TTT CCA CCC CAT TT (SEQ ID NO:2); human MMP9 (NM_004994) forward, 5'-CCC ACT GCT GGC CCT TCT A (SEQ ID NO:3); human MMP9 reverse, 5'-TCA CGT T.GC AGG CAT CGT (SEQ ID NO:4); human MMP12 (NM_002426) forward, TGC ACG CAC CTC GAT GTG (SEQ ID NO:5); human MMP12 reverse: GGC CCC CCT GGC ATT (SEQ ID NO:6); human MMP14 (NM_004995) forward, 5'-CGA GAG GAA GGA TGG CAA ATT (SEQ ID NO:7); human MMP14 reverse, 5'-AGG GAC GCC TCA TCA AAC AC (SEQ ID NO:8); human GAPDH (NM_002046) forward, 5'-CCC ATG TTC GTC ATG GGT GT (SEQ ID NO:9); human GAPDH reverse, 5'-TGG TCA TGA GTC CTT CCA CGA TA (SEQ ID NO:10); mouse HAS2 (NM_009216) forward, 5'-ACG ACG ACC TTT ACA TGA TGG A (SEQ ID NO:11); mouse HAS2 reverse, 5'-GAT GTA CAT GGC CGA TTT GCT (SEQ ID NO:12); mouse GAPDH forward, 5'-ATC ATC TCC GCC CCT TCT G (SEQ ID NO:13); and mouse GAPDH reverse, 5'-GGT CAT GAG CCC TTC CAC AAC (SEQ ID NO:14).

qRT-PCR Array Assay

Fibroblasts from bleomycin-treated ASMA-HAS2$^+$ mice were loaded onto 6-well matrigel chambers or 6-well insert chambers without matrigel (BD Bioscience, Franklin Lakes, N.J.), and cultured in $CO_2$ incubator for 48 h. Matrigel matrix and non-invading cells on the upper surface of the filter were removed by wiping with a cotton swab and the polycarbonate filters with the invaded cells or migrated cells were washed once with PBS, RNA were isolated from the cells using the RNAqueous™-4PCR kit (Ambion, Carlsbad, Calif.). Reverse transcription was performed using the RT2 First Strand cDNA Synthesis kit (SABiosciences, Frederick, Md.), and 84 genes were assessed by RT-PCR using the Mouse Extracellular Matrix and Adhesion Molecules array ($RT^2$ Profiler PCR Array PAMM-013; SABiosciences, Frederick, Md.) according to manufacturers instructions using ABI Prism 7500 Detection system (Applied Biosystems, Carlsbad, Calif.). For analysis, the expression level for each gene of interest (GOI) was calculated as 2-Ct followed by normalization to GAPDH (HKG), using the formula 2-(Ct GOI-Ct HKG). Ultimately the fold change in normalized gene expression was calculated by comparing values from the invaded fibroblasts through matrigel (with invasion) to the migrated fibroblasts through filter without matrigel (without invasion) according to the following formula: 2-Ct with invasion/2-Ct without invasion. Values were calculated for replicates of 5 independent experiments.

HA Pericellular Coat Determination

Fibroblasts isolated from $Has2^{flox/+}$, $Has2^{CKO/CKO}$ mouse lungs, and fibroblasts from human lung tissues were incubated at $1 \times 10^4$ cells/well of 6-well plate for 24 h in 10% FBS-DMEM, and were then overlaid with $1 \times 10^7$ erythrocytes. The erythrocytes were allowed to settle for 15 min at RT and the cells were observed with an inverted microscope with a phase contrast at 200× magnification with a Zeiss camera. The size of the pericellular coat was defined by the subtraction between the area excluding erythrocytes and cell area by using the NIH Image J program.

Matrigel Invasion Assay

The invasive behavior of fibroblasts isolated from WT, ASMA-HAS2$^+$, ASMA-HAST, $Has2^{CKO/CKO}$, $Has2^{FKO/FKO}$, ASMA-HAS2$^-$/CD44$^{-/-}$, ASMA-HAS2$^+$/CD44$^{-/-}$ and CD44$^{-/-}$ mouse lungs were performed essentially as described previously (Hager et al., 2009; Li et al., 2007). Equal numbers of fibroblasts were plated onto the BioCoat Matrigel Invasion Chamber (BD Biosciences, Franklin Lakes, N.J.); and the cell invasion was performed in the presence of 10% FBS complete medium. After 24 h of incubation in $CO_2$ incubator, media were removed and the polycarbonate filters with the invaded cells were washed once with PBS followed by fixing and staining with the Protocol Hema3 stain set. Matrigel matrix and non-invading cells on the upper surface of the filter were removed by wiping with a cotton swab and the filters were removed from the insert by a scalpel blade, and were mounted onto glass slides. The invading cells of each sample were counted in 5 randomly selected fields of duplicate filters under microscope at 400× magnification. The invasive capacity of fibroblasts from IPF patients was compared to fibroblasts from normal donators using the same invasion assay. CD44 effects on mouse and human lung fibroblasts invasion were assessed using anti-CD44 blocking antibodies (15 μg/mL, 5F12 clone for human CD44, KM201 for mouse CD44). The cells were incubated with anti-CD44 or isotype-matched IgG for 20 min before performing the invasion assay. The effects of HAS2 expression levels on human lung fibroblasts' invasion were investigated by performing the invasion assay at 48 h after HAS2 siRNA and control siRNA transfection.

RNA Interference Assay

Four siRNA duplexes designed to target different nucleotide sequences (HAS2 si, 1530-1550; HAS2 si2, 1051-1071; HAS2 si3, 1424-1444; HAS2 si4, 1777-1797) of the human HAS2 gene [NM_005328] were obtained from Qiagen (Germantown, Md.). Sub confluent fibroblasts (about 50-60% confluent) grown in complete medium were transfected separately with each 1 of the 4 siRNA duplexes or with a control siRNA (control si) (Qiagen, Germantown, Md.) at the concentration of 100 nM using HiperFect transfection reagent (Qiagen, Germantown, Md.) according the manufacturer's instructions. The suppression efficiency of each 1 of the 4 siRNA duplexes was examined by measuring the hyaluronan content in the conditioned culture media after 48 and 72 h of transfection, HAS2 mRNA at 72 h after transfection and HA coat, 48 h after transfection. The HAS2 siRNA corresponding to nucleotide sequences 1530-1550 of the HAS2 cDNA (CAGCTCGATCTAAGTGCCTTA; SEQ ID NO:15; HAS2 si) was used for all experiments.

Western Blotting

Wild type, ASMA-HAS2$^+$, and littermate control lung tissues after bleomycin treatment were homogenized in RIPA buffer. The proteins were fractionated by sodium dodecyl sulfate-polyacrylamide gel electrophoresis (SDS-PAGE) using gradient gel (4-20%, Bio-Rad) and electroblotted onto nitrocellulose membrane (Bio-Rad). The membranes were probed with a rat monoclonal anti-CD44 antibody (KM114, BD Pharmingen, Franklin Lakes, N.J.), and then probed with relative second antibody. B-actin was used as a loading control.

Administration of Neutralizing Anti-CD44 Monoclonal Antibody

TIB-240 hybridoma cells producing rat anti-mouse CD44 blocking antibody (KM201) were purchased from ATCC (Manassas, Va.). The antibody was isolated using saturated ammonium sulfate method. Two schemes were used for the antibody administration. Preventive protocol, KM201 or isotype control rat IgG, (300 μg in 500 μL saline) was administered intraperitoneally 12 h before bleomycin challenge and repeated injections in the same way (200 μg/500 μL saline) on day 5 after bleomycin treatment. 14 days after bleomycin challenge, mouse lungs were collected and collagen content in the mouse lungs was measured using hydroxyproline assay as described. Therapeutic protocol, KM201 or isotype control rat IgG, (300 μg in 500 μL saline) was administered intraperitoneally at day 7 after bleomycin treatment, and repeated injections in the same way at day 14 and day 21 after bleomycin treatment. 28 days after bleomycin challenge, mouse lungs were collected and collagen content in the mouse lungs was measured using the hydroxyproline (Adamson and Bowden, 1974).

Statistical Analysis

Data are expressed as the mean±SEM where applicable. We assessed differences in measured variables using the unpaired two-sided Student t-test, or Wilcoxon rank-sum test with nonparametric data. Differences between multiple groups were calculated using one-way ANOVA with Tukey-Kramer post test or two-way ANOVA with Bonferroni multiple comparisons. Statistic significance of survival curves was analyzed with the log-rank test. Statistical difference was accepted at P<0.05. Prism 5.0 or JMP5 software was used to perform statistical analysis.

Figure 2:
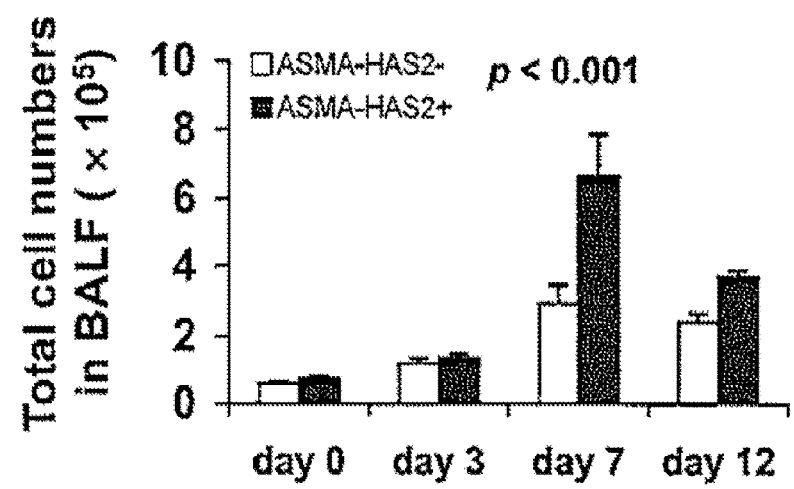
FIG. 2 shows that ASMA-HAS2$^+$ mice exhibit an increase in neutrophil recruitment after lung injury. (A, B) BALF cells were collected on the indicated days after bleomycin treatment and total cell (A) and differential cell counting (B) were performed (n=4-12 for each group; P=0.001). (C) H&E staining of lung sections from ASMA-HAS2$^+$ mice and their littermate controls at day 7 after bleomycin treatment. Pictures shown are representatives of 5 samples. Scale bars, 200 µm. (D) Chemokine KC levels were measured in BALF from ASMA-HAS2$^+$ and its controls (n=5-12) at day 0, day 7 after lung injury (*$P<0.05$).
Figure 2:
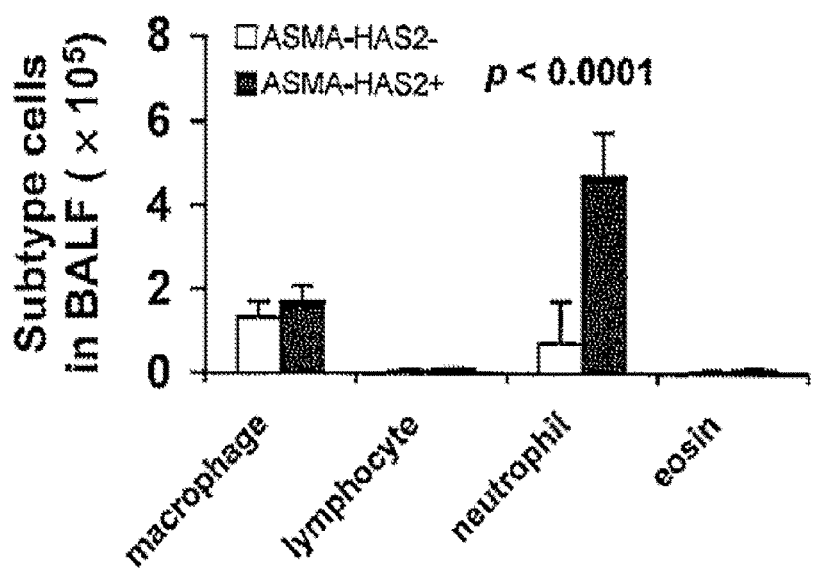
Figure 2:
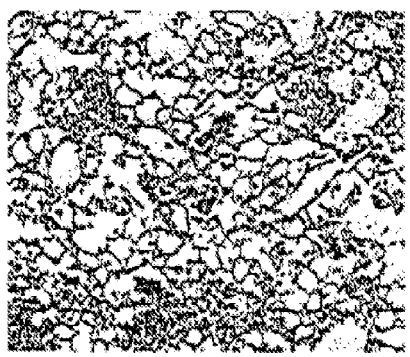
Figure 2:
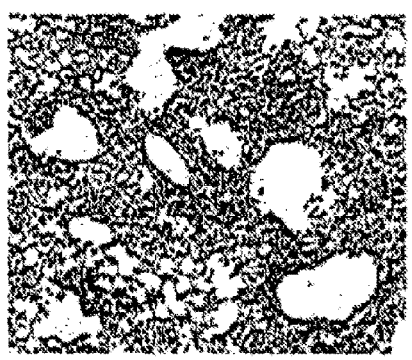
Figure 2:
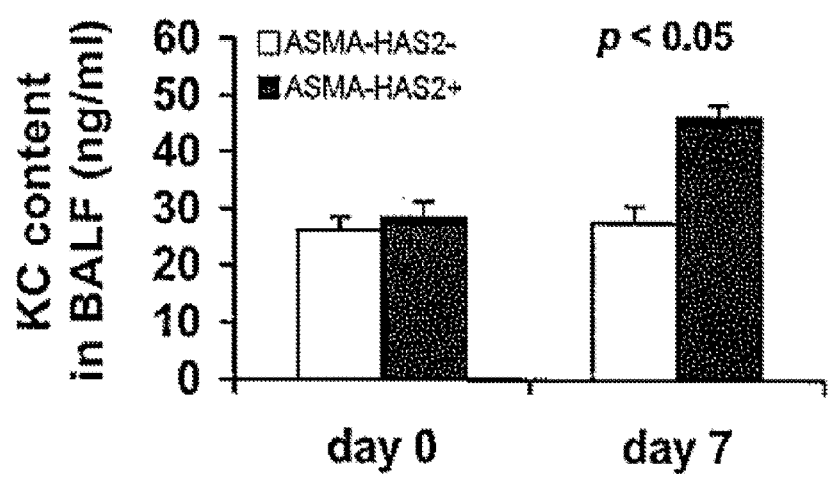
Figure 3:
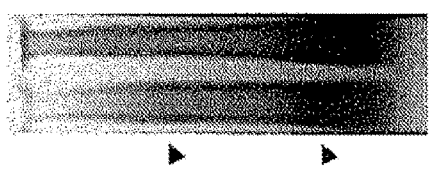
FIG. 3 shows increased HA fragment accumulation in ASMA-HAS2$^+$ mouse lungs after bleomycin treatment. (A) Representative images showing HA size from ASMA-HAS2$^+$ and littermate controls 7 days after bleomycin treatment. HA peaks are annotated with arrows, (B) Quantification analysis of HA molecular weight distribution in lung tissues of ASMA-HAS2$^+$ and littermate controls at day 0 and day 7 after 1.75 U/kg and 2.5 U/kg bleomycin treatment. Black circle: ASMA-HAS2$^+$; grey circle: ASMA-HAS2$^+$.
Figure 3:
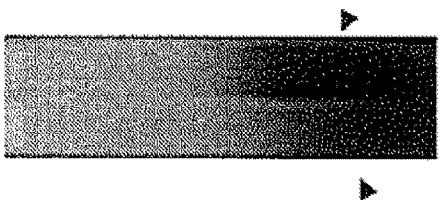
Figure 3:
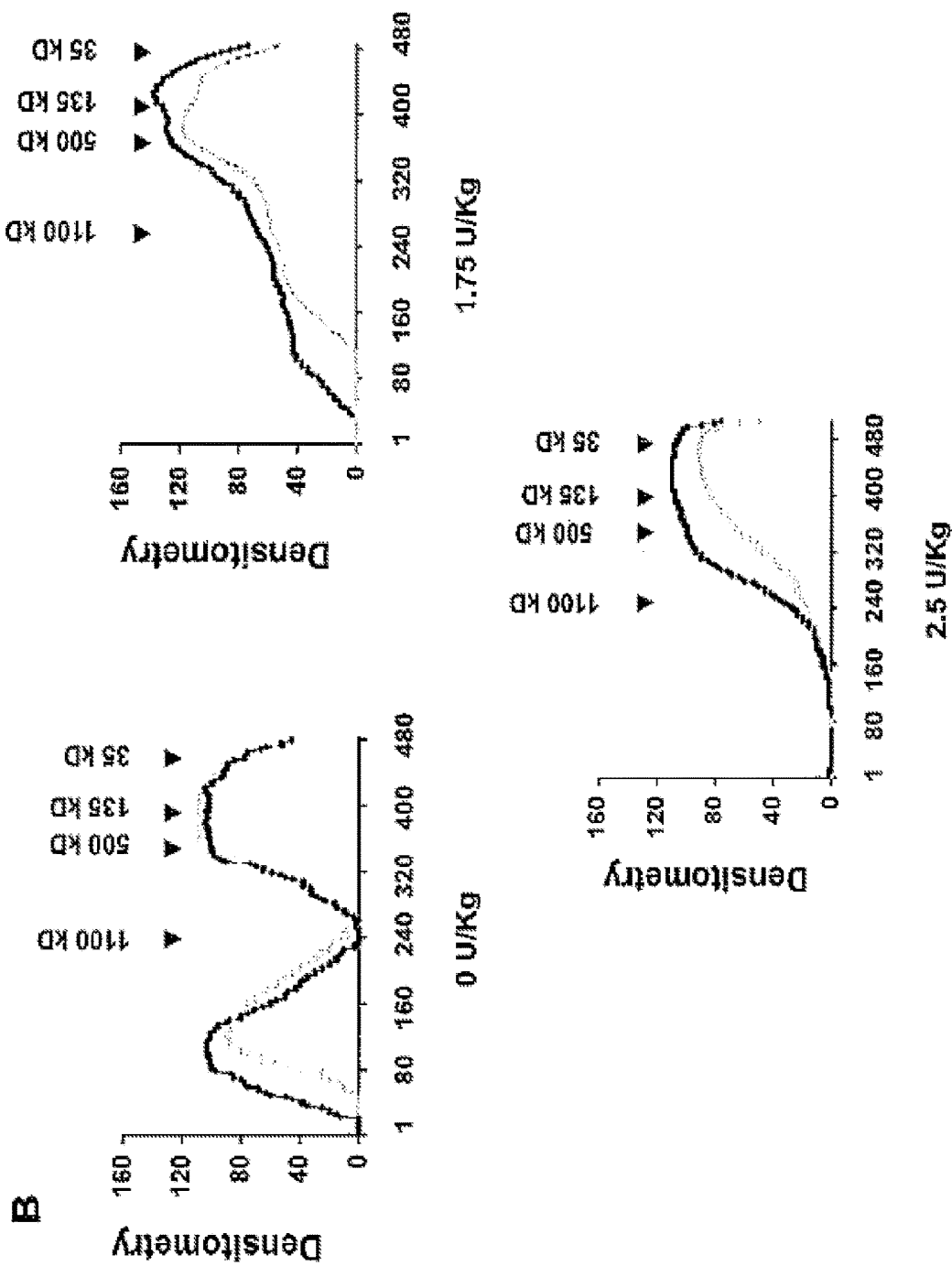
Figure 4:
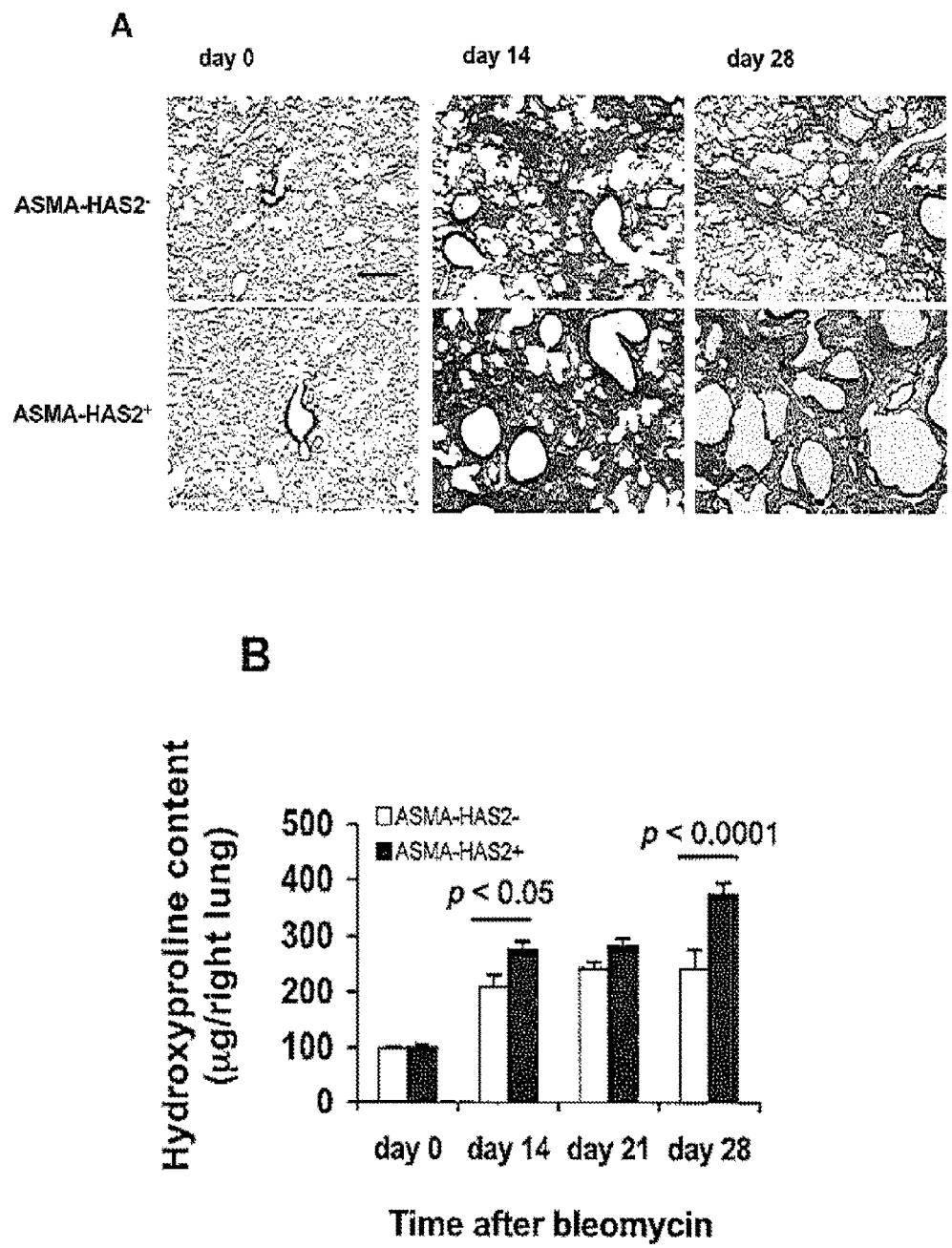
FIG. 4 shows ASMA-HAS2 transgenic mice exhibit increased collagen content in lungs after bleomycin treatment. (A) Lung sections of ASMA-HAS2$^+$ and transgene negative controls 0, 14 and 28 days after bleomycin instillation were stained using Masson's Trichrome method. Representative images of the staining are shown (n=6-7). Scale bars, 200 µm. (B) Lung tissues from ASMA-HAS2$^+$ and controls on day 0, 14, 21 and 28 after bleomycin treatment were collected and assayed for collagen content using the hydroxyproline method (n=6-7 per group; *p<0.05; ****p<0.0001 by 2-way ANOVA with Bonferroni post test). The experiments were performed three times. (C) Immunohistochemical and (D) immunofluorescent analysis of ASMA and HA in lung sections of ASMA-HAS2+ and control mice 14 days after bleomycin treatment. Representative images of the staining are shown (n=6-7 per group; *p<0.05; ***p<0.0001 by 2-way ANOVA with Bonferroni post test). The experiments were performed three times. (C) Immunohistochemical and (D) immunofluorescent analysis of ASMA and HA in lung sections of ASMA-HAS2$^+$ and control mice 14 days after bleomycin treatment. Representative images of the staining are shown (n=6-7). (C) DAB Staining. Scale bar, 50 µm; (D) immunofluorescence staining. Scale bars, 200 µm. (E) Representative image of IPF patients' lung tissue showing ASMA staining and similar fibrotic changes to bleomycin-induced lung fibrosis. Scale bars, 200 µm.
Figure 4:
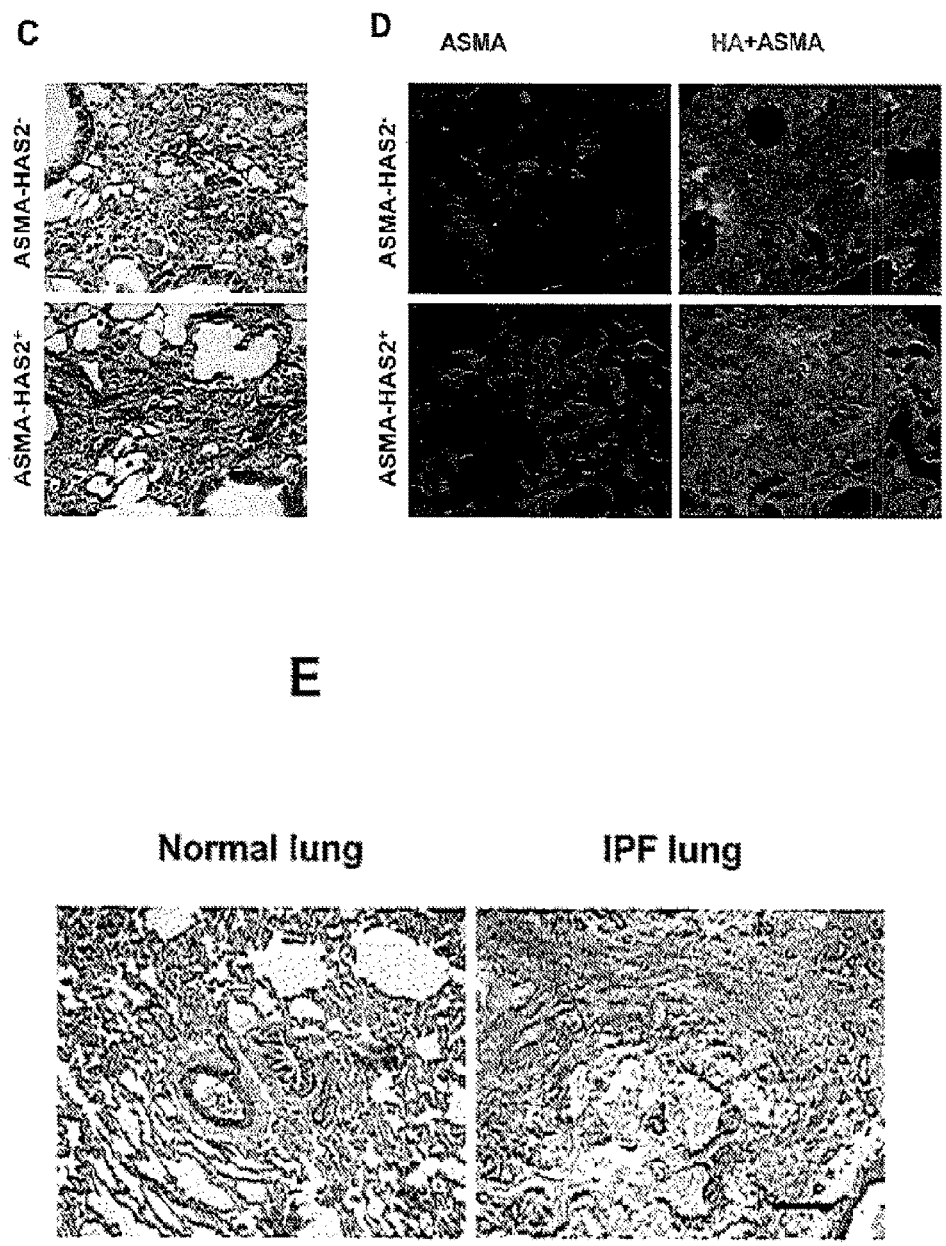

Example 2. Targeted Overexpression of HAS2 in α-Smooth Muscle Actin-Expressing Cells Generates a Severe Fibrotic Phenotype In order to characterize the role of HAS2 expression by myofibroblasts in the pathogenesis of pulmonary fibrosis we evaluated transgenic mice with targeted human HAS2 expression in ASMA-expressing cells. ASMA-HAS2 transgenic mice develop normally and exhibit no overt phenotype in the unchallenged state. Intratracheal administration of bleomycin recruits myofibroblasts and causes pulmonary fibrosis. It was found that ASMA-HAS2 transgenic mice exhibited an increase in HA deposition around large airways and blood vessels at baseline and accumulate increased concentrations of HA in both the lung interstitium and alveolar space after injury (FIG. 1A-C). The specificity of the staining was determined by preincubating tissue samples with 10 U/mL *streptomyces* hyaluronidase for 2 h at room temperature (data not shown). The experiment was performed three times. Endogenous murine HAS2 gene expression was upregulated following bleomycin treatment (FIG. 1D) but human HAS2 was only expressed in the transgenic mice (FIG. 1E). ASMA-HAS2 transgenic mice demonstrated a marked increase in mortality following lung injury over a dose range of bleomycin. Percentages of surviving mice with various doses of bleomycin treatment were plotted over a 21-day period (n=8-16 per group; p values are indicated; Statistic significance of survival curves was determined by the log-rank test). Experiments were performed three times (FIG. 1F; red line: ASMA-HAS2⁻; blue line: ASMA-HAS2⁺). To evaluate the mechanisms leading to increased mortality in ASMA-HAS2 transgenic mice, we first examined the inflammatory response following lung injury. ASMA-HAS2 transgenic mice were found to have an increase in total inflammatory cells relative to transgene negative controls and the increase was largely due to an influx of neutrophils (FIG. 2A-C). We analyzed the bronchoalveolar lavage fluid for neutrophil chemotactic peptides and found a marked increase in the chemokine KC in the ASMA-HAS2 transgenic mice (FIG. 2D). It was previously known that HA fragments accumulate following lung injury and stimulate macrophages to produce inflammatory mediators. ASMA-HAS2 transgenic mice were found to accumulate abundant HA fragments in lung tissue (FIG. 3A,B), and the experiments were repeated two times. We then examined the fibrotic response in ASMA-HAS2 transgenic mice and found evidence of progressive fibrosis at time points (28 days) when the fibrotic response in transgene negative mice was abating (FIG. 4A,B). Both the magnitude and duration of the fibrotic response was greater in the ASMA-HAS2 transgenic mice. Furthermore, a fibrodestructive response in the periphery of the lung was observed in the ASMA-HAS2 transgenic mice (FIG. 4A) similar to that observed in lung tissue from patients with IPF. We also found an impressive increase in the accumulation of ASMA-staining in lung tissue from ASMA-HAS2 transgenic mice consistent with greater accumulation of myofibroblasts (FIG. 4C,D) that was similar to what was observed in IPF lung tissue (FIG. 4E).

Figure 5:
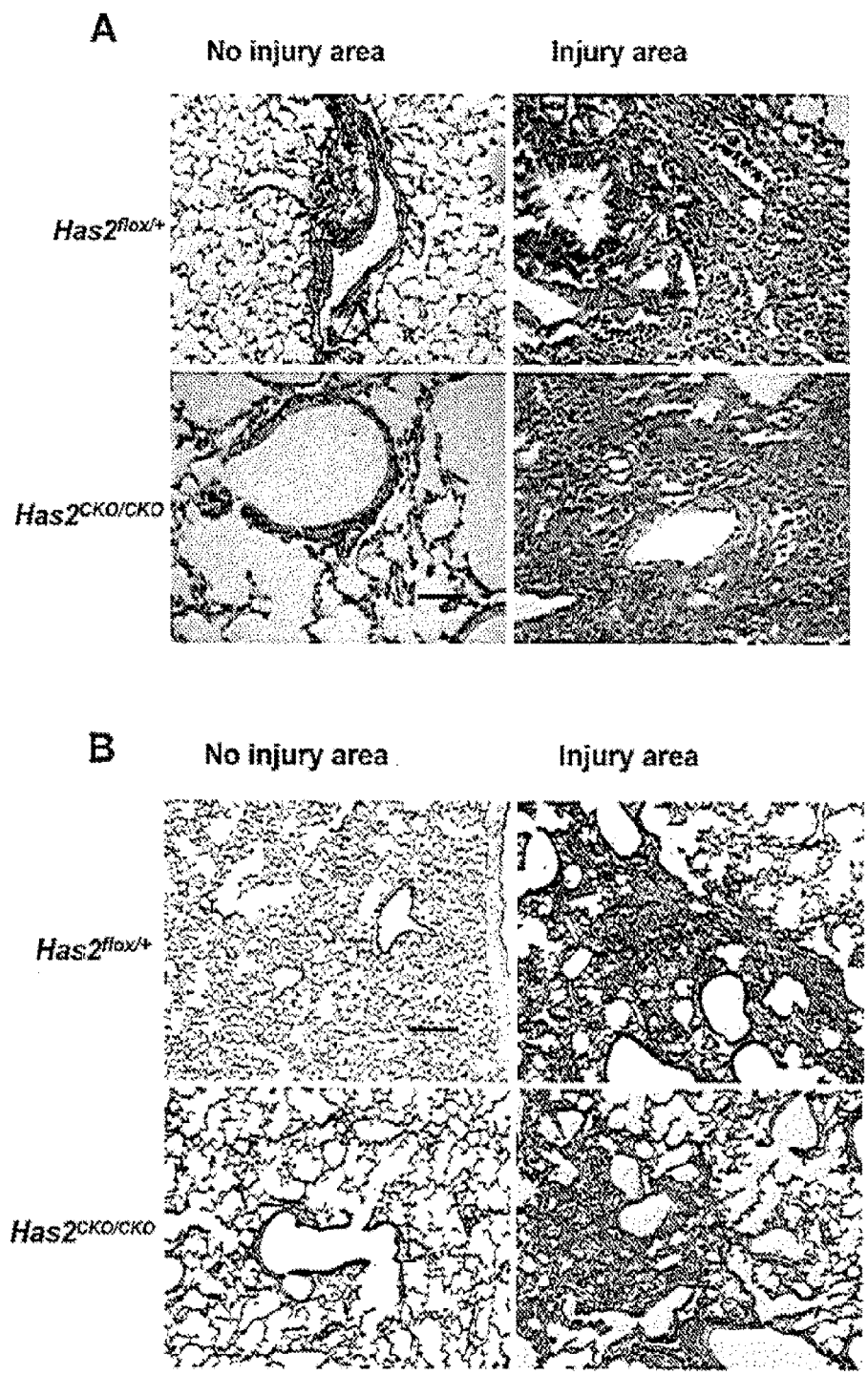
FIG. 5 shows targeted deletion of HAS2 in mesenchymal cells inhibits lung fibrosis and myofibroblast accumulation. (A) Comparison of HA distribution in lung tissues of bleomycin-treated Has2$^{CKO/CKO}$ and control (Has2$^{flox/+}$) mice by immunohistochemistry. Scale bars, 50 um, (B) Lung sections of Has2$^{CKO/CKO}$ and Has2$^{flox/+}$ on day 14 after bleomycin instillation were stained using Masson's Trichrome method and counterstained with hematoxylin. The experiments were repeated four times. Scale bars, 200 µm. (C) Double staining of HA (green) and ASMA (red) in bleomycin-injured lung tissue 14 days after bleomycin. Scale bars, 200 µm, (D) HA content in lung tissue from Has2$^{FKO/FKO}$ and Has2$^{flox/+}$ mice on day 14 after bleomycin treatment (n=3-8). (E) Lung tissues from Has2$^{FKO/FKO}$ and control Has2$^{flox/+}$ mice on day 0, 14 and 21 after bleomycin treatment were collected and assayed for collagen content using the hydroxyproline method. n=4-11 per group. *p<0.05 by 2-way ANOVA with Bonferroni post test. The experiments were performed three times. (F) Lung sections of Has2$^{FKO/FKO}$ and Has2$^{flox/+}$ mice on day 0 and 14 after bleomycin instillation were stained using Masson's Trichrome method and counterstained with hematoxylin. n=8 in each group. Scale bars, 200 µm, (G) Double staining of HA (green) and ASMA (red) in bleomycin-treated HAS2$^{FKO/FKO}$ control Has2$^{flox/+}$ mouse lung sections. Scale bars, 200 µm.
Figure 5:
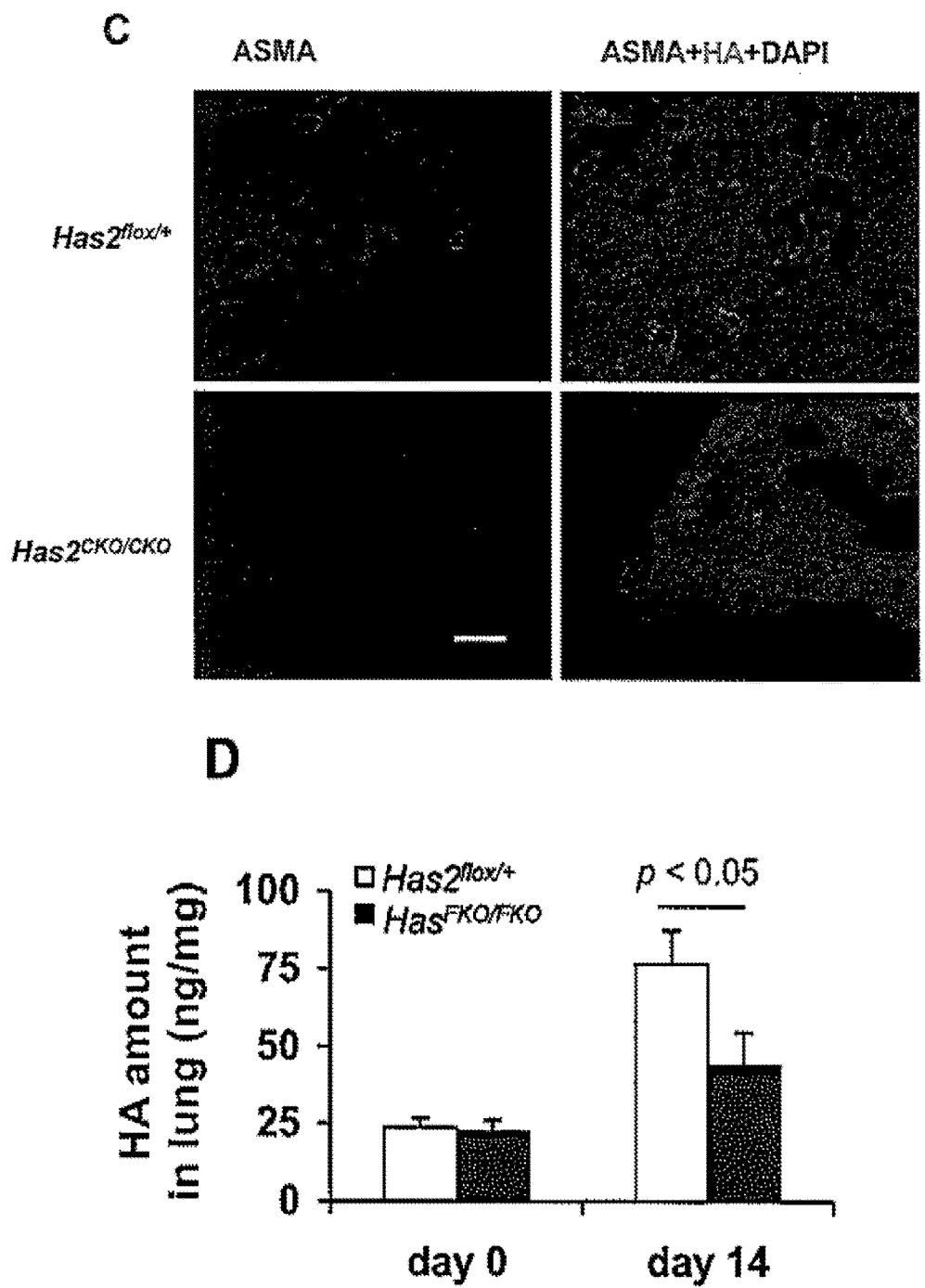
Figure 5:
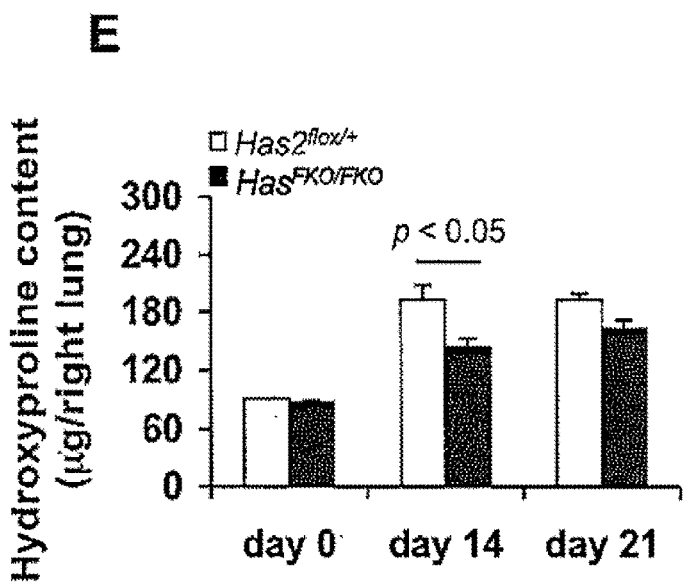
Figure 5:
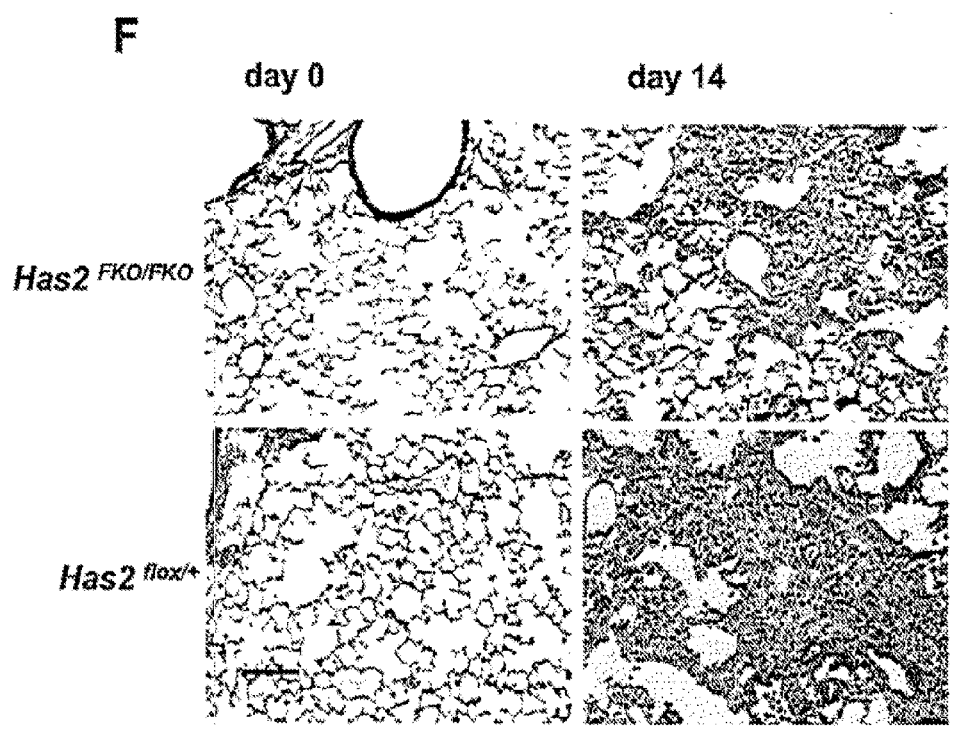
Figure 5:
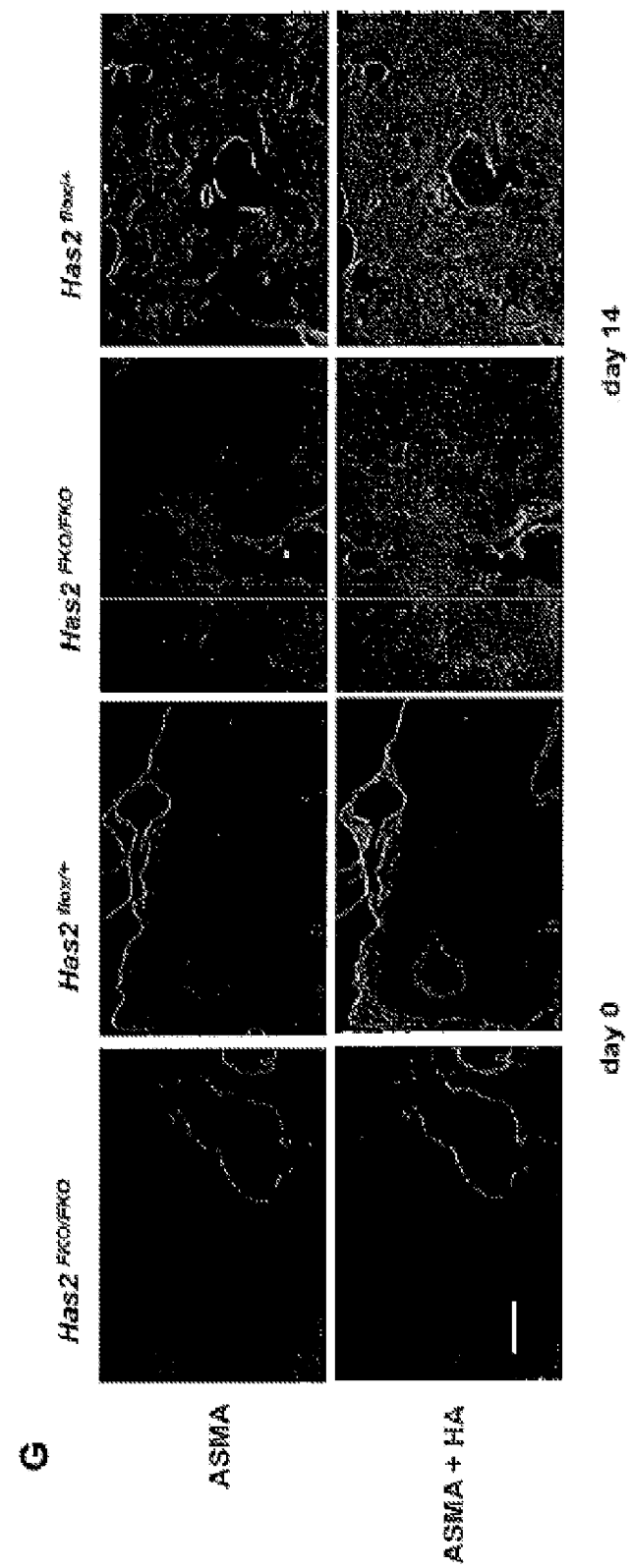

Example 3. Conditional Knockout of HAS2 in Mesenchymal Cells Diminishes the Accumulation of Myofibroblasts and the Development of Pulmonary Fibrosis HAS2 deficient mice have an embryonic lethal phenotype. In order to ascertain the role of HA in mesenchymal cell functions, we generated Has2$^{flox/+}$ mice and crossed them with a Colα2-iCre transgenic line. Unfortunately, the vast majority of Colα2-iCre+/Has2$^{flox/flox}$ mice (Has2$^{CKO/CKO}$) also died in utero, suggesting that HA production by mesenchymal cells drove the phenotype. Conditional Has2$^{CKO/CKO}$ mice were treated with bleomycin at 8 weeks of age. As shown in FIGS. 3A, and B, Has2$^{CKO/CKO}$ mice had minimal HA staining in bronchial tissues at baseline and developed less fibrosis after lung injury as estimated by Trichrome staining. In addition, at sites of lung remodeling, there was a marked reduction in myofibroblast accumulation in the lung relative to wild type or ASMA-HA transgenic mice (FIG. 5C). In order to further assess the contribution of fibroblast expression of HAS2, we utilized an additional Cre line using the FSP-1 promoter. FSP-1 is expressed by lung fibroblasts. FSP-1-Cre mice were crossed with the Has2$^{flox/flox}$ line to generate FSP-I-Cre⁺/Has2$^{flox/flox}$ (Has2$^{FKO/FKO}$) mice. These mice were viable and demonstrated no overt phenotype in the unchallenged state. We challenged Has2$^{FKO/FKO}$ mice with bleomycin and found a substantial inhibition in the accumulation of both hyaluronan (FIG. 5D) and collagen in lung tissue following injury (FIG. 5E,F). In addition, there was also a decrease in the accumulation of myofibroblasts as assessed by ASMA staining of lung tissues (FIG. 5G). Thus, two different fibroblast driver lines showed that HAS2 expression by mesenchymal cells was involved with the development of pulmonary fibrosis and myofibroblast accumulation after tissue injury. These gain and loss of function interventions supported a fundamental role for HAS2 in the development of pulmonary fibrosis.

Example 4. HAS2 Expression in Myofibroblasts Promotes an Invasive Phenotype

Figure 6:
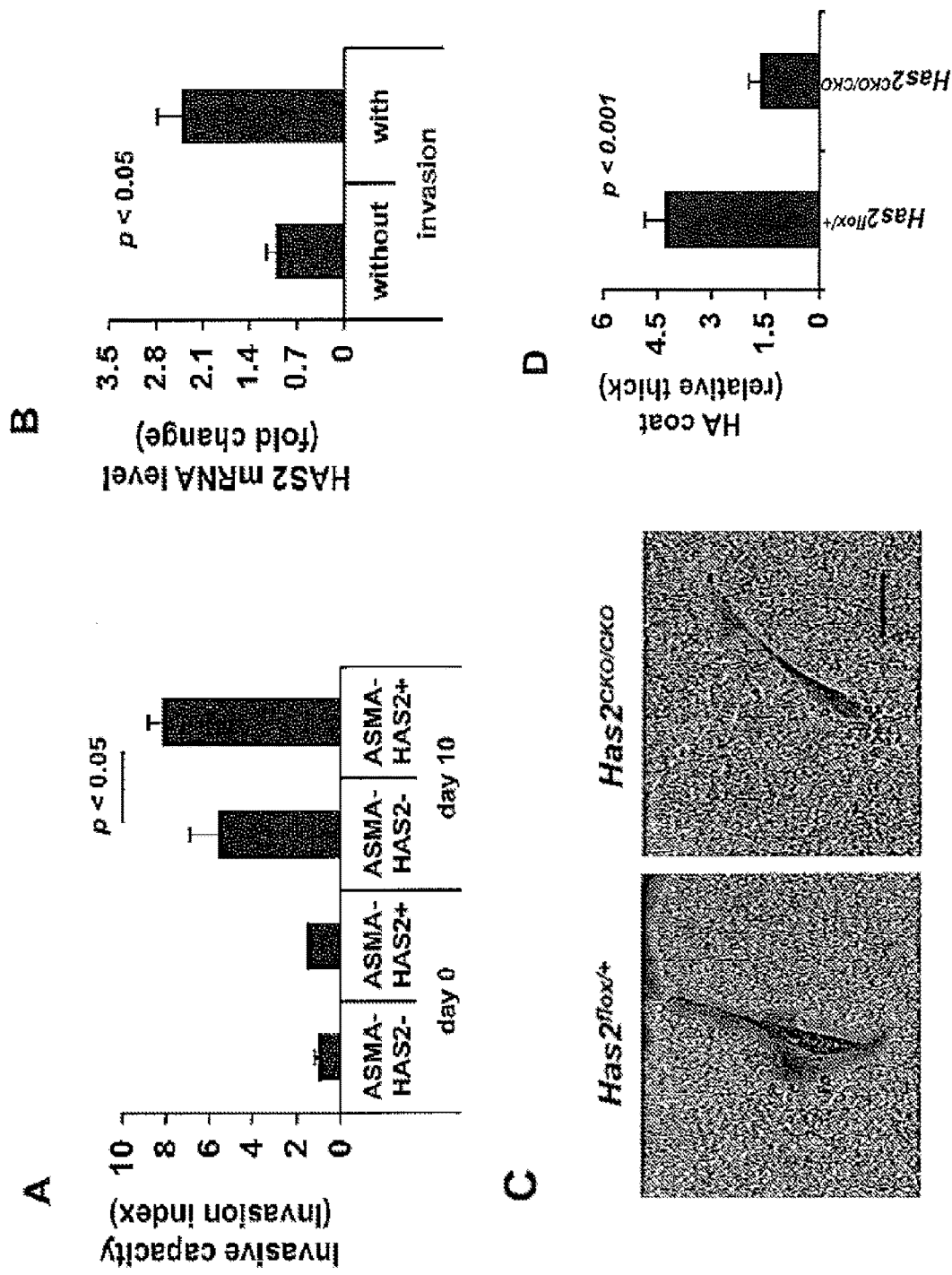
FIG. 6 shows that fibroblast invasive capacity is dependent upon HAS2. (A) The spontaneous matrigel-invading capacity of fibroblasts from bleomycin-treated (10 days) and saline-treated ASMA-HAS2$^+$ and littermate control mice lungs was determined. Data are shown as the index of invasion value of the fibroblasts with or without bleomycin treatment over littermate control fibroblasts without bleomycin challenge. The experiments were repeated two times (n=4; p values were indicated). The experiments were performed three times. (B) Invasive fibroblasts exhibited increased HAS2 expression level. Message RNA relative levels of HAS2 in invasive and non-invasive fibroblasts isolated from bleomycin-treated (11 days) WT mouse lungs were determined using real-time PCR (n=5, *p<0.05 by Wilcoxon rank sum test). The experiments were performed three times. (C) Phase contrast photomicrographs of the pericellular matrices (HA coat) demonstrated reduced HA coat in Has2$^{CKO/CKO}$ fibroblasts compared with those in Has2$^{flox/+}$ fibroblasts. Scale bar, 50 µm. Experiments were performed three times. (D) Relative thickness of HA coat was calculated in 20 randomly selected cells using the NIH Image J program (n=10; ***P<0.001 by Wilcoxon rank sum test). Data represent one of two independent experiments. (E) HA content in cultured media of Has2$^{flox/+}$ and Has2$^{CKO/CKO}$ fibroblasts was measured using the HA-ELISA assay (n=3; p values were indicated). The experiments were performed three times. (F) Comparison of the invasive capacity between Has2$^{flox/+}$ and Has2$^{CKO/CKO}$ fibroblasts. Data are shown as invasion index of Has2$^{CKO/CKO}$ fibroblasts over Has2$^{flox/+}$ fibroblasts (data shown are representative of three independent experiments; p values are indicated). (G) Comparison of the invasive capacity between fibroblasts from bleomycin-treated Has2$^{flox/+}$ and Has2$^{FKO/FKO}$ mice. Data are shown as invasion index of Has2$^{FKO/FKO}$ fibroblasts over Has2$^{flox/+}$ fibroblasts (n=3; p values are indicated). The experiments were performed three times.
Figure 6:
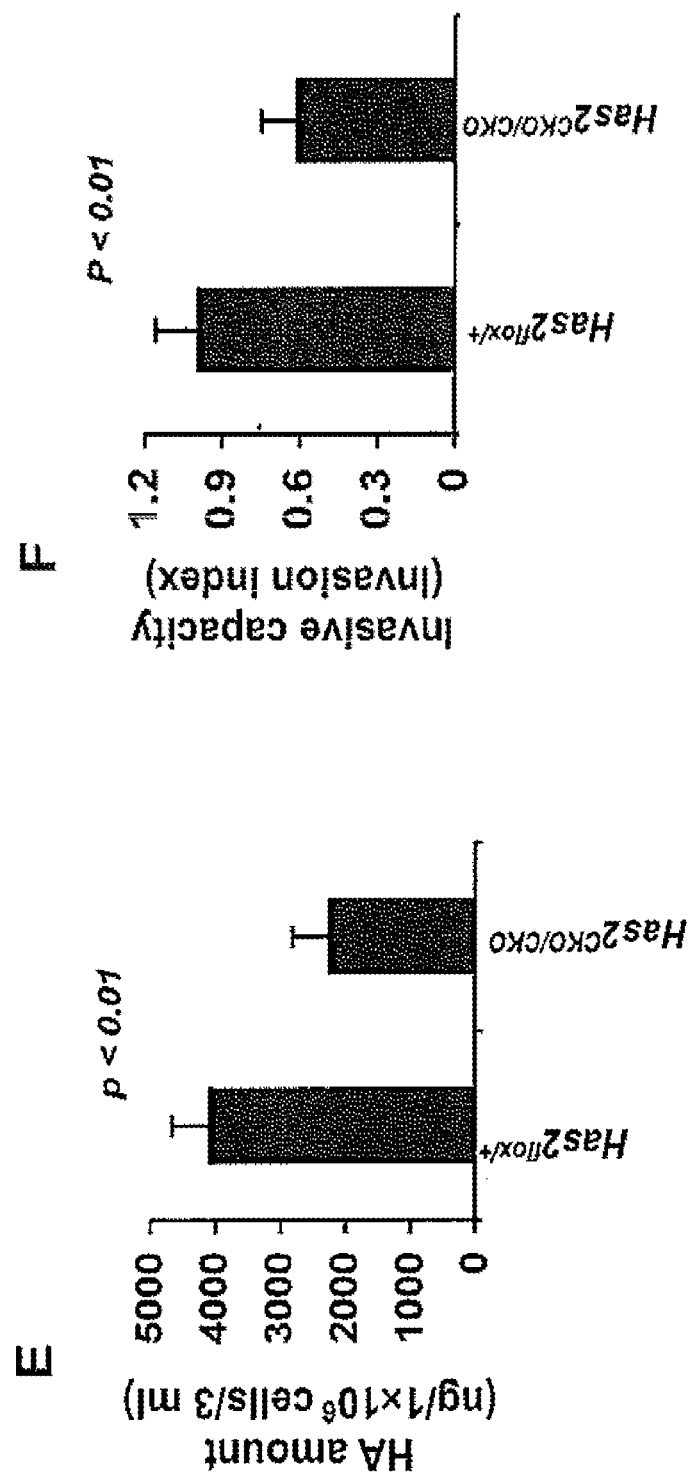
Figure 6:
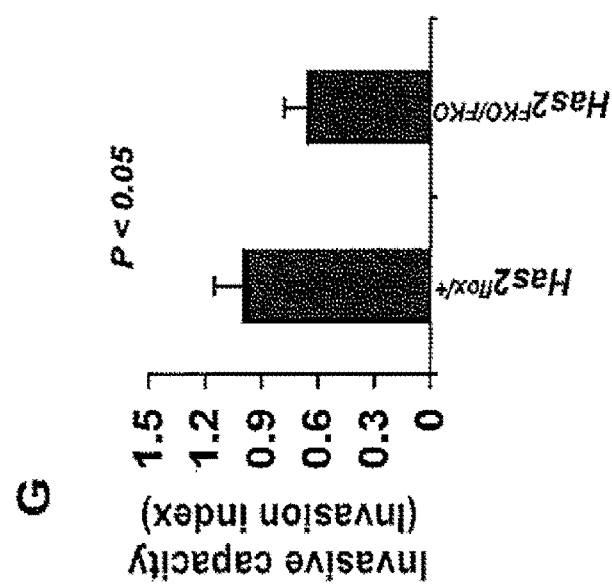

We investigated whether or not fibrotic fibroblasts acquire an invasive phenotype that is essential for severe fibrogenesis and whether or not HAS2 regulates the process. We utilized an assay system in which fibroblasts were evaluated for their ability to spontaneously invade matrigel, a composite matrix with basement membrane constituents. We compared fibroblasts isolated from ASMA-HAS2 transgenic mice and littermate control mice before and after bleomycin challenge. We found that fibrotic fibroblasts spontaneously invaded matrigel (FIG. 6A). Interestingly, invasive fibroblasts demonstrated increased HAS2 mRNA expression relative to fibroblasts isolated that did not invade matrix (FIG. 6B), suggesting that Has2 expression was an consistent feature of the subset of fibroblasts that invaded matrix. Fibroblasts isolated from bleomycin treated ASMA-HAS2 transgenic mice demonstrated greater invasive capacity than trans gene negative controls (FIG. 6A). To determine the contribution of HA to the invasive phenotype we sought to identify fibroblasts deficient in HAS2 expression and HA production. We were able to isolate fibroblasts from Has2$^{CKO/CKO}$ and Has2$^{FKO/FKO}$ mice and examined HA production. A hallmark of mesenchymall cell HA expression is the formation of cell surface HA coats, and HA is synthesized in the cell membrane and extruded to the external milieu. Conditional Has2 null)(Has2$^{CKO/CKO}$) fibroblasts show a marked reduction in the ability to form cell surface coats and exclude exogenous particles (FIG. 6C,D). They were severely deficient in HA production (FIG. 6E). We examined the ability of conditional Has2 null fibroblasts to invade matrigel and found a marked reduction in invasive capacity (FIG. 6F,G). These gain and loss of function interventions supported a fundamental role for HAS2 in the development of an invasive myofibroblast phenotype.

Figure 7:
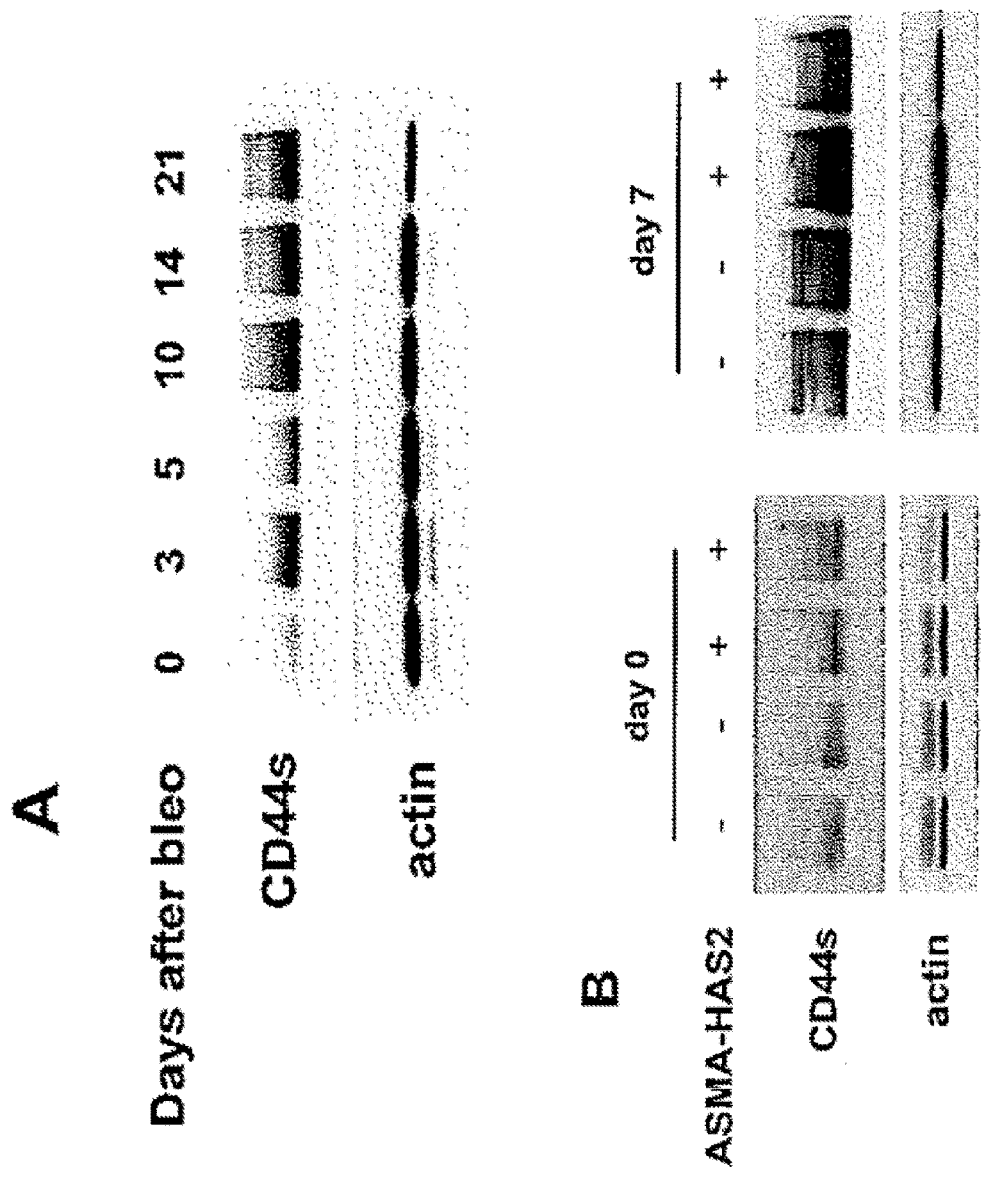
FIG. 7 shows CD44 regulates lung fibrosis and fibroblast invasive capacity. (A) Western blotting analysis of CD44 expression using KM 114 anti-CD44 antibodies in wild type lung tissues at indicated times after bleomycin treatment. Samples loaded at each time point was the mixture of equal amount of three samples collected per time point. β-actin was used as a loading control. CD44 standard form (82.0 kD) is indicated. The experiments were performed three times. (B) Immunoblot of CD44 in ASMA-HAS2$^+$ (+) and control (−) mouse lung tissues on day 0 and day 7 after bleomycin treatment. The experiment was performed three times. (C) Lung tissues from CD44 null and WT mice on day 0 and 21 after bleomycin treatment were collected and assayed for collagen content using the hydroxyproline method. n=14-17 per group. *p<0.05 between WT and CD44 null at day 21, as determined by Wilcoxon rank: sum test, The experiments were performed three times. (D) Lung sections of WT and CD44 null mice on day 21 after bleomycin instillation were stained using Masson's Trichrome method. Representative images of the staining are shown (n=5-6). Scale bars, 200 µm. The experiment was repeated twice. (E) Bleomycin-induced lung fibrosis in ASMA-HAS2$^+$ mice was attenuated in ASMA-HAS2$^+$/CD44$^{−/−}$ mice. Hydroxyproline content on day 21 after bleomycin treatment was analyzed (n=7-8, per group. p<0.01 by 2-way ANOVA with Bonferroni post test). The experiments were performed three times. (F) Neutralizing anti-CD44 antibodies installation 12 h before and 5 days after bleomycin treatment in ASMA-HAS2$^+$ mice prevented bleomycin-induced lung fibrosis (n=5-8 per group, p value is indicated). The experiment was performed three times. (G) Systemic installation of neutralizing anti-CD44 antibodies on day 7, day 14, and day 21 after bleomycin treatment in ASMA-HAS2$^+$ mice inhibited bleomycin-induced lung fibrosis. (n=6-9 per group; *p<0.001 by one-way ANOVA with Tukey-Kramer post test). The experiments were performed three times. (H) Lung sections of the mice described in (G) were stained using Masson's Trichrome method. Representative images of the staining are shown. Scale bars, 200 µm. (I) The spontaneous matrigel-invading capacity of fibroblasts from bleomycin-treated (7 and 11 days) and saline-treated wild type (WT) C57Bl/6J and CD44-null mouse lungs was determined. Data are shown as the index of invasion value of the fibroblasts with or without bleomycin treatment over WT fibroblasts without bleomycin challenge. n=4 per group. The experiments were repeated three times. (J) Invasive capacity of mesenchymal cells from ASMA-HAS2⁻, ASMA-HAS2⁺, ASMA-HAS2⁻/CD44⁻/⁻ and ASMA-HAS2⁺CD44⁻/⁻ mouse lungs with or without bleomycin challenge was compared. Data are shown as the index of invasion value of the fibroblasts with or without bleomycin treatment over ASMA-HAS2⁻ fibroblasts without bleomycin challenge (n=4 per group). The experiments were repeated three times. (K) Increased invasion of bleomycin-treated wild type mouse lung fibroblasts (IgG) was attenuated by neutralizing CD44 antibody (anti-CD44) (n=4 per group). The experiments were performed three times. p values are indicated.
Figure 7:
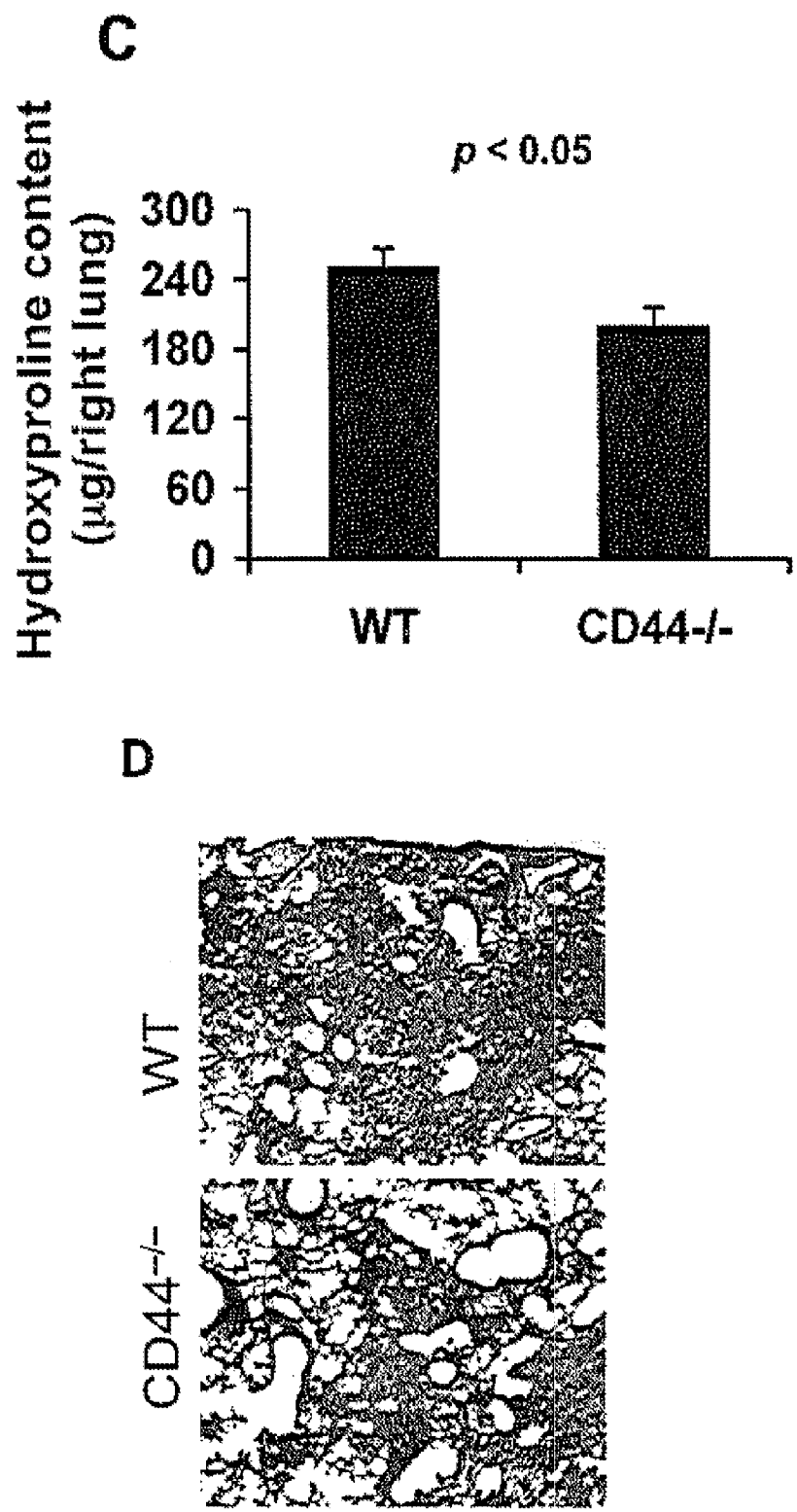
Figure 7:
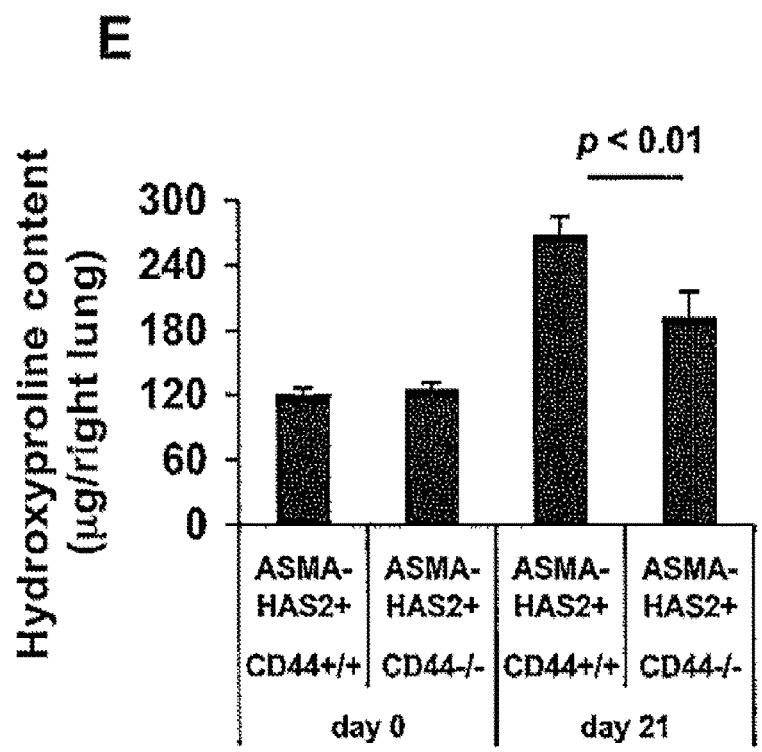
Figure 7:
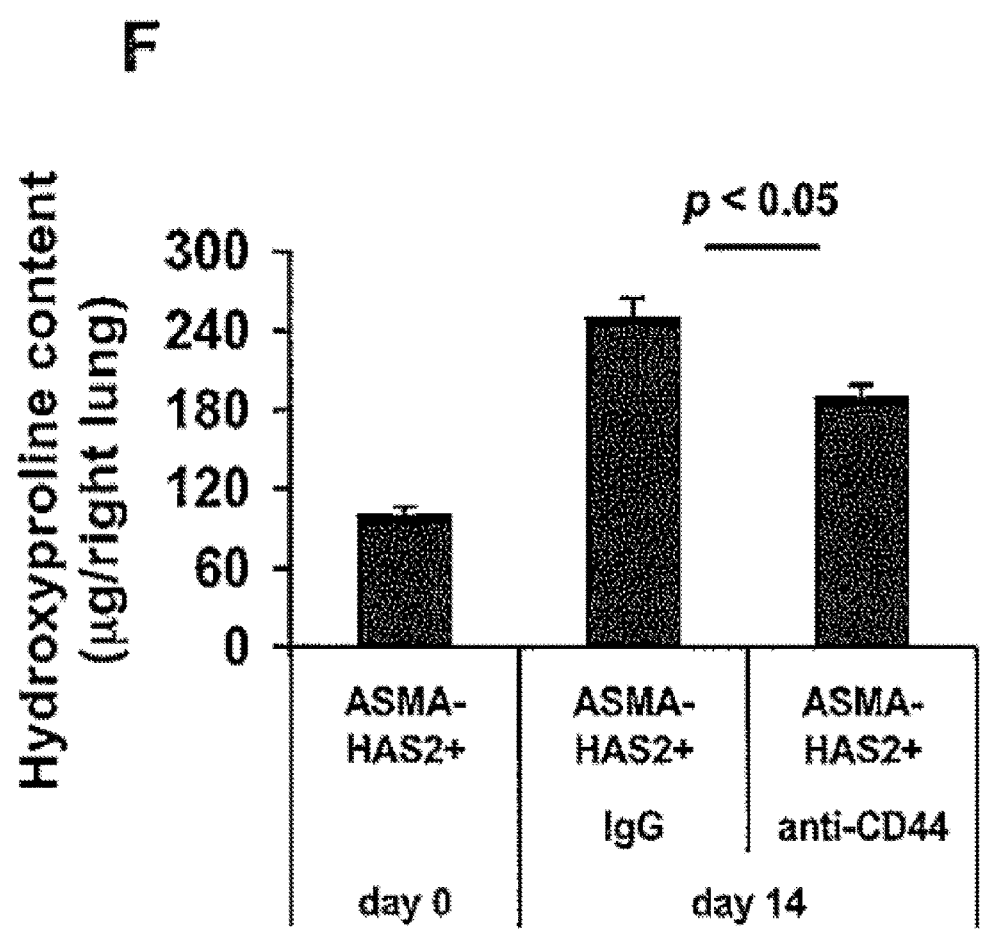
Figure 7:
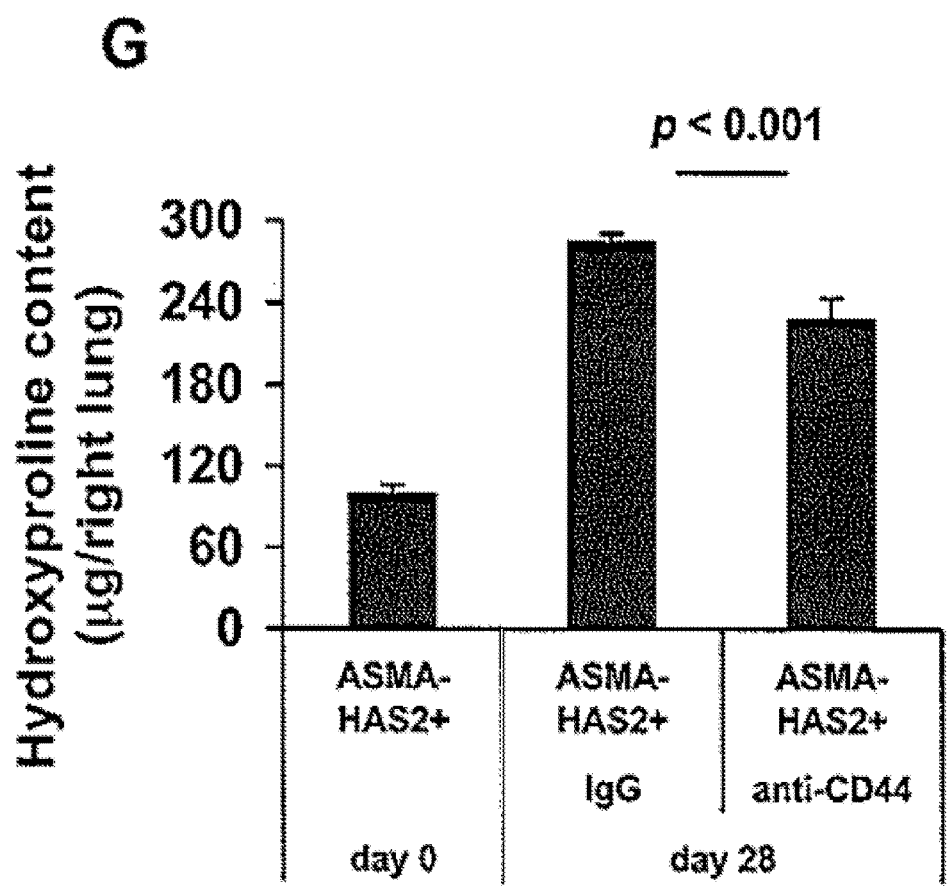
Figure 7:
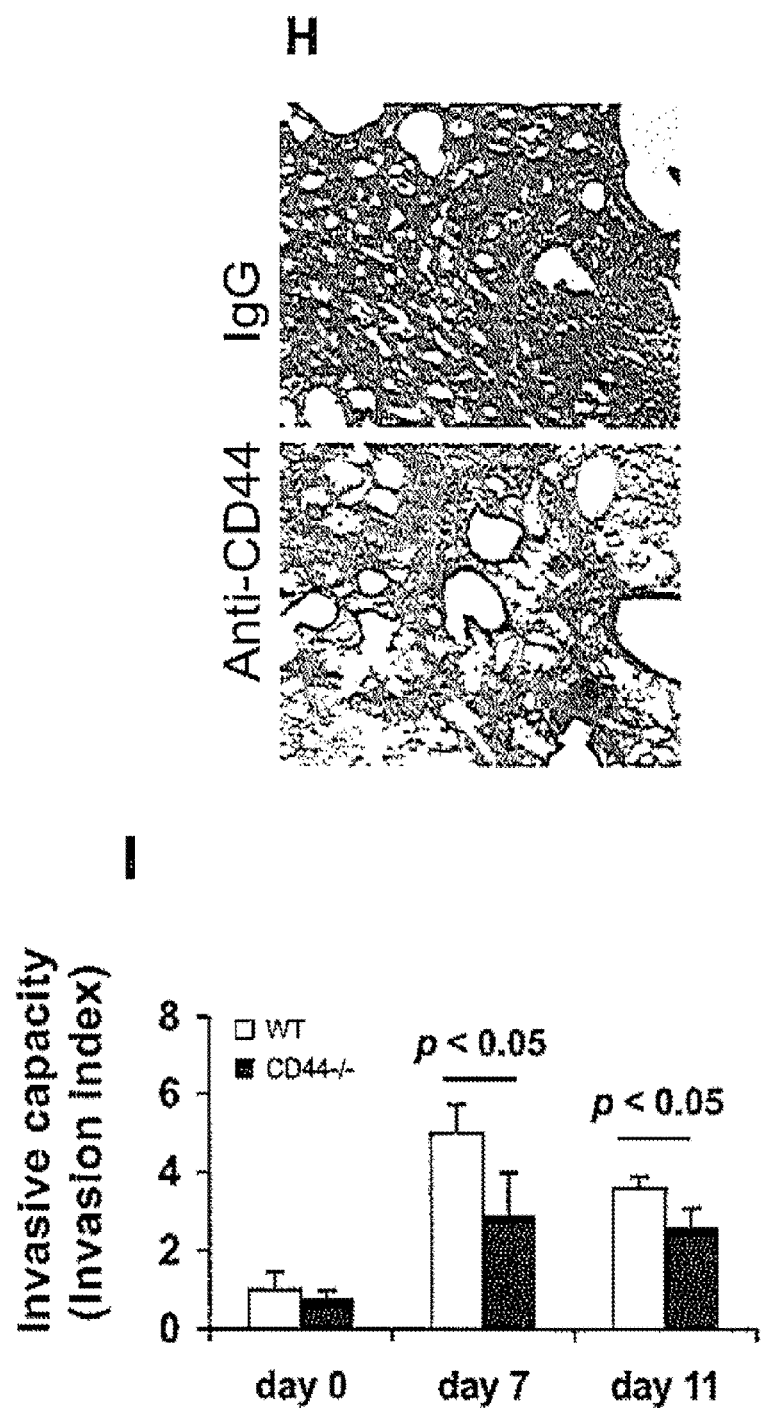
Figure 7:
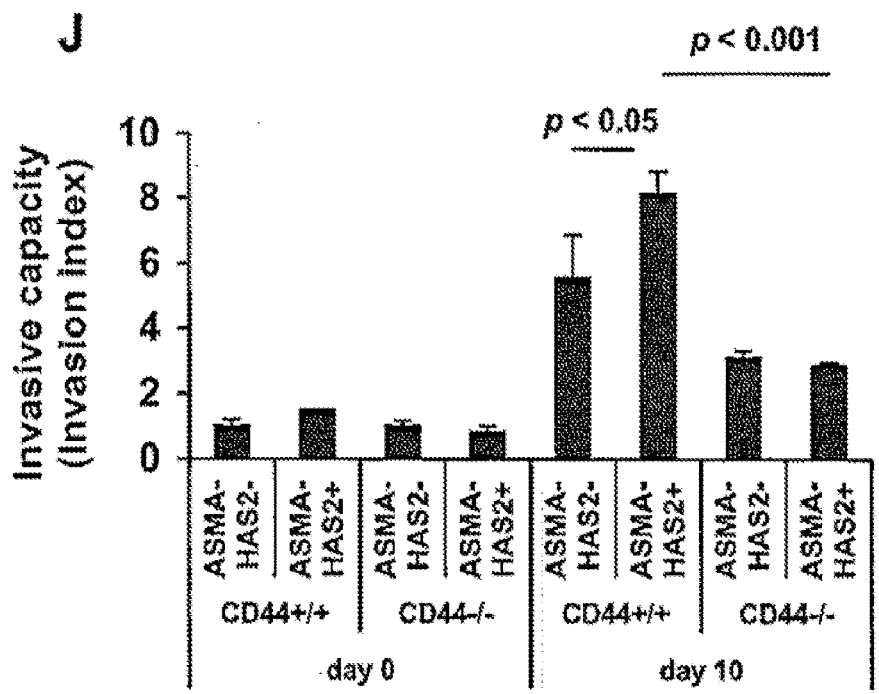
Figure 7:
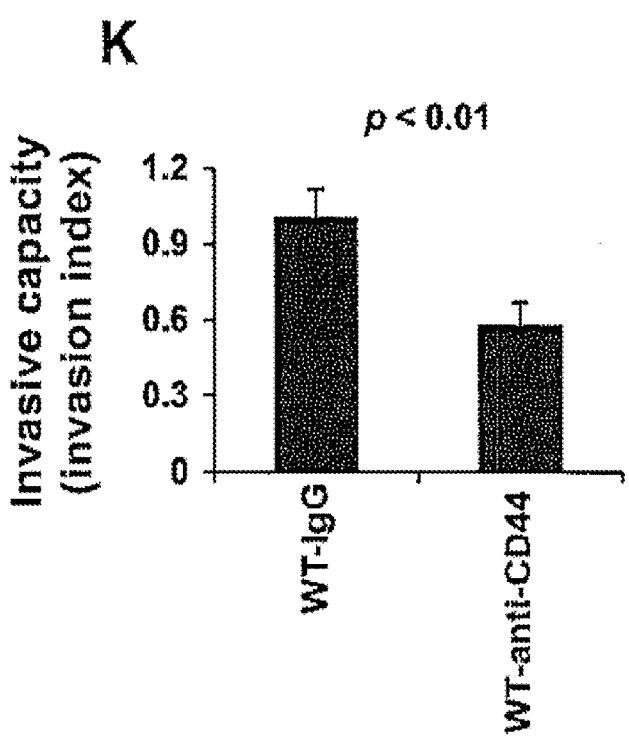

Example 5. Deficiency of CD44 Inhibits the Progression of Pulmonary Fibrosis and Regulates Fibroblast/Myofibroblast Invasion of Extracellular Matrix The cell surface adhesion molecule CD44 is an HA receptor, and macrophage CD44 is involved with clearing HA fragments from injured lung tissue. We found that CD44 was upregulated following bleomycin¬induced lung injury (FIG. 7A,B), and to a greater extent in ASMA-HAS2 transgenic mice (FIG. 7B). We evaluated the role of CD44 in mediating the fibrogenic response in several ways. CD44 null mice showed protection from the development of pulmonary fibrosis (FIG. 7C,D), but the effect was more pronounced when the ASMA-HAS2 transgenic mice were bred with the CD44 null mice (FIG. 7E). We then administered systemic anti-CD44 blocking antibodies or an isotype matched control at the time of lung injury. We found that lung collagen accumulation was largely prevented in the ASMA-HAS2 transgenic mice in the presence of anti-CD44 antibodies (FIG. 7F). To determine if blocking CD44 could be of therapeutic benefit, we treated ASMA-HAS2 transgenic mice with systemic anti-CD44 antibodies or isotype matched control on day 7, 14, and 21 after the bleomycin treatment and analyzed collagen content at day 28. Collagen content was reduced in the presence of CD44 inhibition (FIG. 7G,H).

To determine the role of CD44 in fibroblast invasion we examined the invasive capacity of fibroblasts isolated from CD44 null mice after bleomycin treatment and found impaired invasive capacity (FIG. 7I). Similar results were found from fibroblasts isolated from ASMA-HAS2$^+$/CD44$^{-/-}$ mice relative to control mice (FIG. 7J). Furthermore, treating fibroblasts isolated from bleomycin-challenged wild type C57B1/6J mice with anti-CD44 antibodies blunted fibroblast invasion (FIG. 7K)

Example 6. HAS2 and CD44 Regulate Human IPF Fibroblast Invasion

Figure 8:
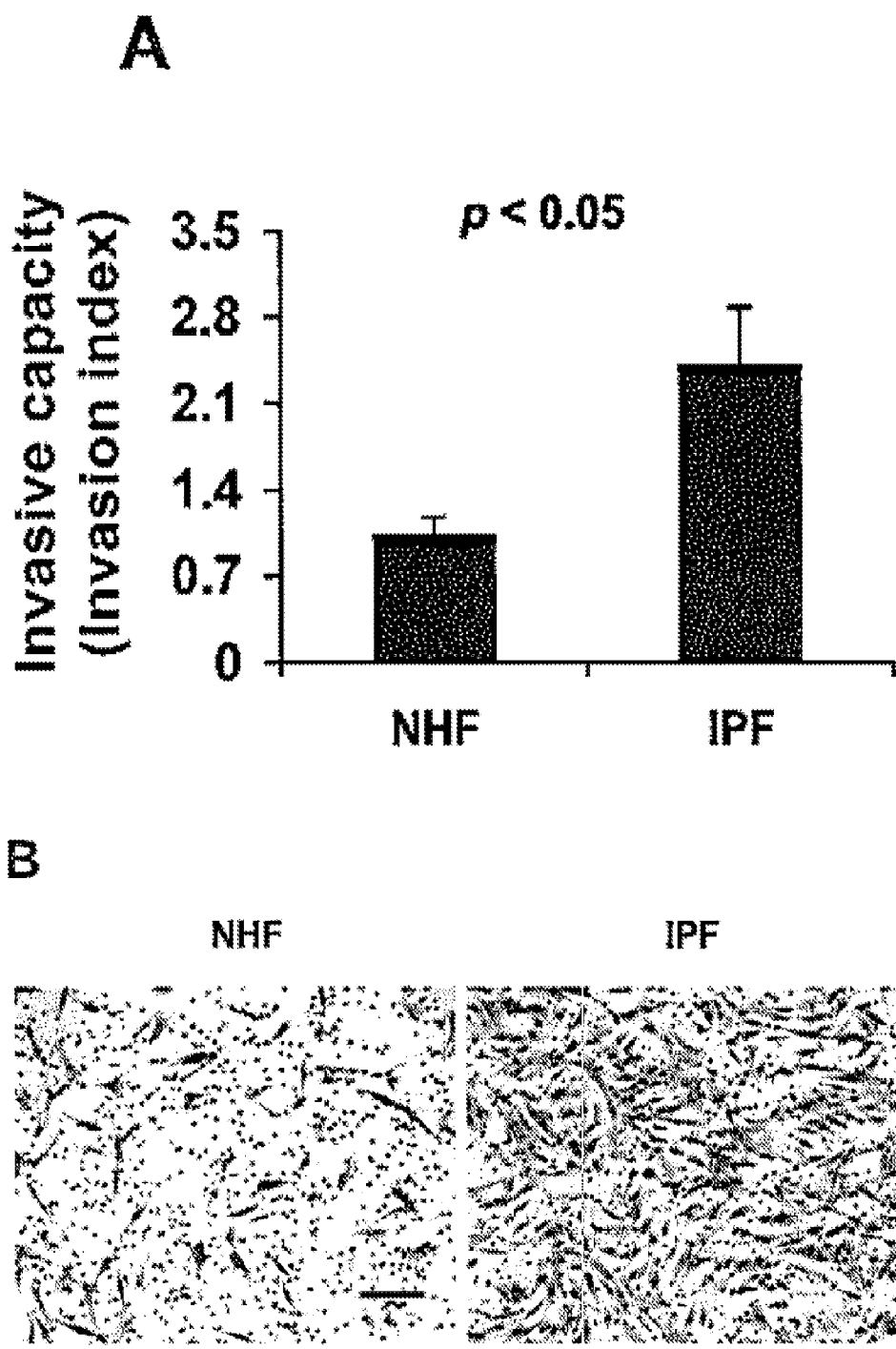
FIG. 8 shows HAS2 and CD44 are associated with human lung fibroblast invasion. (A) Invasive capacity of human fibroblasts from normal subjects (NHF) (n=5) and IPF patients (IPF) (n=9). Results are for 5 separate experiments and are expressed as the invasion index of the IPF fibroblasts over the normal fibroblasts, p value is indicated. (B) Representative images of invasive IPF fibroblasts and normal fibroblasts. (C) Invasive fibroblasts exhibited increased HAS2 expression level (n=7; *p<0.05 by Wilcoxon rank sum test). (D) HAS2 knock down in human lung fibroblasts decreased cell surface HA and inhibited fibroblast invasive capacity. (E) Suppression of HAS2 impaired IPF fibroblast invasion. (F) Neutralizing anti-CD44 antibodies reduced IPF fibroblast invasive capacity.
Figure 8:
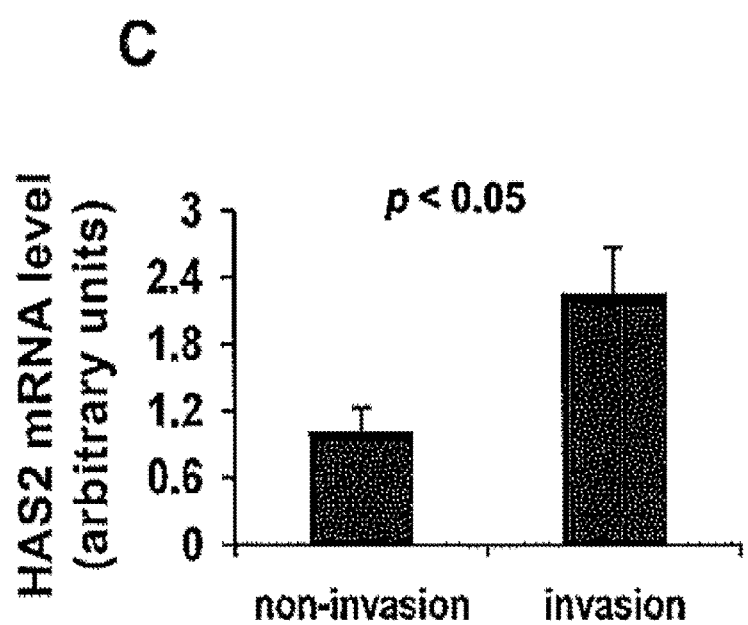
Figure 8:
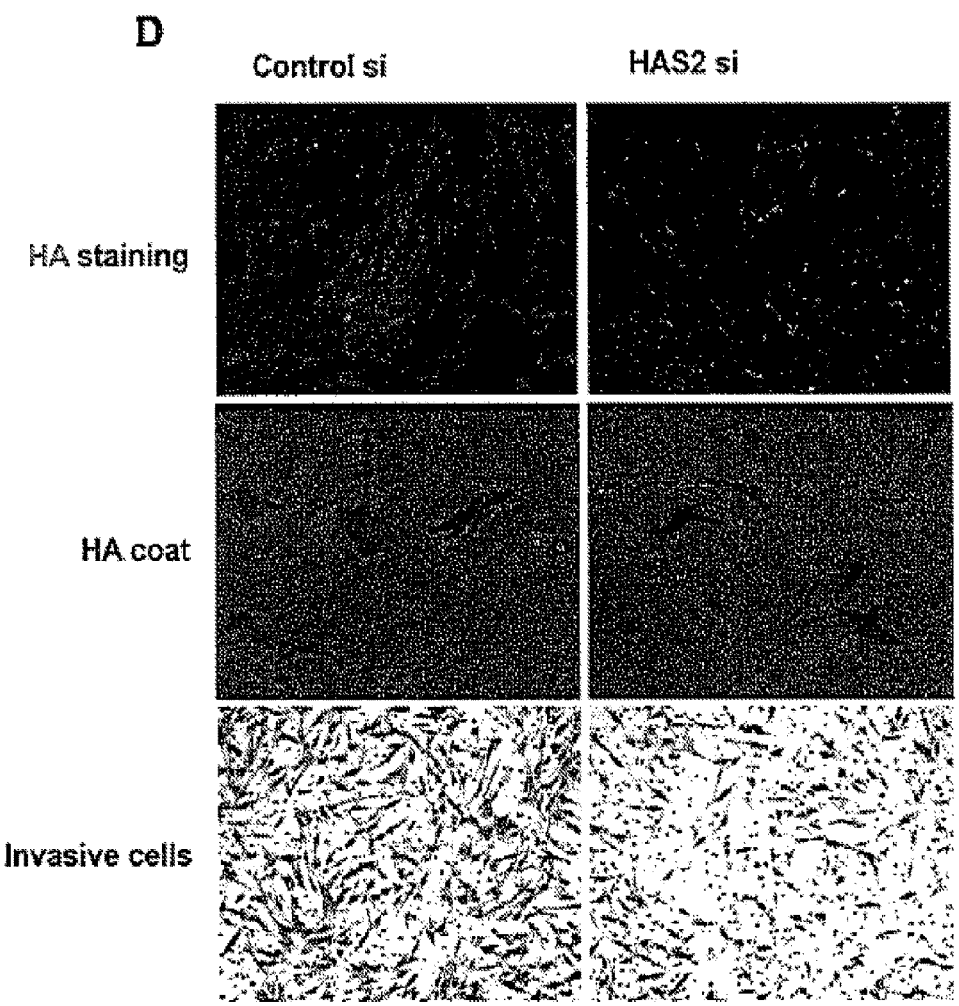
Figure 8:
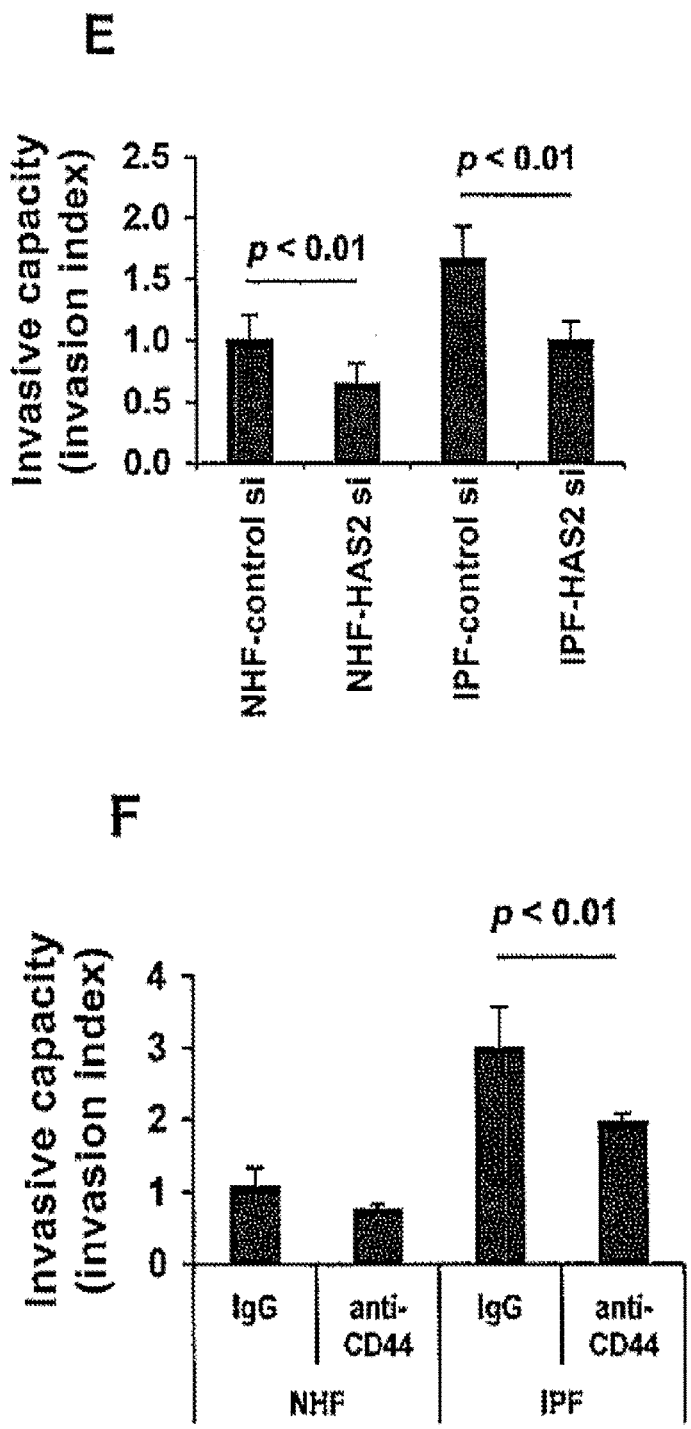
Figure 9:
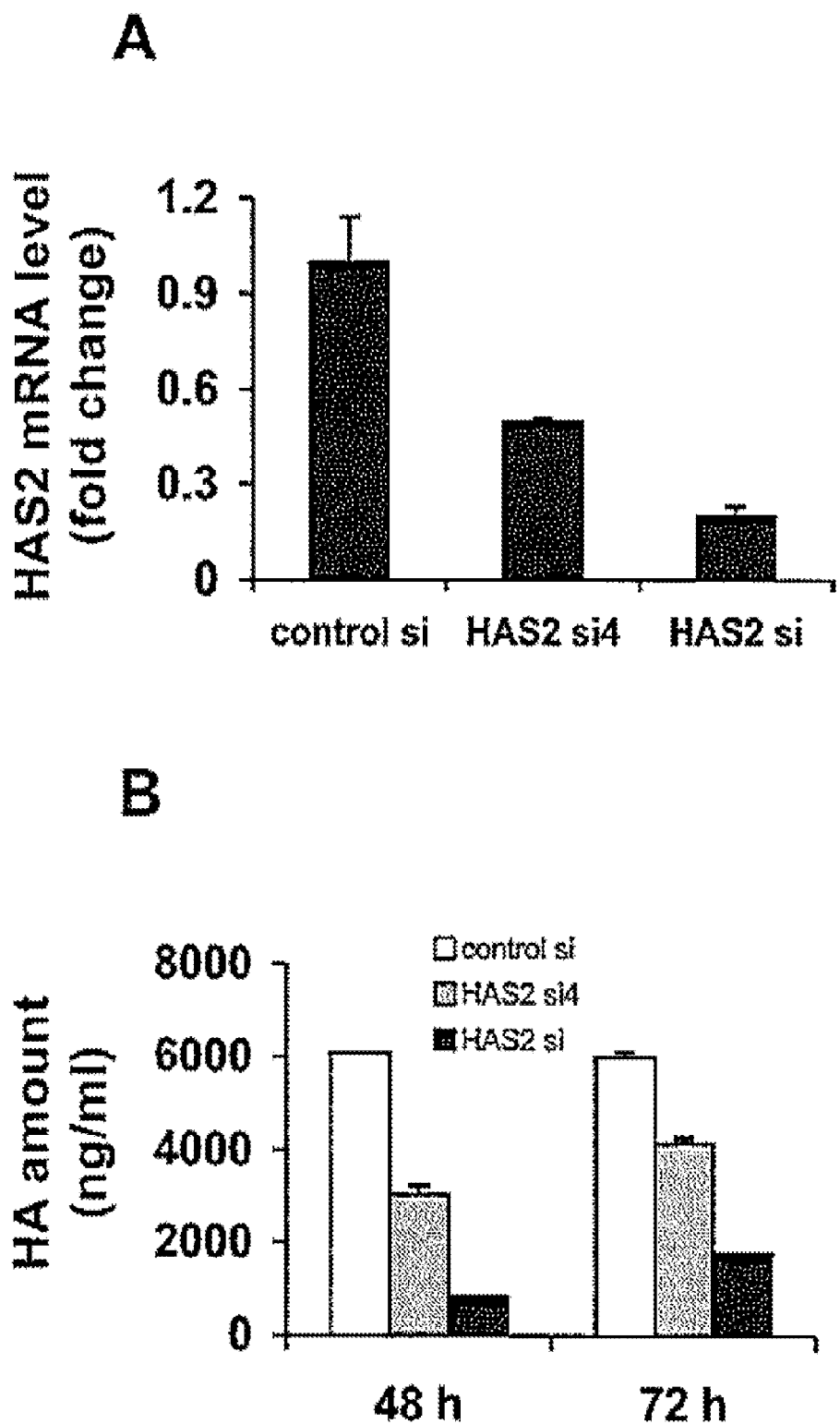
FIG. 9 shows HAS2 siRNA reduces HAS2 gene expression and HA production in primary human lung fibroblasts. (A) HAS2 gene expression levels in primary human lung fibroblasts at 72 h after HAS2 siRNA transfection were measured using real-time PCR. Data shown are representatives of 4 independent experiments. (B) Cell culture media were collected at 48, 72 h after transfection, and HA amount in the media was measured using the HA-ELISA method. Data represent two independent experiments.

To determine if these data obtained from mouse models of fibrosis were relevant to human lung fibrosis, we isolated primary lung fibroblasts from patients with IFF and analyzed their invasive capacity. We found a striking increase in the invasive capacity of IPF fibroblasts compared to fibroblasts isolated from normal lung tissue (FIG. 8A,B). These data suggested that fibroblasts from patients with progressive pulmonary fibrosis acquired an invasive phenotype. Relative HAS2 mRNA levels of invasive and non-invasive IPF fibroblasts were determined using real-time PCR. Interestingly, HAS2 mRNA expression was increased in IPF fibroblasts that invaded matrigel (FIG. 8C; horizontal bars indicate the median expression values). The effect of HAS2 on human lung fibroblast invasion was then investigated by knocking down gene expression using siRNA in primary cells. At 48 h after transfection with HAS2 siRNA (HAS2 si) and control siRNA (control si), fibroblasts were stained for HA with biotin-HABP following by Alexa Fluor 488 conjugated streptavidin. Photomicrographs were taken at a 100× magnification with fixed exposure time. Photomicrographs demonstrating the effects of HAS2 si on HA coat formation were taken at 200× magnification. Images of invasive HAS2 si and control si transfected fibroblasts were shown at 100× magnification. The experiments were repeated three times. At 48 h after HAS2 and control siRNA transfection, equal numbers of fibroblasts from normal donors (n=2) and IPF patients (n=3) were loaded into invasion chambers and incubated for another 24 h. Invasive cells were counted. We found that HAS2 suppression dramatically decreased constitutive HA production (FIG. 8D, and FIG. 9), and markedly inhibited the capacity to invade matrix (FIG. 8D,E). In FIG. 8E, data are shown as the invasion index of HAS2 si transfected normal, IPF fibroblasts, and control si transfected IPF fibroblasts over control si transfected normal fibroblasts. P values are indicated. The experiments were repeated three times. We then treated IFF fibroblasts with anti-CD44 antibodies that recognize human CD44 and demonstrated a marked reduction in invasive capacity (FIG. 8F). Following 20 min of incubation with anti-CD44 neutralizing or isotype-matched control IgG antibody, fibroblasts from normal donors (n=3) and IPF patients (n=6) were subjected to the invasion assay. In FIG. 8F, data are depicted as the invasion index, and P values are indicated. The experiments were repeated three times. Collectively, these data suggested that unrelenting pulmonary fibrosis was dependent upon a matrix invading fibroblast phenotype regulated by HAS2 and CD44.

Figure 10:
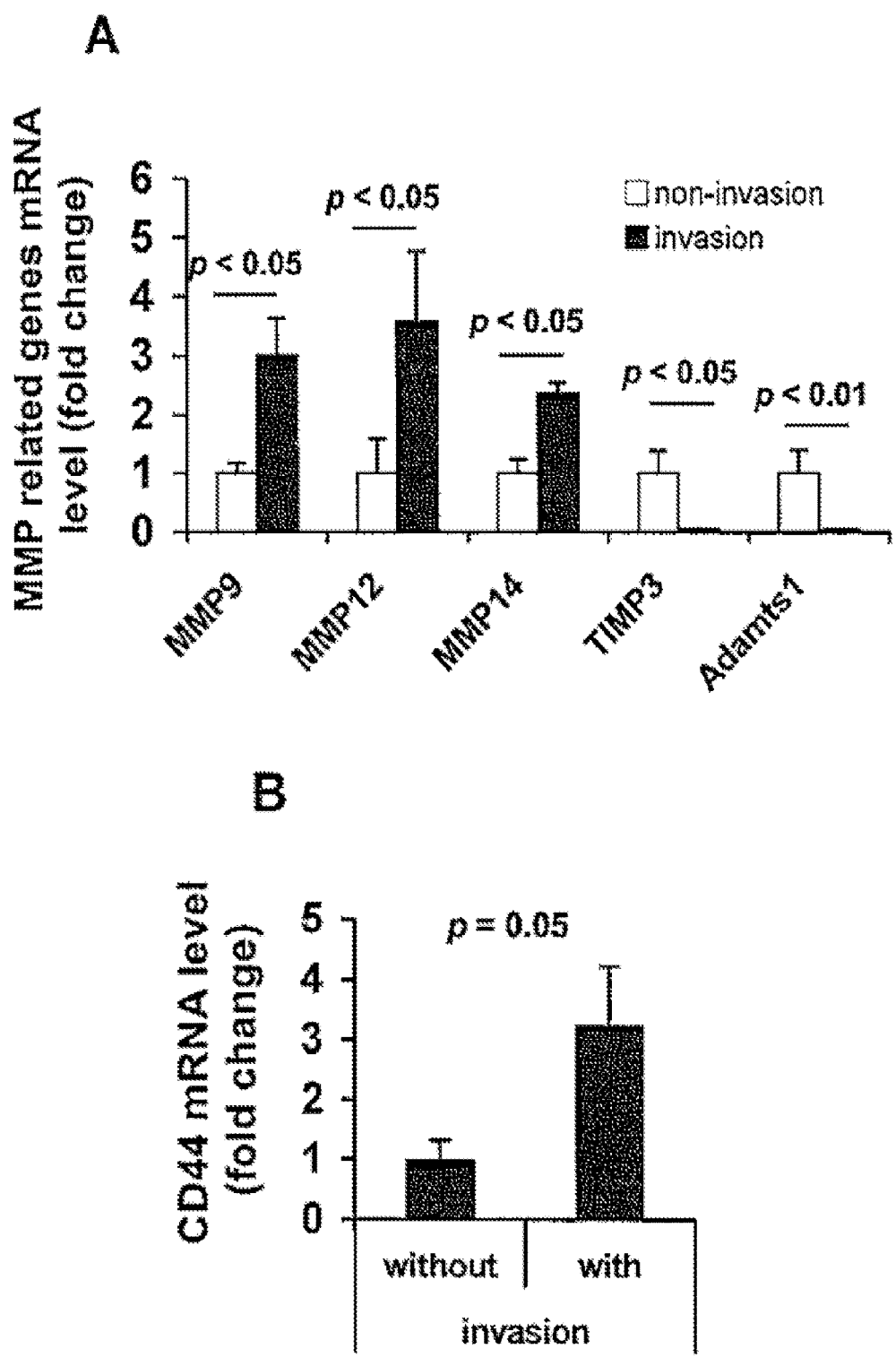
FIG. 10 shows HAS2 promotes fibroblast invasion by regulating CD44 and MMP expression and function. (A-B) qRT-PCR array of RNA extracted from invasive ASMA-HAS2⁺ fibroblasts. (B) CD44 mRNA expression was increased in invasive fibroblasts from bleomycin treated ASMA-HAS2⁺ lungs (n=5; P=0.05). (C) Invasive IPF fibroblasts exhibited increased MMP9 expression (n=5). (D) HAS2 knock down decreased CD44 mRNA expression. (E) Suppression of HAS2 decreased MMP9 mRNA expression. (F) Pro-MMP9 release was increased in the ASMA-HAS2⁺ fibroblast media. (H) Gelatin zymographaphy of protein for MMP9 activity from concentrated fibroblast media with representative image shown (G).
Figure 10:
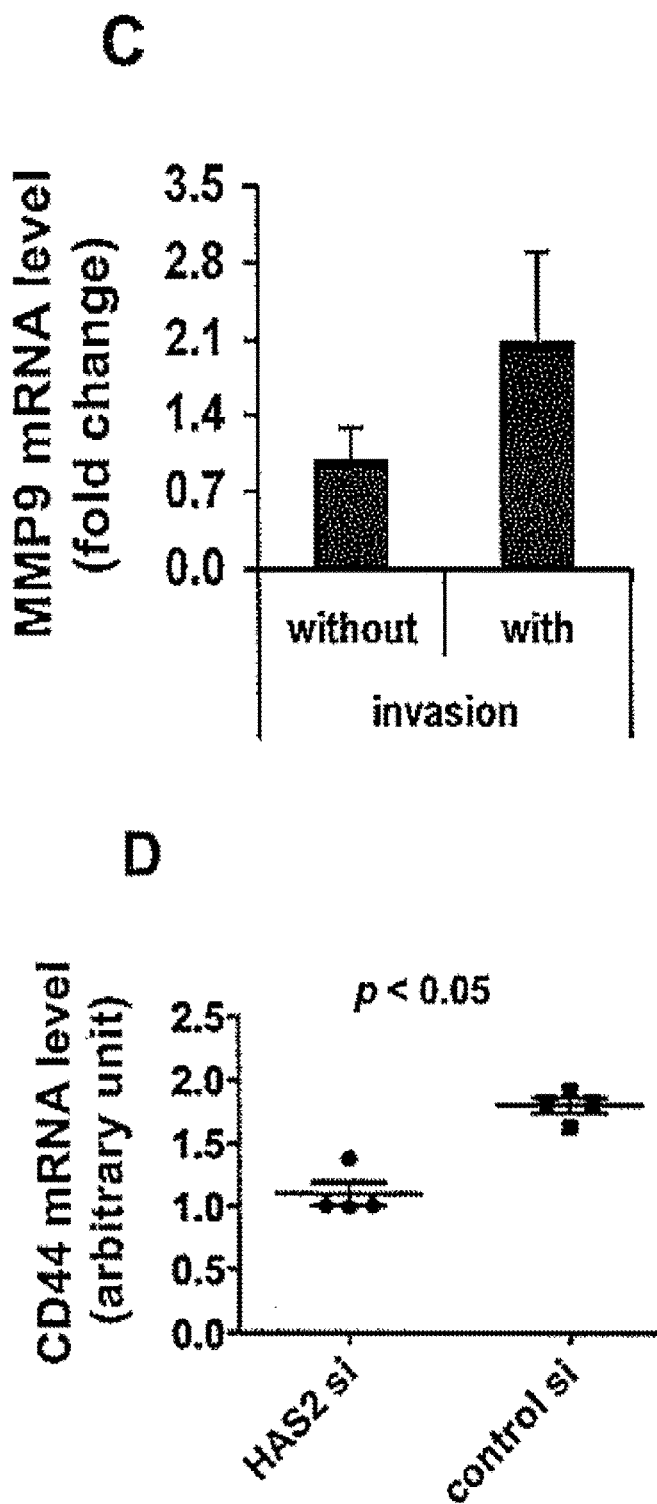
Figure 10:
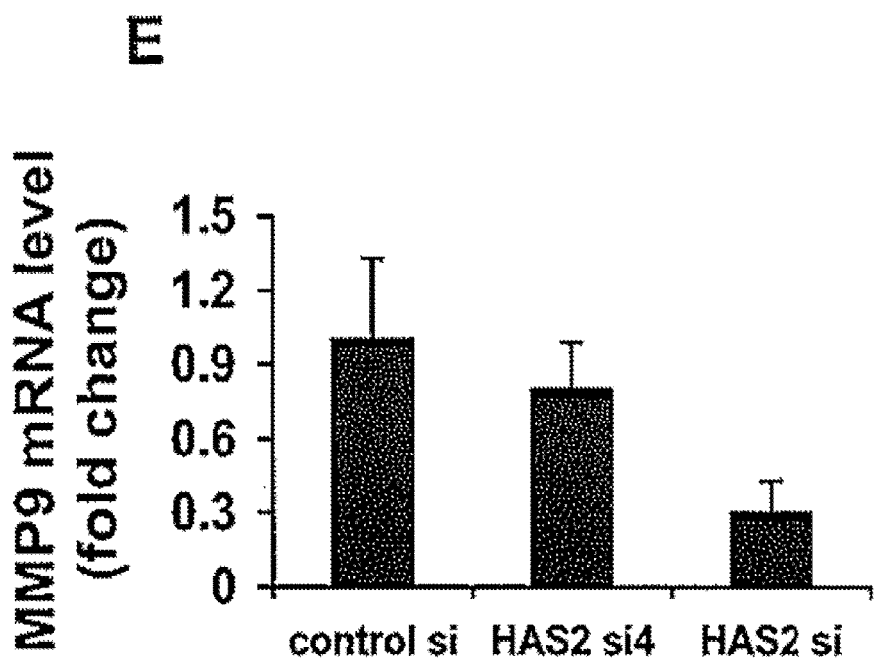
Figure 10:
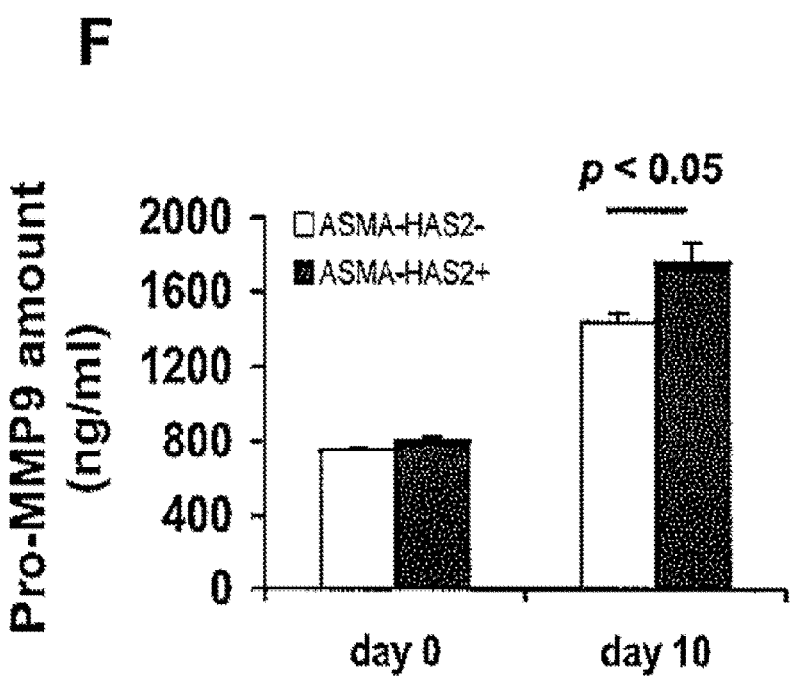
Figure 10:
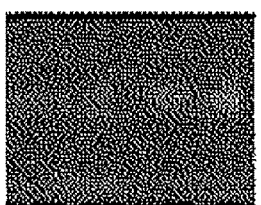
Figure 10:
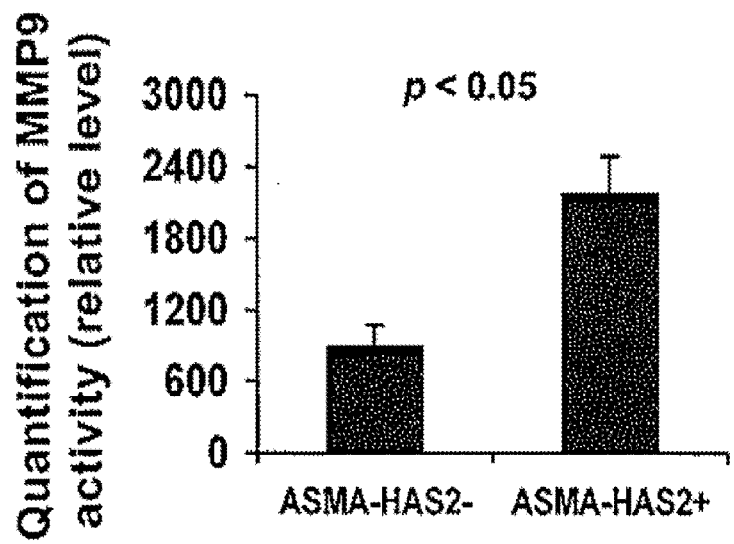

Example 7. HAS2 Regulates Fibroblast Invasion by Modulating CD44 and MMP Expression Levels In order to gain additional insights into the potential mechanisms for the enhanced invasive phenotype of fibroblasts from both a mouse model of severe fibrosis as well as from patients with idiopathic pulmonary fibrosis, we examined patterns of gene expression induced during invasion. Fibroblasts are heterogenous and only a subset are invasive, so we reasoned that clues to the mechanisms regulating invasion could be gained by studying fibroblasts after invasion. Fibroblasts from ASMA-HAS2$^+$ mice were layered onto matrigel-coated wells, and RNA from the fibroblasts that invaded the matrix through to the underlying filter were isolated and qRT-PCR array analysis was performed. Control samples were the fibroblasts that penetrated the filter in the absence of matrigel. 84 genes were analyzed by using a specialized qRT-PCR array for extracellular matrix synthesizing and degrading enzymes. RNA from the fibroblasts that penetrated the filter in the absence of matrigel was used as control. In addition to the upregulation of HAS2 (FIG. 6B) and CD44 (FIG. 10B) expression in invasive cells, we identified a marked up-regulation in the expression of matrix metalloproteinases (MMP9, 12 and 14) (FIG. 10A), which promote fibroblast migration and invasion, and down-regulation of tissue inhibitor of metalloproteinase (TIMP3) (FIG. 10A), which has been shown to inhibit cell invasion of matrix, and ADAMTS1 (FIG. 10A), which has been reported to play a role in renal fibrosis. In FIG. 10A, representative genes up-regulated or down-regulated in invasive ASMA-HAS2$^+$ fibroblasts are shown as bar graphs (n=5; *P<0.05; =**P<0.01 by Wilcoxon rank sum test).

Figure 11:
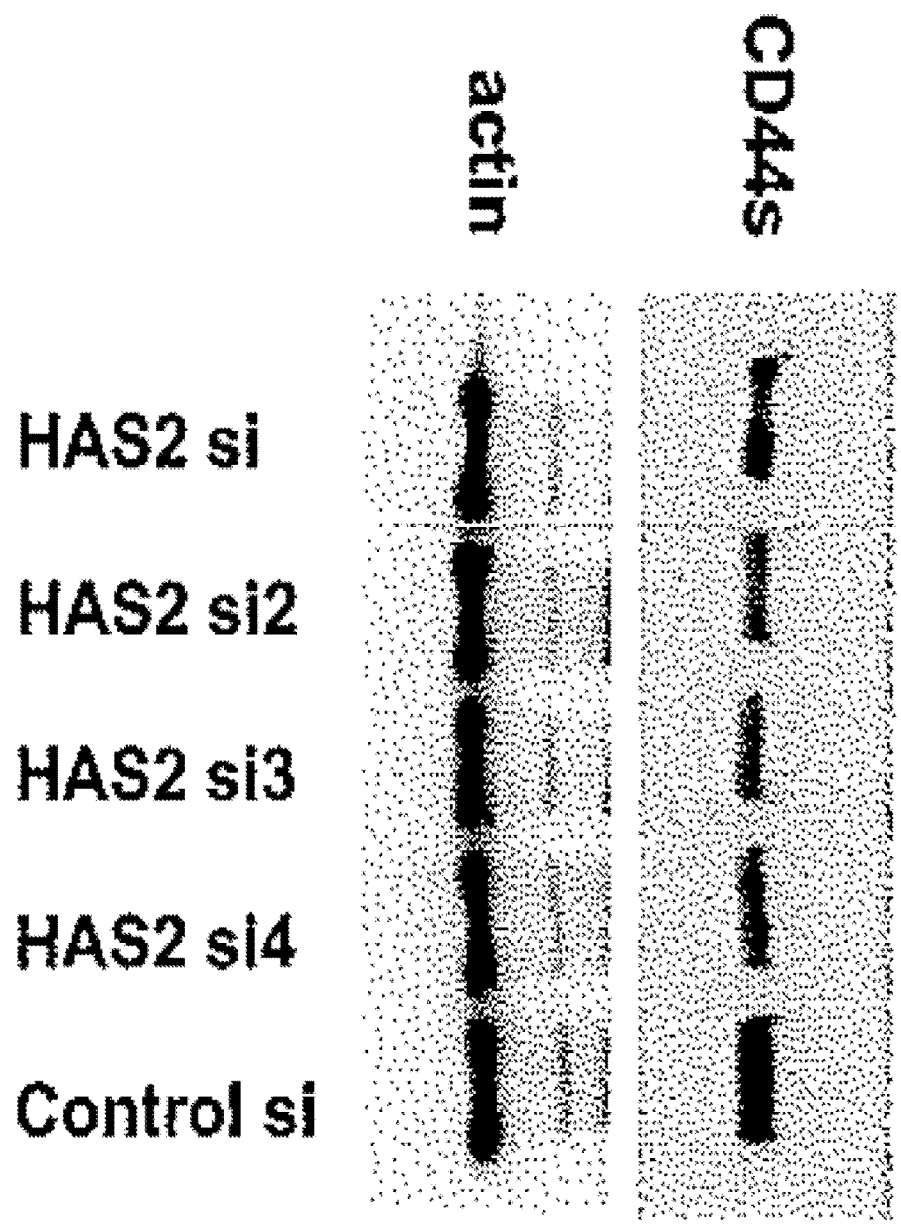
FIG. 11 shows that suppression of HAS2 decreased CD44 protein level.
Figure 12:
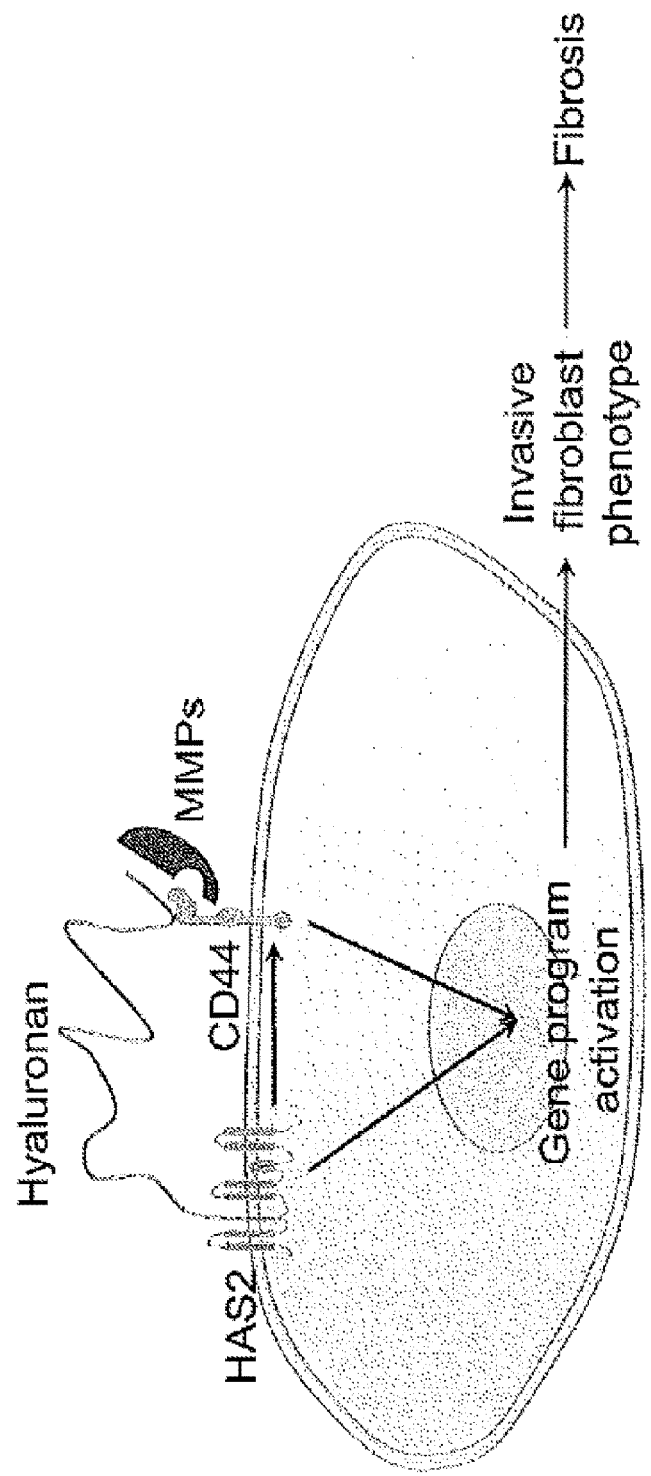
FIG. 12 is a non-limiting schematic illustration of an invasive fibroblast phenotype and severe lung fibrosis.

MMP9 mRNA expression in invasive IPF fibroblasts was compared with IPF fibroblasts that penetrated the filters in the absence of matrigel by using real-time PCR. Similar patterns of gene expression were also observed in invasive IPF fibroblasts, including an up-regulation in MMP9 (FIG. 10C). We then investigated whether the alterations in gene expression was a direct consequence of Has2. CD44 mRNA expression in HAS2 siRNA transfected fibroblasts and control siRNA transfectants were determined using a microarray assay. At 48 h after HAS2 siRNA and control siRNA transfection, fibroblasts were cultured on Matrigel for an additional 6 h. mRNA was then extracted and MMP9 mRNA expression was measured using real-time PCR. Cell lysates were collected from fibroblasts transfected with HAS2 siRNA or control siRNA at 48 h for western blot analysis using antibodies against CD44. Interestingly, we found that HAS2 knock down directly suppressed CD44 and MMP9 gene and protein expression (FIG. 10D,E, and FIG. 11). In FIG. 10D, the horizontal bars indicate the median expression values (n=4; *P<0.05 by Wilcoxon rank sum test). In FIG. 10E, data shown represent one of two separate experiments. Finally, we cultured fibroblasts from ASMA-HAS2$^+$ and wild type mice in matrigel. Fibroblasts from ASMA-HAS2$^-$ and ASMA-HAS2$^+$ mice were cultured on matrigel for 96 h. Pro-MMP9 protein in the media was measured using a Pro-MMP9 ELISA kit (n=3-7 per group; P value is indicated). The experiments were performed three times. We found that fibroblasts from ASMA-HAS2$^+$ fibroblasts secreted more pro-MMP9 than fibroblasts from control ASMA-HAS2$^-$ mice (FIG. 10F) that was enzymatically active (FIG. 10G,H; n=4-5 per group. p values are indicated). The media was concentrated 10× using Microsep centrifugal devices. The experiments were repeated two times. Protein amount was normalized and quantification analysis of gelatin zymographaphy for MMP9 activity results by using NIH Image J software. Collectively, these data suggested that HA-CD44 interactions and upregulation of HAS2 in the context of matrix induced the activation of a gene program that promoted an invasive fibroblast phenotype and severe fibrosis. We have schematically depicted this concept (FIG. 12). Following lung injury, HAS2 is upregulated and synthesized HA for release as well as potentially interacting with CD44 on the cell surface. CD44 is upregulated and "activated" to interact with MMPs to facilitate tissue invasion. HAS2 upregulation also contributes to activation of a program of gene expression that further promotes a myofibroblast invasive phenotype and resultant severe fibrosis.

What is claimed is:

1. A method of targeting an invasive fibroblast phenotype and treating pulmonary fibrosis comprising formation of excess fibrous connective tissue in the lung and accumulation of myofibroblasts comprising the invasive fibroblast phenotype that invade extracellular matrix of the lung in a subject, the method comprising:
administering to the subject a pharmaceutical composition comprising a therapeutic amount of an siRNA HAS2 inhibitor targeting a region selected from 1530-1550 nt, 1051-1071 nt, 1424-1444 nt, and 1777-1797 nt of SEQ ID NO. 20,
wherein the therapeutic amount reduces collagen and the formation of excess fibrous connective tissue in the lung, reduces accumulation of myofibroblasts comprising the invasive fibroblast phenotype that invade extracellular matrix of the lung, and alters expression in the invasive fibroblast phenotype characterized by one or more of: up-regulation of MMP-9, up-regulation of MMP-12, up-regulation of MMP-14, down-regulation of TIMP3, and down-regulation of ADAMTS1, relative to an untreated control.

2. The method of claim 1, wherein the pharmaceutical composition inhibits the biological activity of HAS2.

3. The method of claim 1, wherein the pharmaceutical composition inhibits the biological activity of CD44.

4. The method of claim 1, wherein the pharmaceutical composition further comprises an antibody.

5. The method of claim 1, wherein the biological activity of both HAS2 and CD44 are reduced.

6. The method of claim 1, wherein the siRNA HAS2 inhibitor comprises a nucleotide sequence of SEQ ID NO. 15.

* * * * *